United States Patent
Jia et al.

(10) Patent No.: US 11,866,451 B2
(45) Date of Patent: Jan. 9, 2024

(54) SALTS AND CRYSTALLINE FORMS OF A PD-1/PD-L1 INHIBITOR

(71) Applicant: Incyte Corporation, Wilmington, DE (US)

(72) Inventors: Zhongjiang Jia, Kennett Square, PA (US); Shili Chen, Newark, DE (US); Yi Li, Newark, DE (US); Timothy Martin, Hockessin, DE (US); Bo Shen, Garnet Valley, PA (US); Naijing Su, Hockessin, DE (US); Jiacheng Zhou, Newark, DE (US); Qun Li, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 178 days.

(21) Appl. No.: 17/094,396

(22) Filed: Nov. 10, 2020

(65) Prior Publication Data

US 2021/0139511 A1 May 13, 2021

Related U.S. Application Data

(60) Provisional application No. 63/022,131, filed on May 8, 2020, provisional application No. 62/933,869, filed on Nov. 11, 2019.

(51) Int. Cl.
| | | |
|---|---|---|
| C07D 519/00 | (2006.01) | |
| A61K 9/00 | (2006.01) | |
| C07C 61/135 | (2006.01) | |
| C07C 211/56 | (2006.01) | |

(52) U.S. Cl.
CPC .......... *C07D 519/00* (2013.01); *A61K 9/0053* (2013.01); *C07C 61/135* (2013.01); *C07C 211/56* (2013.01); *C07B 2200/13* (2013.01)

(58) Field of Classification Search
CPC ... C07D 519/00; C07C 61/135; C07C 211/56; C07C 2602/42; C07B 2200/13
See application file for complete search history.

(56) References Cited

U.S. PATENT DOCUMENTS

| | | | |
|---|---|---|---|
| 3,272,781 A | 9/1966 | Goodrow | |
| 4,208,328 A | 6/1980 | Lavallee et al. | |
| 4,789,711 A | 12/1988 | Monnier et al. | |
| 5,077,164 A | 12/1991 | Ueda et al. | |
| 6,114,497 A | 9/2000 | Tada et al. | |
| 6,297,351 B1 | 10/2001 | Murayama et al. | |
| 6,372,907 B1 | 4/2002 | Lee et al. | |
| 6,521,618 B2 | 2/2003 | Boschelli et al. | |
| 6,867,200 B1 | 3/2005 | Allen et al. | |
| 7,320,989 B2 | 1/2008 | Anderson et al. | |
| 7,417,065 B2 | 8/2008 | Mi et al. | |
| 7,488,802 B2 | 2/2009 | Collins et al. | |
| 7,491,245 B2 | 2/2009 | Glenn et al. | |
| 7,691,870 B2 | 4/2010 | Buchstaller et al. | |
| 7,851,489 B2 | 12/2010 | Borzilleri et al. | |
| 7,943,743 B2 | 5/2011 | Korman et al. | |
| 8,008,449 B2 | 8/2011 | Korman et al. | |
| 8,163,743 B2 | 4/2012 | Baldwin et al. | |
| 8,168,757 B2 | 5/2012 | Finnefrock et al. | |
| 8,217,149 B2 | 7/2012 | Irving et al. | |
| 8,541,424 B2 | 9/2013 | DeGoey et al. | |
| 8,993,604 B2 | 3/2015 | Byrd et al. | |
| 9,085,576 B2 | 7/2015 | Minatti et al. | |
| 9,163,017 B2 | 10/2015 | DeGoey et al. | |
| 9,394,365 B1* | 7/2016 | Eisenbach-Schwartz ................... A61K 31/7068 | |
| 9,540,322 B2 | 1/2017 | Jorgensen et al. | |
| 9,603,950 B1 | 3/2017 | Li et al. | |
| 9,611,261 B2 | 4/2017 | Minatti et al. | |
| 9,643,922 B2 | 5/2017 | Jorgensen et al. | |
| 10,017,520 B2 | 7/2018 | Koehler et al. | |
| 10,202,343 B2 | 2/2019 | Jorgensen et al. | |
| 10,308,644 B2 | 6/2019 | Wu et al. | |
| 10,618,916 B2 | 4/2020 | Wu et al. | |
| 10,669,271 B2 | 6/2020 | Wu et al. | |
| 10,793,505 B2 | 10/2020 | Wu et al. | |
| 10,793,565 B2 | 10/2020 | Wu et al. | |
| 10,800,768 B2 | 10/2020 | Wu et al. | |
| 10,806,785 B2 | 10/2020 | Liu et al. | |
| 10,906,920 B2 | 2/2021 | Wu et al. | |
| 11,124,511 B2 | 9/2021 | Wu et al. | |
| 11,339,149 B2 | 5/2022 | Wu et al. | |
| 11,401,279 B2 | 8/2022 | Li et al. | |
| 11,407,749 B2 | 8/2022 | Wu et al. | |
| 11,414,433 B2 | 8/2022 | Wu et al. | |

(Continued)

FOREIGN PATENT DOCUMENTS

| | | |
|---|---|---|
| CA | 2355249 | 6/2000 |
| CA | 3099994 | 11/2019 |

(Continued)

OTHER PUBLICATIONS

Bhattacharya et al. (Brittain, ed. Polymorphism in Pharmaceutical Solids, 2009, p. 334.*
Abdellaoui et al., "Palladium-catalyzed non-directed C—H bond arylation of difluorobenzenes and dichlorobenzenes bearing benzoxazole or benzothiazole," Catalysis Communications, 2015, 71:13-16.
Ahmed et al., "Enantioselective Polymerization of Epoxides Using Biaryl-Linked Bimetallic Cobalt Catalysts: A Mechanistic Study," J Am Chem Soc., 2013, 135(50): 18901-18911.
Alverez et al., "Structure—Activity Study of Bioisosteric Trifluoromethyl and Pentafluorosulfanyl Indole Inhibitors of the AAA ATPase p97," ACS Med Chem., 2015, 6(12):1225-1230.

(Continued)

*Primary Examiner* — Sahar Javanmard
(74) *Attorney, Agent, or Firm* — Fish & Richardson P.C.

(57) ABSTRACT

This application relates to solid forms and salt forms of the PD-1/PD-L1 inhibitor 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid), including processes of preparation thereof, where the solid forms and salt forms are useful in the treatment of various diseases including infectious diseases and cancer.

33 Claims, 41 Drawing Sheets

(56) References Cited

U.S. PATENT DOCUMENTS

| | | |
|---|---|---|
| 11,465,981 B2 | 10/2022 | Wu et al. |
| 11,566,026 B2 | 1/2023 | Wu et al. |
| 11,572,366 B2 | 2/2023 | Li et al. |
| 11,608,337 B2 | 3/2023 | Li et al. |
| 11,613,536 B2 | 3/2023 | Wu et al. |
| 11,673,883 B2 | 6/2023 | Lu et al. |
| 2002/0082266 A1 | 6/2002 | Gallant et al. |
| 2003/0134843 A1 | 7/2003 | Lubisch et al. |
| 2003/0191115 A1 | 10/2003 | Pinto et al. |
| 2004/0018986 A1 | 1/2004 | Pitlik et al. |
| 2004/0058938 A1 | 3/2004 | Cullmann et al. |
| 2004/0063963 A1 | 4/2004 | Ueno et al. |
| 2004/0082635 A1 | 4/2004 | Hashimoto et al. |
| 2004/0186114 A1 | 9/2004 | Cirillo et al. |
| 2004/0214040 A1 | 10/2004 | Lee et al. |
| 2005/0187230 A1 | 8/2005 | Ding et al. |
| 2005/0245536 A1 | 11/2005 | Hao et al. |
| 2005/0260126 A1 | 11/2005 | Kudo et al. |
| 2005/0288295 A1 | 12/2005 | Currie et al. |
| 2006/0004010 A1 | 1/2006 | Habashita et al. |
| 2006/0084650 A1 | 4/2006 | Dong et al. |
| 2006/0089362 A1 | 4/2006 | Seno et al. |
| 2006/0178367 A1 | 8/2006 | Currie et al. |
| 2006/0183746 A1 | 8/2006 | Currie et al. |
| 2006/0229337 A1 | 10/2006 | Brittelli et al. |
| 2006/0270686 A1 | 11/2006 | Kelly et al. |
| 2007/0099938 A1 | 5/2007 | Ohmoto et al. |
| 2007/0191395 A1 | 8/2007 | Kawakami et al. |
| 2008/0045536 A1 | 2/2008 | Vaccaro et al. |
| 2008/0139557 A1 | 6/2008 | Blomgren et al. |
| 2008/0153834 A1 | 6/2008 | Blomgren et al. |
| 2008/0280891 A1 | 11/2008 | Kelly et al. |
| 2009/0163545 A1 | 6/2009 | Goldfarb |
| 2009/0253735 A1 | 10/2009 | Almario-Garcia et al. |
| 2009/0281075 A1 | 11/2009 | Roughton et al. |
| 2009/0281120 A1 | 11/2009 | Nakai et al. |
| 2009/0304821 A1 | 12/2009 | Notoya et al. |
| 2010/0155712 A1 | 6/2010 | Kitamura |
| 2010/0160292 A1 | 6/2010 | Whitney et al. |
| 2010/0160303 A1 | 6/2010 | Liu et al. |
| 2010/0249151 A1 | 9/2010 | Klein et al. |
| 2010/0267775 A1 | 10/2010 | Negoro et al. |
| 2010/0267778 A1 | 10/2010 | Kusuda et al. |
| 2010/0273832 A1 | 10/2010 | Jung et al. |
| 2010/0292227 A1 | 11/2010 | Yoakim et al. |
| 2011/0053915 A1 | 3/2011 | Ivaschenko et al. |
| 2011/0062858 A1 | 3/2011 | Yersin et al. |
| 2011/0065699 A1 | 3/2011 | De Peretti et al. |
| 2011/0065700 A1 | 3/2011 | De Peretti et al. |
| 2011/0065745 A1 | 3/2011 | De Peretti et al. |
| 2011/0124640 A1 | 5/2011 | Liu et al. |
| 2011/0294781 A1 | 12/2011 | Yamamoto et al. |
| 2011/0301145 A1 | 12/2011 | Barbosa, Jr. et al. |
| 2012/0058996 A1 | 3/2012 | Liu et al. |
| 2012/0295884 A1 | 11/2012 | Altmann et al. |
| 2012/0323002 A1 | 12/2012 | Yamamoto et al. |
| 2012/0328569 A1 | 12/2012 | McComas et al. |
| 2013/0096118 A1 | 4/2013 | Liu et al. |
| 2013/0131063 A1 | 5/2013 | Castro et al. |
| 2013/0203741 A1 | 8/2013 | Suzuki et al. |
| 2013/0203747 A1 | 8/2013 | Yoakim et al. |
| 2013/0203754 A1 | 8/2013 | Yang et al. |
| 2013/0253011 A1 | 9/2013 | Jung et al. |
| 2014/0058097 A1 | 2/2014 | Kobayashi et al. |
| 2014/0088117 A1 | 3/2014 | Burch et al. |
| 2014/0128382 A1 | 5/2014 | Wu et al. |
| 2014/0243306 A1 | 8/2014 | Heng et al. |
| 2014/0275058 A1 | 9/2014 | Minatti et al. |
| 2014/0288094 A1 | 9/2014 | Bennett et al. |
| 2014/0378447 A1 | 12/2014 | Okano et al. |
| 2015/0005279 A1 | 1/2015 | Bonafoux et al. |
| 2015/0011751 A1 | 1/2015 | Kawakami et al. |
| 2015/0073024 A1 | 3/2015 | Sasikumar et al. |
| 2015/0181880 A1 | 7/2015 | Takahashi |
| 2015/0210680 A1 | 7/2015 | Kobayashi et al. |
| 2015/0232478 A1 | 8/2015 | Ishida et al. |
| 2015/0239868 A1 | 8/2015 | Pais et al. |
| 2015/0252011 A1 | 9/2015 | Minatti et al. |
| 2015/0258505 A1 | 9/2015 | Hironaka et al. |
| 2015/0291549 A1 | 10/2015 | Chupak et al. |
| 2015/0299227 A1 | 10/2015 | Wolkenberg et al. |
| 2015/0307465 A1 | 10/2015 | Scott et al. |
| 2015/0376172 A1 | 12/2015 | Guba et al. |
| 2016/0015690 A1 | 1/2016 | Babaoglu et al. |
| 2016/0046648 A1 | 2/2016 | Petrukhin et al. |
| 2016/0130251 A1 | 5/2016 | Graupe et al. |
| 2016/0194295 A1 | 7/2016 | Sasikumar et al. |
| 2016/0229816 A1 | 8/2016 | Sato et al. |
| 2016/0280695 A1 | 9/2016 | Minatti et al. |
| 2017/0107216 A1 | 4/2017 | Wu et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0304282 A1 | 10/2017 | Rocco et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0057486 A1 | 3/2018 | Wu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0273519 A1 | 9/2018 | Wu et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0270706 A1 | 9/2019 | Jorgensen et al. |
| 2019/0300524 A1 | 10/2019 | Wu et al. |
| 2019/0345170 A1 | 11/2019 | Wu et al. |
| 2020/0172533 A1 | 6/2020 | Wu et al. |
| 2020/0172541 A1 | 6/2020 | Li et al. |
| 2020/0181126 A1 | 6/2020 | Lu et al. |
| 2020/0255424 A1 | 8/2020 | Wu et al. |
| 2020/0277309 A1 | 9/2020 | Wu et al. |
| 2020/0283423 A1 | 9/2020 | Yu et al. |
| 2020/0325115 A1 | 10/2020 | Wu et al. |
| 2020/0397893 A1 | 12/2020 | Liu et al. |
| 2020/0407357 A1 | 12/2020 | Lajkiewicz et al. |
| 2021/0002276 A1 | 1/2021 | Wu et al. |
| 2021/0017164 A1 | 1/2021 | Lu et al. |
| 2021/0017175 A1 | 1/2021 | Li et al. |
| 2021/0040090 A1 | 2/2021 | Jia et al. |
| 2021/0094976 A1 | 4/2021 | Li et al. |
| 2021/0107900 A1 | 4/2021 | Wu et al. |
| 2021/0115025 A1 | 4/2021 | Yu et al. |
| 2021/0115068 A1 | 4/2021 | Wu et al. |
| 2021/0221819 A1 | 7/2021 | Li et al. |
| 2021/0317139 A1 | 10/2021 | Xiao et al. |
| 2021/0347771 A1 | 11/2021 | Wu et al. |
| 2021/0363137 A1 | 11/2021 | Wu et al. |
| 2021/0380584 A1 | 12/2021 | Wu et al. |
| 2022/0089588 A1 | 3/2022 | Wu et al. |
| 2022/0144830 A1 | 5/2022 | Zhou et al. |
| 2022/0144831 A1 | 5/2022 | Wang et al. |
| 2022/0144832 A1 | 5/2022 | Jia et al. |
| 2022/0193050 A1 | 6/2022 | Yang et al. |
| 2022/0194931 A1 | 6/2022 | Wu et al. |
| 2022/0213090 A1 | 7/2022 | Wu et al. |
| 2022/0340600 A1 | 10/2022 | Li et al. |
| 2022/0348594 A1 | 11/2022 | Wu et al. |
| 2023/0100875 A1 | 3/2023 | Lajkiewicz et al. |
| 2023/0146129 A1 | 5/2023 | Wu et al. |
| 2023/0149409 A1 | 5/2023 | Geschwindt et al. |

FOREIGN PATENT DOCUMENTS

| | | |
|---|---|---|
| CL | 2018001531 | 7/2018 |
| CL | 2018003734 | 2/2019 |

(56) References Cited

FOREIGN PATENT DOCUMENTS

| | | |
|---|---|---|
| CL | 2018003701 | 4/2019 |
| CL | 2018003697 | 5/2019 |
| CL | 2019001744 | 10/2019 |
| CL | 2019002919 | 1/2020 |
| CL | 2020002511 | 9/2020 |
| CN | 1344256 | 4/2002 |
| CN | 101891895 | 11/2010 |
| CN | 101910158 | 12/2010 |
| CN | 101993415 | 3/2011 |
| CN | 103933036 | 7/2014 |
| CN | 104045552 | 9/2014 |
| CN | 104211726 | 12/2014 |
| CN | 105164121 | 12/2015 |
| CN | 105705489 | 6/2016 |
| EP | 0361069 | 4/1990 |
| EP | 0644460 | 3/1995 |
| EP | 1505068 | 2/2005 |
| EP | 1644370 | 4/2006 |
| EP | 1942105 | 7/2008 |
| EP | 2233474 | 9/2010 |
| EP | 2402345 | 1/2012 |
| EP | 2871179 | 5/2015 |
| EP | 2824099 | 1/2018 |
| FR | 1425700 | 1/1966 |
| JP | H 10316853 | 12/1998 |
| JP | 2000128986 | 5/2000 |
| JP | 2000128987 | 5/2000 |
| JP | 2000212281 | 8/2000 |
| JP | 2001114893 | 4/2001 |
| JP | 2001163975 | 6/2001 |
| JP | 3461397 | 10/2003 |
| JP | 2003287634 | 10/2003 |
| JP | 2004059761 | 2/2004 |
| JP | 2004091369 | 3/2004 |
| JP | 2004294556 | 10/2004 |
| JP | 2005002330 | 1/2005 |
| JP | 2005248082 | 9/2005 |
| JP | 2005290301 | 10/2005 |
| JP | 2006-290883 | 10/2006 |
| JP | 2008218327 | 9/2008 |
| JP | 2010202530 | 9/2010 |
| JP | 2010540452 | 12/2010 |
| JP | 2013084945 | 5/2013 |
| JP | 2014520866 | 8/2014 |
| JP | 2014532066 | 12/2014 |
| JP | 2015155397 | 8/2015 |
| JP | 2015193612 | 11/2015 |
| JP | 2016135778 | 7/2016 |
| JP | 2016532710 | 10/2016 |
| JP | 2019523231 | 8/2019 |
| JP | 2019530732 | 10/2019 |
| JP | 2020504737 | 2/2020 |
| JP | 2020504739 | 2/2020 |
| JP | 2020514271 | 5/2020 |
| JP | 6911031 | 7/2021 |
| KR | 1715090 | 3/2015 |
| KR | 1717601 | 12/2015 |
| KR | 1653560 | 2/2016 |
| TW | 103143948 | 12/2014 |
| TW | 201625527 | 7/2016 |
| WO | WO 98/27108 | 6/1998 |
| WO | WO 1999/018096 | 4/1999 |
| WO | WO 99/44992 A1 | 9/1999 |
| WO | WO 00/35886 | 6/2000 |
| WO | WO 01/07409 | 2/2001 |
| WO | WO 2001/047883 | 7/2001 |
| WO | WO 01/74815 | 10/2001 |
| WO | WO 2002/000196 | 1/2002 |
| WO | WO 02/14321 | 2/2002 |
| WO | WO 02/48147 | 6/2002 |
| WO | WO 02/066477 | 8/2002 |
| WO | WO 02/071827 | 9/2002 |
| WO | WO 02/078700 | 10/2002 |
| WO | WO 02/083672 | 10/2002 |
| WO | WO 02/088124 | 11/2002 |
| WO | WO 03/022845 | 3/2003 |
| WO | WO 03/030901 | 4/2003 |
| WO | WO 03/031587 | 4/2003 |
| WO | WO 03/042402 | 5/2003 |
| WO | WO 2004/006906 | 1/2004 |
| WO | WO 2004/033454 | 4/2004 |
| WO | WO 2004/035588 | 4/2004 |
| WO | WO 2004/085385 | 10/2004 |
| WO | WO 2004/089940 | 10/2004 |
| WO | WO 2005/000833 | 1/2005 |
| WO | WO 2005/005429 | 1/2005 |
| WO | WO 2005/014543 | 2/2005 |
| WO | WO 2005/014599 | 2/2005 |
| WO | WO 2005/023761 | 3/2005 |
| WO | WO 2005/034869 | 4/2005 |
| WO | WO 2005/047290 | 5/2005 |
| WO | WO 2005/063710 | 7/2005 |
| WO | WO 2005/077948 | 8/2005 |
| WO | WO 2005/079802 | 9/2005 |
| WO | WO 2005/080316 | 9/2005 |
| WO | WO 2005/086808 | 9/2005 |
| WO | WO 2005/086904 | 9/2005 |
| WO | WO 2005/097751 | 10/2005 |
| WO | WO 2005/103022 | 11/2005 |
| WO | WO 2005/105798 | 11/2005 |
| WO | WO 2006/034317 | 3/2006 |
| WO | WO 2006/034337 | 3/2006 |
| WO | WO 2006/050803 | 5/2006 |
| WO | WO 2006/053121 | 5/2006 |
| WO | WO 2006/094235 | 9/2006 |
| WO | WO 2006/099075 | 9/2006 |
| WO | WO 2006/125101 | 11/2006 |
| WO | WO 2007/004954 | 1/2007 |
| WO | WO 2007/034282 | 3/2007 |
| WO | WO 2007/038314 | 4/2007 |
| WO | WO 2007/061764 | 5/2007 |
| WO | WO 2007/067711 | 6/2007 |
| WO | WO 2007/069565 | 6/2007 |
| WO | WO 2007/096764 | 8/2007 |
| WO | WO 2007/113226 | 10/2007 |
| WO | WO 2007/146712 | 12/2007 |
| WO | WO 2008/011560 | 1/2008 |
| WO | WO 2008/021745 | 2/2008 |
| WO | WO 2008/027812 | 3/2008 |
| WO | WO 2008/032171 | 3/2008 |
| WO | WO 2008/033854 | 3/2008 |
| WO | WO 2008/033857 | 3/2008 |
| WO | WO 2008/033858 | 3/2008 |
| WO | WO 2008/057254 | 5/2008 |
| WO | WO 2008/062182 | 5/2008 |
| WO | WO 2008/064317 | 5/2008 |
| WO | WO 2008/064318 | 5/2008 |
| WO | WO 2008/071944 | 6/2008 |
| WO | WO 2008/079965 | 7/2008 |
| WO | WO 2008/104077 | 9/2008 |
| WO | WO 2008/104278 | 9/2008 |
| WO | WO 2008/104279 | 9/2008 |
| WO | WO 2008/111299 | 9/2008 |
| WO | WO 2008/114002 | 9/2008 |
| WO | WO 2008/118122 | 10/2008 |
| WO | WO 2008/133274 | 11/2008 |
| WO | WO 2008/134553 | 11/2008 |
| WO | WO 2008/141249 | 11/2008 |
| WO | WO 2008/156712 | 12/2008 |
| WO | WO 2009/027733 | 3/2009 |
| WO | WO 2009/038759 | 3/2009 |
| WO | WO 2009/039397 | 3/2009 |
| WO | WO 2009/059162 | 5/2009 |
| WO | WO 2009/062059 | 5/2009 |
| WO | WO 2009/075830 | 6/2009 |
| WO | WO 2009/077197 | 6/2009 |
| WO | WO 2009/079683 | 7/2009 |
| WO | WO 2009/106539 | 9/2009 |
| WO | WO 2009/106597 | 9/2009 |
| WO | WO 2009/123986 | 10/2009 |
| WO | WO 2009/139576 | 11/2009 |
| WO | WO 2009/143156 | 11/2009 |
| WO | WO 2009/146358 | 12/2009 |
| WO | WO 2010/011837 | 1/2010 |

(56) References Cited

FOREIGN PATENT DOCUMENTS

| | | |
|---|---|---|
| WO | WO 2010/029950 | 3/2010 |
| WO | WO 2010/036959 | 4/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/080474 | 7/2010 |
| WO | WO 2010/089411 | 8/2010 |
| WO | WO 2010/104306 | 9/2010 |
| WO | WO 2010/115736 | 10/2010 |
| WO | WO 2010/119264 | 10/2010 |
| WO | WO 2010/130034 | 11/2010 |
| WO | WO 2011/002635 | 1/2011 |
| WO | WO 2011/008709 | 1/2011 |
| WO | WO 2011/018170 | 2/2011 |
| WO | WO 2011/044181 | 4/2011 |
| WO | WO 2011/047129 | 4/2011 |
| WO | WO 2011/047319 | 4/2011 |
| WO | WO 2011/050245 | 4/2011 |
| WO | WO 2009/096202 | 5/2011 |
| WO | WO 2011/066342 | 6/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2011/159877 | 12/2011 |
| WO | WO 2011/161699 | 12/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |
| WO | WO 2012/166951 | 12/2012 |
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/121085 | 8/2014 |
| WO | WO 2014/133046 | 9/2014 |
| WO | WO 2014/138484 | 9/2014 |
| WO | WO 2014/138791 | 9/2014 |
| WO | WO 2014/151634 | 9/2014 |
| WO | WO 2014/152536 | 9/2014 |
| WO | WO 2014/159959 | 10/2014 |
| WO | WO 2014/181287 | 11/2014 |
| WO | WO 2014/186035 | 11/2014 |
| WO | WO 2014/210255 | 12/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086498 | 6/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/175678 | 11/2015 |
| WO | WO 2015/197028 | 12/2015 |
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2017/223239 | 12/2017 |
| WO | WO 2018/013789 | 1/2018 |
| WO | WO 2018/026971 | 2/2018 |
| WO | WO 2018/044783 | 3/2018 |
| WO | WO 2018/045084 | 3/2018 |
| WO | WO 2016/057500 | 4/2018 |
| WO | WO 2018/116259 | 6/2018 |
| WO | WO 2018/119036 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/195121 | 10/2018 |
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/191707 | 10/2019 |
| WO | WO 2019/192506 | 10/2019 |
| WO | WO 2019/204609 | 10/2019 |
| WO | WO 2020/086556 | 4/2020 |
| WO | WO 2020/088357 | 5/2020 |
| WO | WO 2020/156323 | 8/2020 |
| WO | WO 2021/030162 | 2/2021 |

OTHER PUBLICATIONS

Amaya et al., "Synthesis of three-dimensionally arranged bis-biphenol ligand on hexaaryl benzene scaffold and its application for cross-pinacol coupling reaction," Tetrahedron Letters, 2011, 52(35):4567-4569.

Anyika et al., "Point-to-Axial Chirality Transfer—A New Probe for "Sensing" the Absolute Configurations of Monoamines," J Am Chem Soc., 2014, 136(2):550-553.

Arkin et al., "Small-Molecule Inhibitors of Protein-Protein Interactions: Progressing toward the Reality," Chemistry & Biology, Sep. 2014, 21:1102-1114.

Arkin et al., "Small-Molecule Inhibitors of Protein-Protein Interactions: Progressing Towards the Dream," Nature Reviews, Apr. 2004, 3:301-317.

Artz et al., "Host-guest complexation. 28. Hemispherands with four self-organizing units," J Am Chem Soc., 1984, 106(7):2160-2171.

(56) References Cited

OTHER PUBLICATIONS

Atzrodt et al., "The Renaissance of H/D Exchange," Angew Chem Int Ed., 2007, 7744-7765.
Australian Office Action in Australian Application No. 2016358100, dated May 8, 2020, 5 pages.
Barakat, "Do We Need Small Molecule Inhibitors for the Immune Checkpoints?" J. Pharma. Care Health Sys., 2014, 1(4): 1000e119.
Barber et al., "Restoring function in exhausted CD8 T cells during chronic viral infection," Nature, Feb. 2006, 439:682-687.
Bentley et al., "Antenna Biphenols: Development of Extended Wavelength Chiroptical Reporters," J Org Chem., 2016, 81(3): 1185-1191.
Berg, "Modulation of Protein—Protein Interactions with Small Organic Molecules," Angew. Chem. Int. Ed., 2003, 42:2462-2481.
Berge et al., "Pharmaceutical Salts," J. Pharm. Sci., Jan. 1977, 66(1):1-19.
Blank et al., "PD-L1/B7H-1 Inhibits the Effector Phase of Tumor Rejection by T Cell Receptor (TCR) Transgenic CD8+ T Cells," Cancer Res., Feb. 2004, 64(3): 1140-5.
Blom et al., "Optimizing Preparative LC-MS Configurations and Methods for Parallel Synthesis Purification", J. Combi. Chem., 2003, 5:670-83.
Blom et al., "Preparative LC-MS Purification: Improved Compound Specific Method Optimization", J. Combi. Chem., Nov. 2004, 6:874-883.
Blom, "Two-Pump at Column Dilution Configuration for Preparative LC-MS", K. Blom, J. Combi. Chem., 2002, 4:295-301.
Brazilian Office Action in Brazilian Application No. BR112018012756-6, dated Jan. 5, 2021, 6 pages.
Bross et al., "Radiation damage to 2-(2'-hydroxyphenyl)benzothiazoles," Radiation Physics and Chemistry, Jul. 1992, 41:379-387.
Buisman et al., "Chiral Cooperativity in Diastereomeric Diphosphite Ligands: Effects on the Rhodium-Catalyzed Enantioselective Hydroformylation of Styrene," Organometallics, 1997, 16(13):2929-2939.
Carter et al., "PD-1:PD-L inhibitory pathway affects both CD4+ and CD8+ T cells and is overcome by IL-2," Eur. J. Immunol., 2002, 32(3):634-643.
Chang et al., "Blocking of the PD-1/PD-L1 Interaction by a d-Peptide Antagonist for Cancer Immunotherapy," Angew. Chem. Int. Ed., 2015, 127(40): 11926-11930.
Chang et al., "Blocking of the PD-1/PD-L1 Interaction by a d-Peptide Antagonist for Cancer Immunotherapy" Angew. Chem. Int. Ed., 2015, 26 pages; Supporting Information for 127(40):11926-11930.
Chen et al., "Anti-PD-1/PD-L1 therapy of human cancer: past, present, and future," J. Clin. Invest., Sep. 2015, 125(9):3384-3391.
Cheng et al., "Synthetic connections to the aromatic directed metalation reaction. Iterative ortho metalation-cross coupling tactics for the construction of polyphenyls," Tetrahedron Letters, 1978, 28(43):5097-5098.
Cheng et al., "Recent Advances in Small Molecule Based Cancer Immunotherapy," Eur J Med Chem., 2018, 157:582-598.
Cheng et al., "Structure and Interactions of the Human Programmed Cell Death 1 Receptor," J. Bio. Chem., Apr. 2013, 288(17):11771-11785.
Chilean Office Action in Chilean Application No. 201801685, dated Aug. 20, 2019, 18 pages.
Chilean Office Action in Chilean Application No. 201803701, dated Nov. 22, 2019, 18 page.
Chilean Office Action in Chilean Application No. 201901744, dated Apr. 14, 2020, 19 pages.
Chinese Search Report in Chinese Application No. 201780049752.9, dated Dec. 28, 2020, 5 pages.
Clayden et al., "Conformational Preference and Remote (1,10) Stereocontrol in Biphenyl-2,2'-dicarboxamides," Org. Lett., 2001, 3(26):4133-4136.
Colombian Office Action in Colombian Application No. NC2019/0000386, dated Sep. 25, 2020, 18 pages.
Cram et al., "Host-guest complexation. 32. Spherands composed of cyclic urea and anisyl units," J Am Chem Soc., 1984, 106(23):7150-7167.
Cram et al., "Host-guest complexation. 29. Expanded hemispherands," J Am Chem Soc., 1984, 106(11):6386-3292.
Cram et al., "Host-guest complexation. 26. Cavitands composed of fluorobenzene units bonded in their 2,6-positions to form macrocycles," J Am Chem Soc., 1984, 106(3):695-701.
Cram et al., "Spherand hosts containing cyclic urea units," J Am Chem Soc., 1982, 104(24):6828-6830.
Curis, "Overview and Path for Growth," Aurigene Strategic Collaboration, Jan. 21, 2015, 13 slides.
Database Accession No. 1590700-72-3 abstract, Apr. 27, 2014, 1 page.
Database Accession No. 1581556-71-9 abstract, Apr. 8, 2014, 1 page.
Database Accession No. 1580823-55-7 abstract, Apr. 6, 2014, 1 page.
Database Accession No. 1568738-04-4 abstract, Mar. 14, 2014, 1 page.
Database accession No. 1478989-52-4 abstract, Nov. 22, 2013, 1 page.
Database accession No. 2013:447446 abstract, 2013, 1 page.
De Lucca et al., "Small Molecule Reversible Inhibitors of Bruton's Tyrosine Kinase (BTK): Structure-Activity Relationships Leading to the Identification of 7-(2-Hydroxypropan-2-yl)-4-[2-methyl-3-(4-oxo-3,4-dihydroquinazolin-3-yl)phenyl]-9H-carbazole-1-carboxamide (BMS-935177)," Journal of Medicinal Chemistry, 2016, 59(17):7915-7935.
Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Differding Consulting s.p.r.l. (Belgium), Feb. 26, 2014, 12 pages.
Dhanunjayarao et al., "Synthesis and Optical Properties of Salicylaldimine-Based Diboron Complexes, " Eur J Inorg Chem., 2014, 3:539-545.
Dolan et al., "PD-1 Pathway Inhibitors: Changing the Landscape of Cancer Immunotherapy," Cancer Control, Jul. 2014, 21(3):231-237.
Domling et al., "Programmed Death-1: Therapeutic Success after More than 100 Years of Cancer Immunotherapy," Angew. Chem. Int. Ed., 2014, 53:2283-2288.
Ecuador Opposition in Ecuador Application No. SENADI-2019-3773, dated Oct. 10, 2019, 29 pages.
Escarcega-Bobadilla et al., "A Recyclable Trinuclear Bifunctional Catalyst Derived from a Tetraoxo Bis-Zn(salphen) Metalloligand," Chemistry—A European Journal., 2013, 19(8):2641-2648.
Escarcega-Bobadilla et al., "Metal-directed assembly of chiral bis-Zn(II) Schiff base structures," Dalton Transactions, 2012, 41(32):9766-9772.
Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.
Eurasian Office Action in Eurasian Application No. 201990074/28, dated Oct. 3, 2019, 5 pages.
European Communication in European Application No. 16805690.1, dated Jul. 10, 2018, 6 pages.
European Communication in European Application No. 16805690.1, dated Jan. 22, 2020, 5 pages.
European Communication in European Application No. 17743174.9, dated Jan. 31, 2020, 5 pages.
European Communication in European Application No. 16805690.1, dated Nov. 5, 2020, 4 pages.
Fabris et al., "Central to Axial Transfer of Chirality in Menthone or Camphor-Derived 2,2'-Biphenols," J Org Chem., 1997, 62(21):7156-7164.
FDA Report, "22 Case Studies Where Phase 2 and Phase 3 Trials Had Divergent Results," U.S. Food and Drug Administration, Jan. 2017, 44 pages.
Francisco et al., "The PD-1 Pathway in Tolerance and Autoimmunity," Immunol. Rev., Jul. 2010, 236:219-242.

(56) References Cited

OTHER PUBLICATIONS

Freeman et al, "Engagement of the Pd-1 Immunoinhibitory Receptor by a Novel B7 Family Member Leads to Negative Regulation of Lymphocyte Activation," J. Exp. Med., Oct. 2000, 192(7):1027-34.
Freeman, "Structures of PD-1 with its ligands: Sideways and dancing cheek to cheek," PNAS, Jul. 2008, 105(30):10275-10276.
Freindorf, M., "Vibronic couplings in an excited state of hydrogen bond dimeric systems," Acta Physica Polonica, 1990, A78(6):825-839.
Gong et al., "Rhodium(I)-catalyzed regiospecific dimerization of aromatic acids: two direct C—H bond activations in water," Angewandte Chemie, 2015, 54(19):5718-5721.
Goswami et al., "A turn on ESIPT probe for rapid and ratiometric fluorogenic detection of homocysteine and cysteine in water with live cell-imaging," Tetrahedron Letters, 2014, 55(2):490-494.
Gould et al. "Salt selection for basic drugs," Int J Pharma., 1986, 33(1-3):201-217.
Green et al., "Synthesis and investigation of the configurational stability of some dimethylammonium borate salts," J. Chem. Soc., Perkin Trans. 1, 2000, 24:4403-4408.
Greenwald et al, "The B7 Family Revisited," Annu. Rev. Immunol., 2005, 23:515-548.
Han et al., "Synthesis of binuclear phenoxyimino organoaluminum complexes and their use as the catalyst precursors for efficient ring-opening polymerisation of E-caprolactone," Dalton Transactions, 2013, 41:12346-12353.
Helgeson et al., "Host-guest complexation. 66. 18-Membered-ring spherands containing five anisyl groups," J Am Chem Soc., 1993, 1115(24):11506-11511.
Hilfiker "Relevance of Solid-state Properties for Pharmaceutical Products," Polymorphism in the Pharmaceutical Industry, Jan. 1, 2006, pp. 1-19.
Hu et al., "Syntheses and Ethylene Polymerization Behavior of Supported Salicylaldimine-Based Neutral Nickel(II) Catalysts," Organometallics, 2007, 26(10):2609-2615.
Hu et al., "Synthesis and Ethylene Polymerization Activity of a Novel, Highly Active Single-Component Binuclear Neutral Nickel(II) Catalyst," Organometallics, 2005, 24(11):2628-2632.
Hu et al., "Novel highly active binuclear neutral nickel and palladium complexes as precatalysts for norbornene polymerization," Journal of Molecular Catalysis A: Chemical 253, 2006, 155-164.
Huang et al, "The prognostic significance of PD-L1 in bladder cancer," Oncol. Rep., 2015, 33:3075-3084.
Huddle et al., "Reactions of alkyl-lithium compounds with aryl halides ," J Chem Soc., Perkin I, 1980, 12:2617-2625.
HuGEMM™ and HuCELL™ Models, "FactSheet," CrownBio, Oct. 2016, 8 pages.
Indian Office Action with Indian Application No. 201817026809, dated Apr. 29, 2020, 6 pages.
Indian Office Action with Indian Application No. 201917001998, dated Nov. 24, 2020, 7 pages.
Indian Office Action with Indian Application No. 201917028273, dated Feb. 15, 2021, 5 pages.
International Preliminary Report on Patentability in International Application No. PCT/US2016/057487, dated May 3, 2018, 7 pages.
International Preliminary Report on Patentability in International Application No. PCT/US2016/062730, dated May 31, 2018, 7 pages.
International Preliminary Report on Patentability in International Application No. PCT/US2016/067155, dated Jun. 19, 2018, 10 pages.
International Preliminary Report on Patentability in International Application No. PCT/US2016/067925, dated Jun. 26, 2018, 8 pages.
International Preliminary Report on Patentability in International Application No. PCT/US2017/031242, dated Nov. 6, 2018, 7 pages.
International Preliminary Report on Patentability in International Application No. PCT/US2017/034173, dated Nov. 27, 2018, 8 pages.
International Preliminary Report on Patentability in International Application No. PCT/US2017/038120, dated Dec. 25, 2018, 6 pages.
International Preliminary Report on Patentability in International Application No. PCT/US2017/041899, dated Jan. 15, 2019, 7 pages.
International Preliminary Report on Patentability in International Application No. PCT/US2017/048880, dated Mar. 5, 2019, 9 pages.
International Preliminary Report on Patentability in International Application No. PCT/US2017/067904, dated Jun. 25, 2019, 7 pages.
International Preliminary Report on Patentability in International Application No. PCT/US2017/067951, dated Jun. 25, 2019, 8 pages.
International Preliminary Report on Patentability in International Application No. PCT/US2017/067880, dated Jun. 25, 2019, 7 pages.
International Preliminary Report on Patentability in International Application No. PCT/US2017/067984, dated Jun. 25, 2019, 7 pages.
International Preliminary Report on Patentability in International Application No. PCT/US2017/067946, dated Jun. 25, 2019, 9 pages.
International Preliminary Report on Patentability in International Application No. PCT/US2017/067886, dated Jun. 25, 2019, 9 pages.
International Preliminary Report on Patentability in International Application No. PCT/US2019/025036, dated Oct. 15, 2020, 7 pages.
International Preliminary Report on Patentability in International Application No. PCT/US2019/031728, dated Nov. 17, 2020, 7 pages.
International Search Report and Written Opinion in International Application No. PCT/US2016/057487, dated Dec. 8, 2016, 11 pages.
International Search Report and Written Opinion in International Application No. PCT/US2016/062730, dated Feb. 9, 2017, 12 pages.
International Search Report and Written Opinion in International Application No. PCT/US2016/067925, dated Mar. 27, 2017, 13 pages.
International Search Report and Written Opinion in International Application No. PCT/US2016/067155, dated Apr. 24, 2017, 26 pages.
International Search Report and Written Opinion in International Application No. PCT/US2017/031242, dated Jun. 20, 2017, 22 pages.
International Search Report and Written Opinion in International Application No. PCT/US2017/034173, dated Aug. 8, 2017, 15 pages.
International Search Report and Written Opinion in International Application No. PCT/US2017/041899, dated Sep. 5, 2017, 12 pages.
International Search Report and Written Opinion in International Application No. PCT/US2017/038120, dated Aug. 1, 2017, 14 pages.
International Search Report and Written Opinion in International Application No. PCT/US2017/067904, dated Mar. 22, 2018, 14 pages.
International Search Report and Written Opinion in International Application No. PCT/US2017/067880, dated Mar. 21, 2018, 13 pages.
International Search Report and Written Opinion in International Application No. PCT/US2017/067984, dated Mar. 22, 2018, 14 pages.
International Search Report and Written Opinion in International Application No. PCT/US2017/067886, dated Mar. 23, 2018, 24 pages.
International Search Report and Written Opinion in International Application No. PCT/US2017/067946, dated May 22, 2018, 16 Pages.
International Search Report and Written Opinion in International Application No. PCT/US2017/067951, dated Mar. 27, 2018, 15 pages.

(56) References Cited

OTHER PUBLICATIONS

International Search Report and Written Opinion in International Application No. PCT/US2017/048880, dated Oct. 23, 2017, 15 pages.
International Search Report and Written Opinion in International Application No. PCT/US2019/031728, dated Jun. 25, 2019, 12 pages.
International Search Report and Written Opinion in International Application No. PCT/US2019/025036, dated Jul. 3, 2019, 12 pages.
International Search Report and Written Opinion in International Application No. PCT/US2020/045311, dated Oct. 2, 2020, 14 pages.
International Search Report in International Application No. PCT/US2020/053190, dated Jan. 29, 2021, 13 pages.
International Search Report and Written Opinion in International Application No. PCT/US2020/059817, dated Mar. 29, 2021, 19 pages.
Israeli Office Action in Israeli Application No. 259,406, dated Mar. 11, 2020, 10 pages.
Israeli Office Action in Israeli Application No. 260,166, dated Jun. 2, 2020, 13 pages.
Iwai et al, "Involvement of PD-L1 on tumor cells in the escape from host immune system and tumor immunotherapy by PD-L1 blockade," PNAS, Sep. 2002, 99(19): 12293-12297.
Japanese Office Action in Japanese Application No. 2018526213, dated Oct. 13, 2020, 10 pages.
Jiang et al., "Self-immobilizing binuclear neutral nickel catalyst for ethylene polymerization: Synthesis and catalytic studies," J Mol Cat., 2013, 380:139-143.
Kayal et al., "3,3'-Bis(triphenylsilyl)biphenoxide as a Sterically Hindered Ligand on Fe(II), Fe(III), and Cr(II)," Inorg Chem., 2002, 41(2):321-330.
Keir et al., "PD-1 and Its Ligands in Tolerance and Immunity," Annu. Rev. Immunol., 2008, 26:677-704.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Koch et al., "Nucleophilic reactions of pyridines and imidazoles with vinyl and aromatic halides," J Org Chem., 1993, 58(6): 1409-1414.
Komiyama et al, "IL-17 Plays an Important Role in the Development of Experimental Autoimmune Encephalomyelitis," J. Immunol., Jul. 2006, 177:566-73.
Latchman et al, "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30): 10483-10488.
Legon'kova et al., "Interaction of o,o-dihalo o'-hydroxy azo compounds with metallic copper. II. Preparation of oligomeric azo compounds from monoazo compounds," Mosk Khim-Tekhnol Inst im Mendeleeva., 1968, 11(11):1281-1284 Machine Translation.
Legon'kova et al., "Interaction of o,o-dihalogeno o-hydroxy azo compounds with metallic copper," Trudy Instituta—Moskovskii Khimiko-Tekhnologicheskii Institut imeni D. I. Mendeleeva, 1965, 48:120-125 Machine Translation.
Lehtonen et al., "Comparison of quaternary methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Li et al., "A Mini-Review for Cancer Immunotherapy: Molecular Understanding of PD-1/PD-L1 Pathway & Translational Blockade of Immune Checkpoints," Int. J. Mol. Soc., 2016, 17:1151, 22 pages.
Li et al., "Analysis of Receptor Tyrosine Kinase Internalization Using Flow Cytometry," Methods Mol. Biol., 2008, 457:305-317.
Li et al., "Asymmetric Alternating Copolymerization of Meso-epoxides and Cyclic Anhydrides: Efficient Access to Enantiopure Polyesters," J. Am. Chem. Soc., 2016, 138(36): 11493-11496.
Li et al., "A 3D Mesomeric Supramolecular Structure of a Cu(II) Coordination Polymer with 1,1'-Biphenyl-2,2',3,3'-tetracarboxylic Acid and 5,5'-Dimethyl-2,2'-bipyridine Ligands," J Inorg and Organomet Poly Mat., 2012, 22(6):1320-1324.
Li et al., "Discovery of peptide inhibitors targeting human programmed death 1 (PD-1) receptor," Oncotarget, Aug. 2016, 7(40): 64967-64976.
Lin et al., "The PD-1/PD-L1 complex resembles the antigen-binding Fv domains of antibodies and T cell receptors," PNAS, Feb. 2008, 105(8):3011-3016.
Lipson et al., "From Discovery to Development: Blocking PD-1 and its Ligands," The Melanoma Letter, A Publication of The Skin Cancer Foundation, vol. 31, Summer 2013, 6 pages.
Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44): 11594-11598.
Liu et al., "Development of amino- and dimethylcarbamate-substituted resorcinol as programmed cell death-1 (PD-1) inhibitor," Eur J Pharm Sci, 2016, 88:50-58.
Mahoney et al., "The Next Immune-Checkpoint Inhibitors:PD-1/PD-L1 Blockade in Melanoma," Clin. Therapeutics, Nov. 2015, 37(4):761-782.
Maier et al., "Effects of the stationary phase and the solvent on the stereodynamics of biphep ligands quantified by dynamic three-column HPLC," Angewante Chemie, 2012, 51(12):2985-2988.
Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.
Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.
Mexican Office Action in Mexican Application No. MX/a/2018/016273, dated Mar. 26, 2021, 7 pages.
Miyaura and Suzuki, "Palladium-Catalyzed Cross-Coupling Reactions of Organoboron Compounds," Chem Rev., 1995, 95:2457-2483.
Mochida et al., "Rhodium-Catalyzed Regioselective Olefination Directed by a Carboxylic Group," J Org Chem, 2011, 76(9):3024-3033.
Moneta et al., "Boron templated synthesis of macrocyclic hosts containing convergent hydroxy or methoxy groups," Bulletin de la Societe Chimique de France, 1988, 6:995-1004 (English Abstract).
Nallasivam et al., "Development of Unimolecular Tetrakis(piperidin-4-ol) as a Ligand for Suzuki-Miyaura Cross-Coupling Reactions: Synthesis of Incrustoporin and Preclamol," 2015, Eur J Org Chem., 2015(16):3558-3567.
Nero et al., "Oncogenic protein interfaces: small molecules, big challenges," Nature Reviews, Apr. 2014, 14:248-262.
Nishimura et al, "Autoimmune Dilated Cardiomyopathy in PD-1 Receptor-Deficient Mice," Science, Jan. 2001, 291:319-322.
Nishimura et al, "Development of Lupus-like Autoimmune Diseases by Disruption of the PD-1 Gene Encoding an ITIM Motif-Carrying Immunoreceptor," Immunity, Aug. 1999, 11:141-151.
Nishimura et al., "PD-1: an inhibitory immunoreceptor involved in peripheral tolerance," TRENDS in Immunology, May 2001, 22(5):265-268.
Nishino et al., "Copper-Mediated C—H/C—H Biaryl Coupling of Benzoic Acid Derivatives and 1,3-Azoles," Angew. Chem. Int. Ed., 2013, 52:4457-4461.
Normand et al., "Dinuclear vs. mononuclear complexes: accelerated, metal-dependent ring-opening polymerization of lactide," Chem. Commun., 2013, 49(99):11692-11694.
Okazaki and Honjo, "The PD-1-PD-L pathway in immunological tolerance," Trends Immunol., Apr. 2006, 4:195-201.
Okazaki et al., "A rheostat for immune responses: the unique properties of PD-1 and their advantages for clinical application," Nature Immunology, Dec. 2013, 14(12):1212-1218.
Paek et al.., "Facile syntheses and multi-orthofunctionalizations of tertiary benzamides," Bulletin of the Korean Chemical Society, 1993, 14(6): 732-739.

(56) References Cited

OTHER PUBLICATIONS

Paek et al., "Chiral host. Attempted synthesis using McMurray reaction as a final ring closure method," Bulletin of the Korean Chemical Society, 1989, 10(6):572-577.
Pardoll, "The blockade of immune checkpoints in cancer immunotherapy," Nature, Apr. 2012, 12:252-264.
Parry et al, "CTLA-4 and PD-1 Receptors Inhibit T-Cell Activation by Distinct Mechanisms," Mol. Cell. Biol., Nov. 2005, 25(21):9543-9553.
Parsons et al., "Directed ortho metalation reactions. Expedient synthesis of 3,3'-disubstituted 1,1'-bi-(2-phenols) (BIPOLS)," Tetrahedron Letters, 1994, 35(41):7537-7540.
Pascolutti et al., "Structure and Dynamics of PD-L1 and an Ultra-High-Affinity PD-1 Receptor Mutant," Structure, Oct. 2016, 24:1719-1728.
Paulini et al., "Orthogonal Multipolar Interactions in Structural Chemistry and Biology," Angew. Chem. Int. Ed., 2005, 44:1788-1805.
Pearson et al., "The formation of complexes between aza-derivatives of crown ethers and primary alkylammonium salts. Part 5. Chiral macrocyclic diamines," J. Chem. Soc., Perkin I, 1979, 12:3113-3126.
Pfeiffer et al., "Inner complex salts of the aldimine and azo series," Journal fuer Praktische Chemie, 1937, 149:217-296 Machine Translation.
Pierre et al., "Synthesis of a new macrobicyclic siderophoric host molecule with six converging phenolate groups," Angewandte Chemie, 1991, 103(1): 75-76 Machine Translation.
Postow et al, "Immune Checkpoint Blockade in Cancer Therapy," J. Clinical Oncology, Jun. 2015, 33(17): 1974-1982.
Press Release Archive, "Boehringer Ingelheim and Yale University collaborate to investigate novel immunotherapy targets across several therapeutic areas," Boehringer Ingelheim, Jan. 13, 2015, 2 pages.
Puehlhofer et al., "SASAPOS cascades of perfluorinated aromatic carboxylic acids: low-temperature decarboxylation triggered by electrostatic effects of polycationic ligand sets," Euro J of Org Chem., 2004, 5:1002-1007.
Punniyamurthy et al., "Enantiomerically pure bicyclo[3.3.1]nona-2,6-diene as the sole source of enantioselectivity in BIPHEP-Rh asymmetric hydrogenation," Chem Comm., 2008, 41:5092-5094.
Sabatier et al, "Prognostic and predictive value of PDL1 expression in breast cancer," Oncotarget, Mar. 2015, 6(7):5449-5464.
Sharpe et al, "The function of programmed cell death 1 and its ligands in regulating autoimmunity and infection," Nat. Immunol., Mar. 2007 8(3):239-245.
Sharpe et al., "The B7-CD28 Superfamily," Nature Reviews, Feb. 2002, 2:116-126.
Sharma et al., "Palladium-Catalyzed Decarboxylative Acylation of O-Phenyl Carbamates with Alpha-Oxocarboxylic Acids at Room Temperature," Advanced Synthesis & Catalysis, 2013, 355(4):667-672.
STN Search Report dated Apr. 14, 2016, 79 pages.
STN Search Report dated Apr. 29, 2016, 69 pages.
STN Search Report dated Aug. 30, 2016, 4 pages.
STN Search Report dated Jun. 6, 2016, 115 pages.
STN Search Report dated Sep. 2, 2016, 115 pages.
STN Search Report, dated May 1, 2016, 12 pages.
STN Search Report dated May 24, 2016, 92 pages.
STN Search Report dated Sep. 12, 2016, 4 pages.
STN Search Report dated Jun. 16, 2016, 8 pages.
STN Search Report dated Sep. 12, 2016, 17 pages.
STN Search Report dated Jul. 12, 2016, 4 pages.
STN Search Report dated Aug. 19, 2016, 23 pages.
STN Search Report dated Dec. 15, 2016, 4 pages.
STN Search Report dated Dec. 19, 2016, 11 pages.
STN Search Report dated Dec. 16, 2016, 25 pages.
STN Search Report dated Dec. 16, 2016, 4 pages.
STN Search Report dated Dec. 20, 2016, 117 pages.
STN Search Report dated Sep. 27, 2017, 4 pages.
STN Search Report dated Mar. 27, 2018, 4 pages.
STN Search Report dated Apr. 30, 2018, 8 pages.
Sorrell et al., "3,3'-Disubstituted 2,2'-biphenols. Synthesis of nonplanar, tetradentate chelating ligands," J Org Chem., 1985, 50(26):5765-5769.
Storz, "Intellectual property issues of immune checkpoint inhibitors," mAbs, Jan. 2016, 8(1):10-26.
Sumrit et al., "Aluminum complexes containing salicylbenzoxazole ligands and their application in the ring-opening polymerization of rac-lactide and ε-caprolactone," Dalton Transactions (2016), 45(22), 9250-9266.
Sun et al., "Studies on Synthesis and Properties of Some New Dibenzocyclobromonium," Chemical Journal of Chinse Universities, 1998, 19(12), 6 pages (English Abstract).
Taiwan Office Action in Taiwan Application No. 105133530, dated Oct. 15, 2020, 8 pages.
Taiwan Office Action in Taiwan Application No. 105141804, dated Nov. 9, 2020, 9 pages.
Taiwan Office Action in Taiwan Application No. 105137807, dated Nov. 12, 2020, 12 pages.
Tang et al., "Facile synthesis of enantioenriched phenol-sulfoxides and their aluminum complexes," Org Biomol Chem., 2016, 14(24):5580-5585.
Thiel et al., "Small-Molecule Stabilization of Protein-Protein Interactions: An Underestimated Concept in Drug Discovery?" Angew. Chem. Int. Ed., 2012, 51:2012-2018.
Tucker et al., "Host-guest complexation. 52. Bridged and chiral hemispherands," J Org Chem., 1989, 54(23):5460-5482.
Ukraine Office Action in Ukraine Application No. a 2019 00525, dated Jan. 14, 2021, 11 pages.
Unrau et al., "Directed ortho metalation. Suzuki cross coupling connections. Convenient regiospecific routes to functionalized m- and p-teraryls and m-quinquearyls," Tetrahedron Letters, 1992, 33(20):2773-2776.
Velcheti et al., "Programmed death-1/programmed death-1 ligand axis as a therapeutic target in oncology: current insights," Journal of Receptor Ligand and Channel Research, Dec. 2014, 8(23): 1-7.
Wang et al, "The prognostic value of PD-L1 expression for non-small cell lung cancer patients: A meta-analysis," Eur. J. Surg. Oncol., 2015, 41:450-456.
Wang et al., "A binuclear Zn(II)-Zn(II) complex from a 2-hydroxybenzohydrazide-derived Schiff base for selective detection of pyrophosphate," Dalton Transactions, Oct. 2014, 43(37): 14142-14146.
Wang et al., "Molecular Modeling and Functional Mapping of B7-H1 and B7-DC Uncouple Costimulatory Function from PD-1 Interaction," J. Exp. Med., Apr. 2013, 197(3): 1083-1091.
Wei et al., "Strength of PD-1 signaling differentially affects T-cell effector functions," PNAS, Apr. 2013, E2480-E2489.
Weinmann, "Cancer Immunotherapy: Selected Targets and Small-Molecule Modulators," Chem. Med. Chem., 2016, 11:450-466.
Weiss et al., "Electrostatics and color: Massive electrostatic perturbation of chromophores by ion cluster ligands," J Am Chem Soc., 2007, 129(3):547-553.
Weiss et al., "Electrostatic activation of SNAr-reactivity by sulfonylonio substituents," Zeitschrift fuer Naturforschung, 2001, 56(12):1360-1368 English Abstract.
Weiss et al., "First-ever per(onio) substitution of benzene: the role of the counterion," Angewandte Chemie, 1995, 34(12):1319-1321.
Weiss et al., "Massive electrostatic effects on heteropolar C—C disconnections: Transforming a phenyl anion into a potent leaving group," Euro J Org Chem., 2005, 16:3530-3535.
Weiss et al., "Poly-onio substituted quinones as strong electron acceptors," Inst Org Chem., 1986, 98(10):925-926.
Weiss et al., "SASAPOS, not Sisyphus: highly efficient 20-step one-pot synthesis of a discrete organic-inorganic ion cluster with a porphyrin core," Angewandte Chemie International Edition, 2002, 41(20):3815-3817.
Weiss et al., "Syntheses and Reactions of Polycationically Substituted Azido- and Diazidobenzenes," Eur J Org Chem., Nov. 2007, 31:5270-5276.
Wells et al., "Reaching for high-hanging fruit in drug discovery at protein-protein interfaces," Nature, Dec. 2007, 450:1001-1009.

(56) References Cited

OTHER PUBLICATIONS

Wu et al., "Targeting the BACE1 Active Site Flap Leads to a Potent Inhibitor That Elicits Robust Brain αβ Reduction in Rodents," ACS Medicinal Chemistry Letters, 2016, 7(3):271-276.
Wuts et al., "Protective Groups in Organic Synthesis," 4th Ed., 2007, 1111 pages.
www.medscape.com' [online]. "The 'Family Business' Behind the Flurry of PD-1 Inhibitors," Sep. 10, 2014. [Retrieved on Jan. 29, 2015]. Retrieved from the Internet: URL<http://www.medscape.com/viewarticle/831448_print>. 3 pages.
Xiong et al., "Biaryl-Bridged Salalen Ligands and Their Application in Titanium-Catalyzed Asymmetric Epoxidation of Olefins with Aqueous H2O2," Eur J Org Chem., 2011, 23:4289-4292.
Xu et al., "Quantitative structure-activity relationship study on BTK inhibitors by modified multivariate adaptive regression spline and CoMSIA methods," SAR QSAR Environ Res., 2015, 26(4):279-300.
Xu et al., "Design, synthesis and biological evaluation of deuterated nintedanib for improving pharmacokinetic properties," J Label Compd RadioPharm., Jun. 15, 2015, 58(7):308-312.
Yin et al., "Strategies for Targeting Protein-Protein Interactions With Synthetic Agents," Angew. Chem. Int. Ed., 2005, 44:4130-4163.
Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.
Young et al., "Potent and selective Bruton's tyrosine kinase inhibitors: Discovery of GDC-0834," Bioorganic & Medicinal Chemistry Letters , 2015, 25(6): 1333-1337.
Zarganes-Tzitzikas, "Inhibitors of programmed cell death 1 (PD-1): a patent review (2010-2015)," Expert Opinion on Therapeutic Patents, Sep. 19, 2016, 26(9):973-977.
Zak et al., "Structural basis for small molecule targeting of the programmed death ligand 1 (PD-L1)," Oncotarget, 2016, 7(21):30323-30335.
Zak et al., "Structural basis for small molecule targeting of the programmed death ligand 1 (PD-L1)" Oncotarget, Apr. 2016, 19 pages; Supplemental Material for 2016, 7(21):30323-30335.
Zak et al., "Structure of the Complex of Human Programmed Death 1, PD-1, and Its Ligand PD-L1: with Supplemental Information," Structure, Dec. 2015, 23:2341-2348.
Zang et al., "Four 2D metal-organic networks incorporating Cd-cluster SUBs: hydrothermal synthesis, structures and photoluminescent properties," CrystEngComm, 2009, 11(1):122-129.
Zhan et al., "From monoclonal antibodies to small molecules: the development of inhibitors targeting the PD-1/PD-L1 pathway," Drug Discovery Today, Apr. 2016, 10 pages.
Zhang et al., "Electrospray mass spectrum of a per(onio)-substituted benzene: retention of Coulombic charge upon collisionally activated decomposition," J Am Soc. Mass. Spectrom., 1998, 9(1):15-20.
Zhang et al., "Non-symmetrical diarylcarboxylic acids via rhodium(I)-catalyzed regiospecific cross-dehydrogenation coupling of aromatic acids: twofold direct C-H bond activations in water," RSC Advances, 2016, 6(64):91617-91620.
Zhang et al., "Structural and Functional Analysis of the Costimulatory Receptor Programmed Death-1," Immunity, Mar. 2004, 20:337-347.
Zhang et al., "Biaryl-Based Macrocyclic and Polymeric Chiral (Salophen)Ni(II) Complexes: Synthesis and Spectroscopic Study," J Org Chem., 2001, 66(2): 481-487.
Zhao et al., "Design, synthesis and organocatalysis of 2,2'-biphenol-based prolinamide organocatalysts in the asymmetric direct aldol reaction in water," Synlett, 2013, 24(20): 2743-2747.
Argentina Office Action in Argentina Application No. 20170103634, dated Jan. 27, 2022, 7 pages.
Australian Notice of Allowance in Australian Application No. 2017382870, dated Mar. 15, 2022, 4 pages.
Azuma et al., "B7-H1 is a ubiquitous antiapoptotic receptor on cancer cells," BLOOD, Apr. 1, 2018, 111(7):3635-3643.
Bastin et al., "Salt Selection and Optimisation for Pharmaceutical New Chemical Entities," Org Proc Res Dev., dated Jan. 1, 2000, pp. 4(5):427-435.
Caira, "Crystalline Polymorphism of Organic Compounds," Topics in Current Chemistry, Jan. 1, 1998, 198:163-208.
Camara et al., "Multiple dermatofibromas: Dermoscopic patterns," Indian journal of dermatology, 2013, 58(3):243.
Cheng et al., "Cancer-associated fibroblasts induce PDL1+ neutrophils through the IL6-STAT3 pathway that foster immune suppression in hepatocellular carcinoma," Cell Death and Disease, 2018, 9:422.
Chilean Office Action in Chilean Application No. 2922-2020, dated Dec. 8, 2021, 21 pages.
Chinese Office Action in Chinese Application No. 201680077700.8, dated Jul. 2, 2021, 23 pages.
Dong et al., "Tumor-associated B7-H1 promotes T-cell apoptosis: a potential mechanism of immune evasion," Nature Medicine, Aug. 2002, 8(8):793-800.
European Communication in European Application No. 20202254.7, dated Apr. 1, 2022, 4 pages.
Gu et al., "Undo the brake of tumour immune tolerance with antibodies, peptide mimetics and small molecule compounds targeting PD-1/PD-L1 checkpoint at different locations for acceleration of cytotoxic immunity to cancer cells," Clinical and Experimental Pharmacology and Physiology, 2019, 46(2):105-115.
Highlights Prescribing Information, "KEYTRUDA," Revised Feb. 2019, 66 pages.
Highlights Prescribing Information, "OPDIVO," Revised Apr. 2019, 90 pages.
Huang et al., "Pharmacological treatment for keloids," Expert opinion on pharmacotherapy, 2013, 14(15):2087-2100.
Indian Office Action in Indian Application No. 202017053661, dated Jun. 3, 2022, 5 pages.
International Preliminary Report on Patentability in International Application No. PCT/US2020/045311, dated Feb. 17, 2022, 8 pages.
International Preliminary Report on Patentability in International Application No. PCT/US2020/053190, dated Apr. 5, 2022, 7 pages.
International Preliminary Report on Patentability in International Application No. PCT/US2020/059817, dated May 17, 2022, 12 pages.
International Search Report and Written Opinion in International Application No. PCT/US2021/058268, dated Apr. 21, 2022, 22 pages.
International Search Report and Written Opinion in International Application No. PCT/US2021/058334, dated Apr. 25, 2022, 23 pages.
International Search Report and Written Opinion in International Application No. PCT/US2021/058338, dated Feb. 9, 2022, 15 pages.
International Search Report and Written Opinion in International Application No. PCT/US2021/063965, dated Apr. 12, 2022, 20 pages.
Invitation to Pay Fee's in International Application No. PCT/US2021/058268, dated Jan. 31, 2022, 16 pages.
Invitation to Pay Fee's in International Application No. PCT/US2021/058334, dated Feb. 3, 2022, 12 pages.
Israeli Office Action in Israeli Application No. 287,267, dated Feb. 15, 2022, 4 pages.
Japanese Office Action in Japanese Application No. 2019-534122, dated Oct. 19, 2021, 10 pages.
Japanese Office Action in Japanese Application No. 2019-534195, dated Nov. 1, 2021, 8 pages.
Japanese Office Action in Japanese Application No. 2019-534196, dated Nov. 9, 2021, 8 pages.
Lexico.com, "Synonyms of Enhance," Oxford Dictionary, retrieved on Dec. 9, 2021, retrieved from URL <https://www.lexico.conn/synonynns/enhance>, 4 pages.
Mexican Office Action in Mexican Application No. MX/a/2018/007774, dated Apr. 8, 2021, 5 pages.
Mexican Office Action in Mexican Application No. MX/a/2018/016273, dated Mar. 26, 2021, 5 pages.
Qin et al., "The Diverse Function of PD-1/PD-L Pathway Beyond Cancer," Frontiers in Immunology, Oct. 2019, 10(2298): 1-16.

(56) References Cited

OTHER PUBLICATIONS

Reck et al., "Pembrolizumab versus Chemotherapy for PD-L1-Positive Non-Small-Cell Lung Cancer," N Engl J Med., Nov. 10, 2016, 375(19): 1823-1833.
Rowe et al., "Fumaric Acid" Handbook of pharmaceutical excipients, Jan. 1, 2009, pp. 276-277, 309-310, 393-396.
Stahl et al., "Handbook of Pharmaceutical Salts: Properties, Selection, and Use," Wiley, 2002, p. 329-350.
Suarez et al., "Inhibitors of TAM subfamily of tyrosine kinases: synthesis and biological evaluation," European Journal of Medicinal Chemistry, 2013, 61:2-25.
Sznol et al., "Antagonist Antibodies to PD-1 and B7-H1 (PD-L1) in the Treatment of Advanced Human Cancer," Clin Cancer Res., Mar. 1, 2013, 19(5): 1021-1034.
Vaddepally et al., "Review of Indications of FDA-Approved Immune Checkpoint Inhibitors per NCCN Guidelines with the Level of Evidence," Cancers, 2020, 12(3):738.
Yao et al., "PD-1 as an Immune Modulatory Receptor," Cancer J., 2014, 20(4):262-264.
Methot et al., Exploration of the internal cavity of histone deacetylase (H DAC) with selective HDAC1/HDAC2 inhibitors (SHIT-1:2). Bioorganic & Medicinal Chemistry Letters, 2008. 18. 973-978.
Otter et al., "The human papillomavirus as a common pathogen in oropharyngeal, anal and cervical cancers," Clin Oncol (R Coll Radiol), Feb. 2019, 31(2):81-90.
Pajouhesh et al., Medicinal Chemical Properties of Successful Central Nervous System Drugs. NeuroRx, 2005, 2, 541-553.
Rowe et al., "Fumaric Acid," Handbook of pharmaceutical excipients, Jan. 1, 2009, pp. 276-277, 318-321, 663-666.

\* cited by examiner

SALTS AND CRYSTALLINE FORMS OF A PD-1/PD-L1 INHIBITOR

The present application claims the benefit of U.S. Provisional Application No. 62/933,869, filed Nov. 11, 2019; and U.S. Provisional Application No. 63/022,131, filed May 8, 2020, each of which is incorporated herein by reference in its entirety.

FIELD OF THE INVENTION

This application relates to solid forms and salt forms of the PD-1/PD-L1 inhibitor 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis (ethane-2,1-diyl))bis(bicyclo[2.2.1]heptane-1-carboxylic acid), including processes of preparation thereof, where the compound is useful in the treatment of various diseases including infectious diseases and cancer.

BACKGROUND OF THE INVENTION

The immune system plays an important role in controlling and eradicating diseases such as cancer. However, cancer cells often develop strategies to evade or to suppress the immune system in order to favor their growth. One such mechanism is altering the expression of co-stimulatory and co-inhibitory molecules expressed on immune cells (Postow et al, J. Clinical Oncology 2015, 1-9). Blocking the signaling of an inhibitory immune checkpoint, such as PD-1, has proven to be a promising and effective treatment modality.

Programmed cell death-1 (PD-1), also known as CD279, is a cell surface receptor expressed on activated T cells, natural killer T cells, B cells, and macrophages (Greenwald et al, Annu. Rev. Immunol. 2005, 23:515-548; Okazaki and Honjo, Trends Immunol 2006, (4):195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, *Nat Immunol* 2007 8, 239-245; Postow et al, J. Clinical Oncol. 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is upregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS2002, 99(19):12293-7; Blank et al, Cancer Res 2004, 64(3):1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7):1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-κB and AP1 pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7):1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Together, these data support the development of a therapeutic approach to block the PD-1-mediated inhibitory signaling cascade in order to augment or "rescue" T cell response. Accordingly, there is a need for new compounds and salts that block PD-1/PD-L1 protein/protein interaction.

SUMMARY OF THE INVENTION

The present disclosure is directed to solid forms and salt forms of 4,4'-(((((2,2'-dichloro-[1,1'-biphenyl]-3,3'-diyl)bis (azanediyl))bis(carbonyl))bis(1-methyl-1,4,6,7-tetrahydro-5H-imidazo[4,5-c]pyridine-2,5-diyl))bis(ethane-2,1-diyl)) bis(bicyclo[2.2.1]heptane-1-carboxylic acid) (Compound 1, an inhibitor of inhibition of PD-1/PD-L1 interaction).

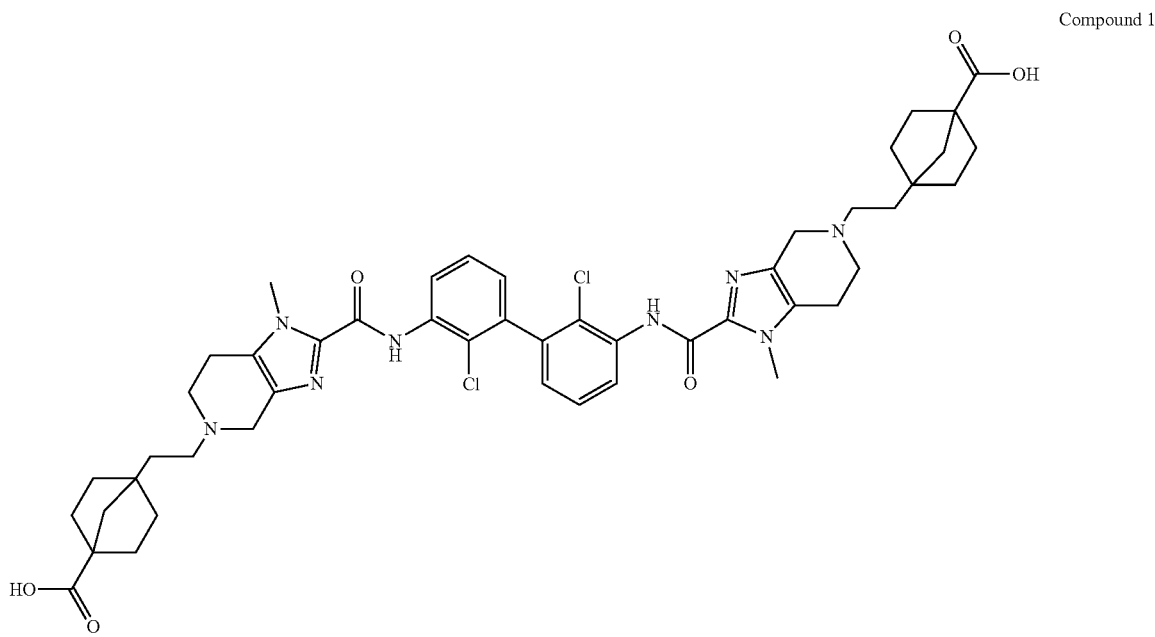 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCC13CCC(C(=O)O)(CC1)C3)C2]

The present disclosure is further directed to the crystalline free base, the di-sodium salt, the mono-hydrochloric acid salt, and the di-hydrochloric acid salt of Compound 1.

The present disclosure is further directed to crystalline forms of salts of Compound 1.

The present disclosure is further directed to pharmaceutical compositions comprising a solid forms or salt forms described herein and at least one pharmaceutically acceptable carrier or excipient. The present disclosure is further directed to solid dosage forms comprising the pharmaceutical compositions described herein.

The present disclosure is further directed to a method of inhibiting PD-1/PD-L1 interaction comprising administering to a patient the solid forms or salt forms described herein.

The present disclosure is further directed to treating a disease or disorder associated with inhibition of PD-1/PD-L1 interaction comprising administering to a patient the solid forms and salt forms described herein. The present disclosure is further directed to enhancing, stimulating and/or increasing the immune response in a patient comprising administering to a patient the solid forms and salt forms described herein.

The present disclosure also provides uses of the solid forms and salt forms described herein for manufacture of a medicament for use in any of the methods described herein.

The present disclosure also provides uses of the solid forms and salt forms described herein for use in any of the methods described herein.

The present disclosure further provides processes of preparing Compound 1, or a pharmaceutically acceptable salt thereof, comprising the steps detailed infra.

The present invention is further directed to processes for preparing the solid forms and salt forms described herein.

DETAILED DESCRIPTION

Figure 1:
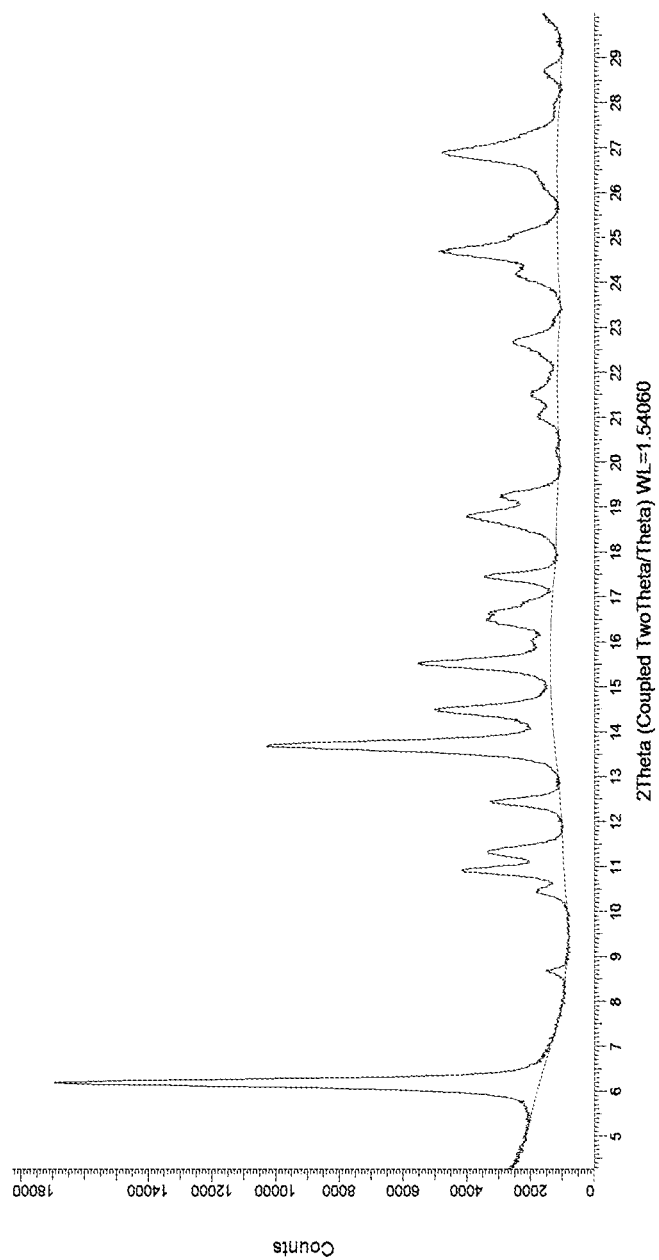
FIG. 1 shows an XRPD pattern of Compound 1 crystalline free base.

The present disclosure is directed to, inter alia, a solid form or salt form of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) (Compound 1).

In some embodiments, the solid form is a crystalline free base of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) (Compound 1 crystalline free base).

In some embodiments, the present disclosure provides salts of Compound 1.

In some embodiments, the salt is 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt (Compound 1 di-hydrochloric acid salt).

In some embodiments, the salt is 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) mono-hydrochloric acid salt (Compound 1 mono-hydrochloric acid salt).

In some embodiments, the salt is 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-sodium salt (Compound 1 di-sodium salt).

Different forms of the same substance have different bulk properties relating to, for example, hygroscopicity, solubility, stability, and the like. Forms with high melting points often have good thermodynamic stability which is advantageous in prolonging shelf-life drug formulations comprising the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage.

In some embodiments, the solid form of Compound 1 is crystalline. In some embodiments, a Compound 1 salt provided herein is crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

The different solid forms and salt forms thereof can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

In some embodiments, the term "about" means±10%. In some embodiments, the term "about" means±5%.

In some embodiments, the solid forms and salt forms are substantially isolated. By "substantially isolated" is meant that the solid form, salt form or crystalline form thereof is at least partially or substantially separated from the environment in which it was formed or detected. Partial separation can include, for example, a composition enriched in the solid forms and salt forms. Substantial separation can include compositions containing at least about 50%, at least about 60%, at least about 70%, at least about 80%, at least about 90%, at least about 95%, at least about 97%, or at least about 99% by weight of the solid forms and salt forms. Methods for isolating solid forms and salt forms thereof are routine in the art.

In some embodiments, the solid forms and salt forms described herein can be found together with other substances such as water and solvents (e.g., hydrates and solvates) or can be isolated.

The phrase "pharmaceutically acceptable" is employed herein to refer to those salts, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The salt forming reactions described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The expressions, "ambient temperature" and "room temperature" or "rt" as used herein, are understood in the art, and refer generally to a temperature, e.g., a reaction temperature, that is about the temperature of the room in which the salt forming reaction is carried out, for example, a temperature from about 20° C. to about 30° C.

The salt forming reactions described herein can be carried out in air or under an inert atmosphere. Typically, reactions containing reagents or products that are substantially reactive with air can be carried out using air-sensitive synthetic techniques that are well known to the skilled artisan.

Sodium Salts

In some embodiments, the salt of Compound 1 is 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-sodium salt (Compound 1 di-sodium salt).

Compound 1 di-sodium salt can be prepared by any suitable method for preparation of di-sodium addition salts. For example, Compound 1 can be reacted with sodium hydroxide (e.g., about 2.0 molar eq. or more) in a solvent and the resulting salt can be isolated by filtering the salt from solution. In certain embodiments, Compound 1 is reacted with about 2 to about 3 molar equivalents of sodium hydroxide. In certain embodiments, Compound 1 is reacted with about 2 to about 2.5 molar equivalents of sodium hydroxide. In certain embodiments, Compound 1 is reacted with about 2.2 molar equivalents of sodium hydroxide.

The solvent can comprise any solvent or mixture of solvents capable of at least partially dissolving Compound 1. In some embodiments, the solvent comprises an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent comprises acetone, tetrahydrofuran, dichloromethane, methanol, ethanol, 1-propanol, or isopropanol. In some embodiments, the solvent comprises acetone. In some embodiments, the solvent comprises water.

In some embodiments, the solvent is a mixture of acetone and water.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation and/or crystallization at a practical rate. In some embodiments, precipitation and/or crystallization is completed within about 1 to about 12 hours, but longer and shorter periods are possible depending on the choice of precipitation/crystallizing solvent and temperature. In some embodiments, the precipitation and/or crystallization is completed within about 1 hour.

The precipitation and/or crystallization of the di-sodium salt, in some embodiments, is carried out by filtering the salt from solution.

In some embodiments, Compound 1 di-sodium salt is amorphous. In some embodiments, Compound 1 di-sodium salt is crystalline. In some embodiments, Compound 1 di-sodium salt is a mixture comprising crystalline and amorphous forms.

Figure 4:
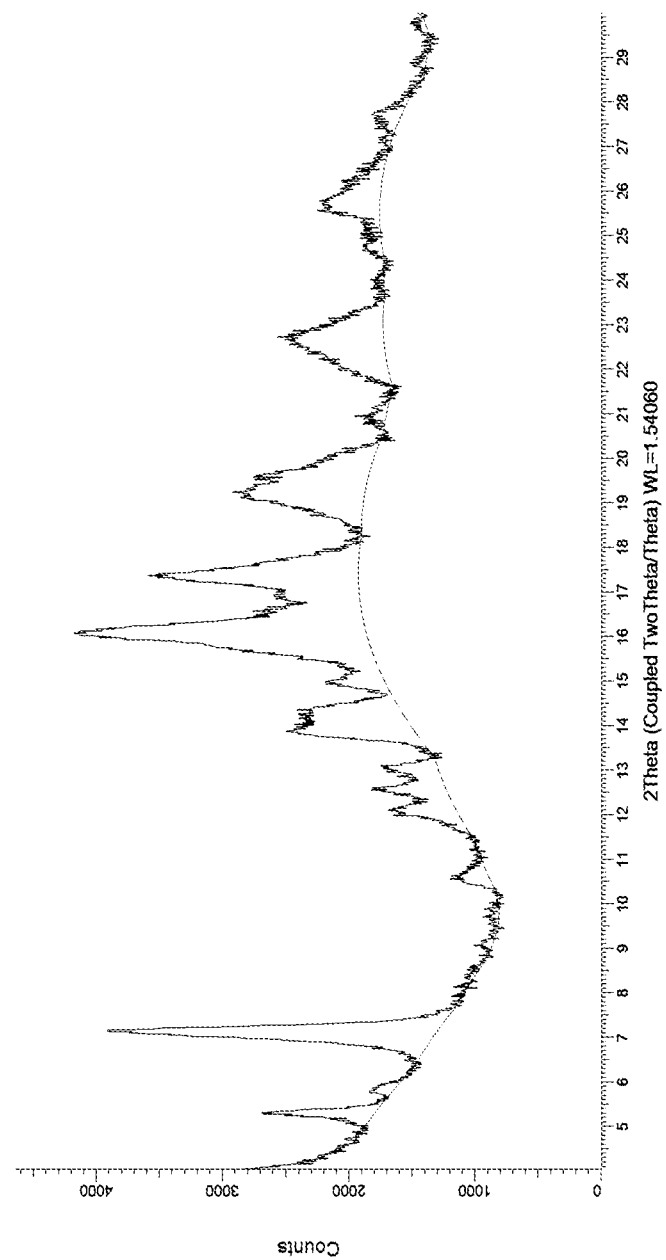
FIG. 4 shows an XRPD pattern of Compound 1 di-sodium salt.

In some embodiments, Compound 1 di-sodium salt can be characterized by the X-ray powder diffraction (XRPD) pattern substantially as shown in FIG. 4.

In some embodiments, Compound 1 di-sodium salt has at least one X-ray powder diffraction (XRPD) peak, in terms of 2-theta (0.2 degrees), selected from 5.3, 7.1, 10.6, 13.9, 14.3, 16.1 and 17.4 degrees. In some embodiments, Compound 1 di-sodium salt has at least two X-ray powder diffraction (XRPD) peaks, in terms of 2-theta (0.2 degrees), selected from 5.3, 7.1, 10.6, 13.9, 14.3, 16.1 and 17.4 degrees. In some embodiments, Compound 1 di-sodium salt has at least three X-ray powder diffraction (XRPD) peaks, in terms of 2-theta (0.2 degrees), selected from 5.3, 7.1, 10.6, 13.9, 14.3, 16.1 and 17.4 degrees. In some embodiments, Compound 1 di-sodium salt has at least four X-ray powder diffraction (XRPD) peaks, in terms of 2-theta (0.2 degrees), selected from 5.3, 7.1, 10.6, 13.9, 14.3, 16.1 and 17.4 degrees. In some embodiments, Compound 1 di-sodium salt has characteristic X-ray powder diffraction (XRPD) peaks, in terms of 2-theta (0.2 degrees), at 5.3, 7.1, 10.6, 13.9, 14.3, 16.1 and 17.4 degrees.

Figure 5:
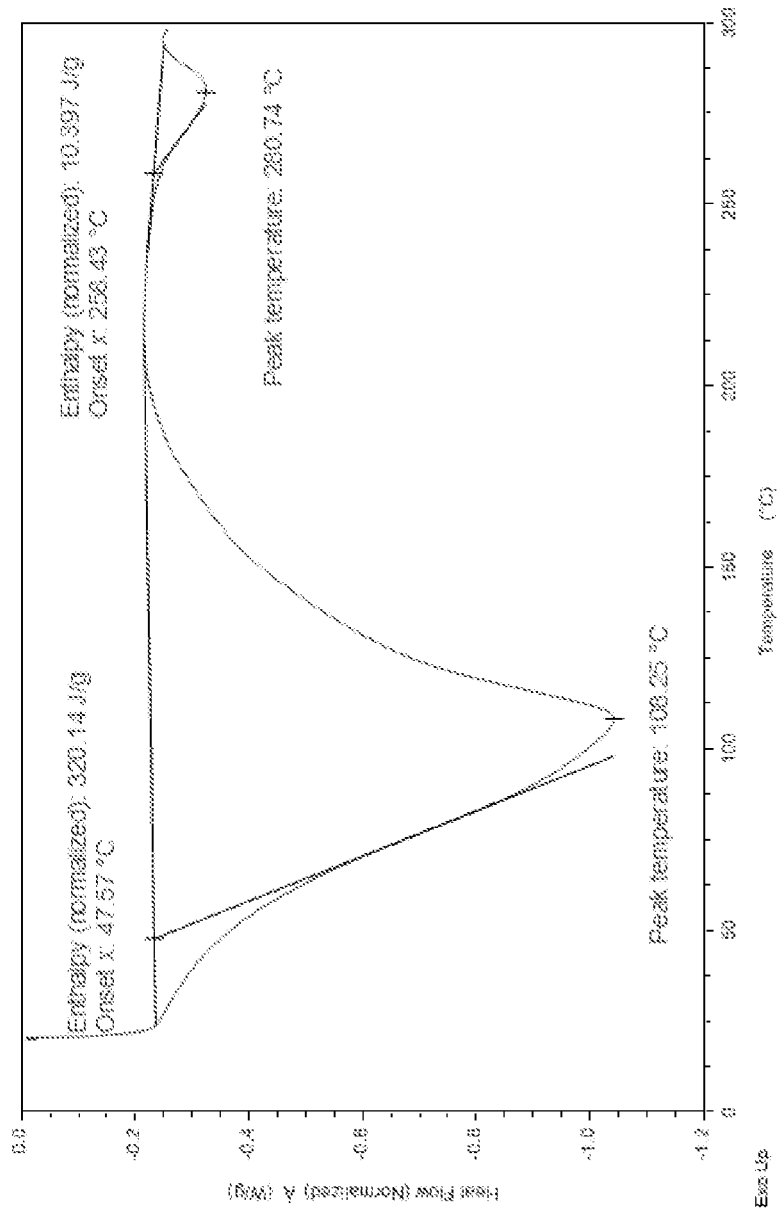
FIG. 5 shows a DSC thermogram of Compound 1 di-sodium salt.
Figure 6:
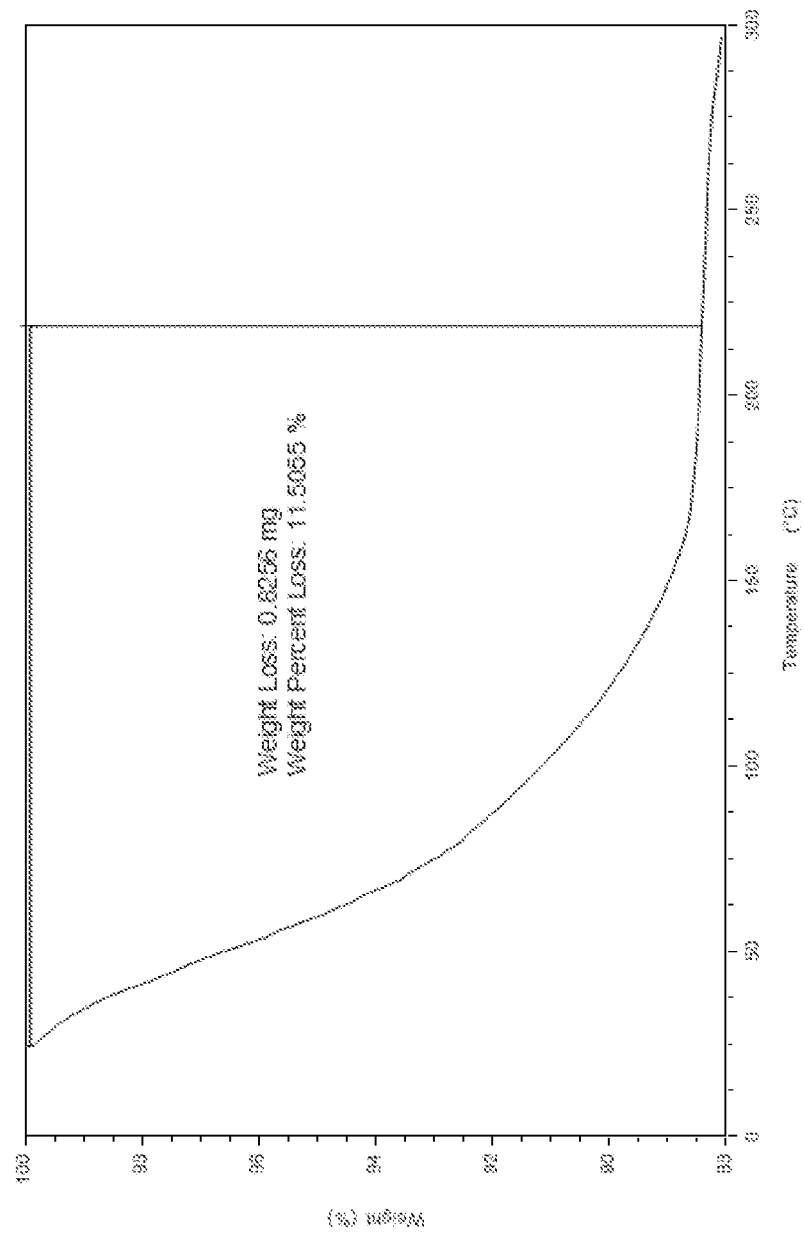
FIG. 6 shows a TGA thermogram of Compound 1 di-sodium salt.

In some embodiments, Compound 1 di-sodium salt exhibits a DSC thermogram having a first endothermic peak with an onset temperature of 47±3° C. and a maximum at 108±3° C. and a second endothermic peak with an onset temperature of 258±3° C. and a maximum at 280±3° C. In some embodiments, Compound 1 di-sodium salt has a DSC thermogram substantially as depicted in FIG. 5. In some embodiments, Compound 1 di-sodium salt has a TGA thermogram substantially as depicted in FIG. 6.

Hydrochloric Acid Salts

In some embodiments, the salt of Compound 1 is 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt (Compound 1 di-hydrochloric acid salt).

In some embodiments, the salt is 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) mono-hydrochloric acid salt (Compound 1 mono-hydrochloric acid salt).

Compound 1 mono-hydrochloric acid salt can be prepared by any suitable method for preparation of mono-hydrochloric acid addition salts. For example, Compound 1 can be reacted with hydrochloric acid (e.g., about 1.0 molar eq. or more) in a solvent and the resulting salt can be isolated by filtering the salt from solution. In certain embodiments, Compound 1 is reacted with about 1 to about 2 molar equivalents of hydrochloric acid. In certain embodiments, Compound 1 is reacted with about 1 to about 1.5 molar equivalents of hydrochloric acid. In certain embodiments, Compound 1 is reacted with about 1.05 molar equivalents of hydrochloric acid.

The solvent can comprise any solvent or mixture of solvents capable of at least partially dissolving Compound 1. In some embodiments, the solvent comprises an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent comprises acetone, tetrahydrofuran, dichloromethane, methanol, ethanol, 1-propanol, or isopropanol. In some embodiments, the solvent comprises dichloromethane. In some embodiments, the solvent comprises methanol.

In some embodiments, the solvent is a mixture of isopropanol, water, methanol and dichloromethane. In some embodiments, the solvent is a mixture of isopropanol, water and methanol.

In some embodiments, the solvent is combined with Compound I and hydrochloric acid at about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C., or about 80° C.

In some embodiments, the solvent is heated to a temperature that can induce precipitation and/or crystallization at a practical rate. In some embodiments, precipitation and/or crystallization is completed within about 1 to about 12 hours, but longer and shorter periods are possible depending on the choice of precipitation/crystallizing solvent and temperature. In some embodiments, the precipitation and/or crystallization is completed within about 1 hour.

The precipitation and/or crystallization of the mono-hydrochloric acid salt, in some embodiments, is carried out by filtering the salt from solution.

In some embodiments, Compound 1 mono-hydrochloric acid salt is amorphous. In some embodiments, Compound 1 mono-hydrochloric acid salt is crystalline. In some embodiments, Compound 1 mono-hydrochloric acid salt is a mixture comprising crystalline and amorphous forms.

In some embodiments, Compound 1 mono-hydrochloric acid salt has Form VI.

In some embodiments, Compound 1 mono-hydrochloric acid salt Form VI is produced via adding Compound 1 di-hydrochloric acid salt Form I to a saturated solution of Compound 1 di-hydrochloric acid salt Form I in water at 50±1° C., stirring for 2 days at 50±1° C., and filtering the resulting solid.

Figure 25:
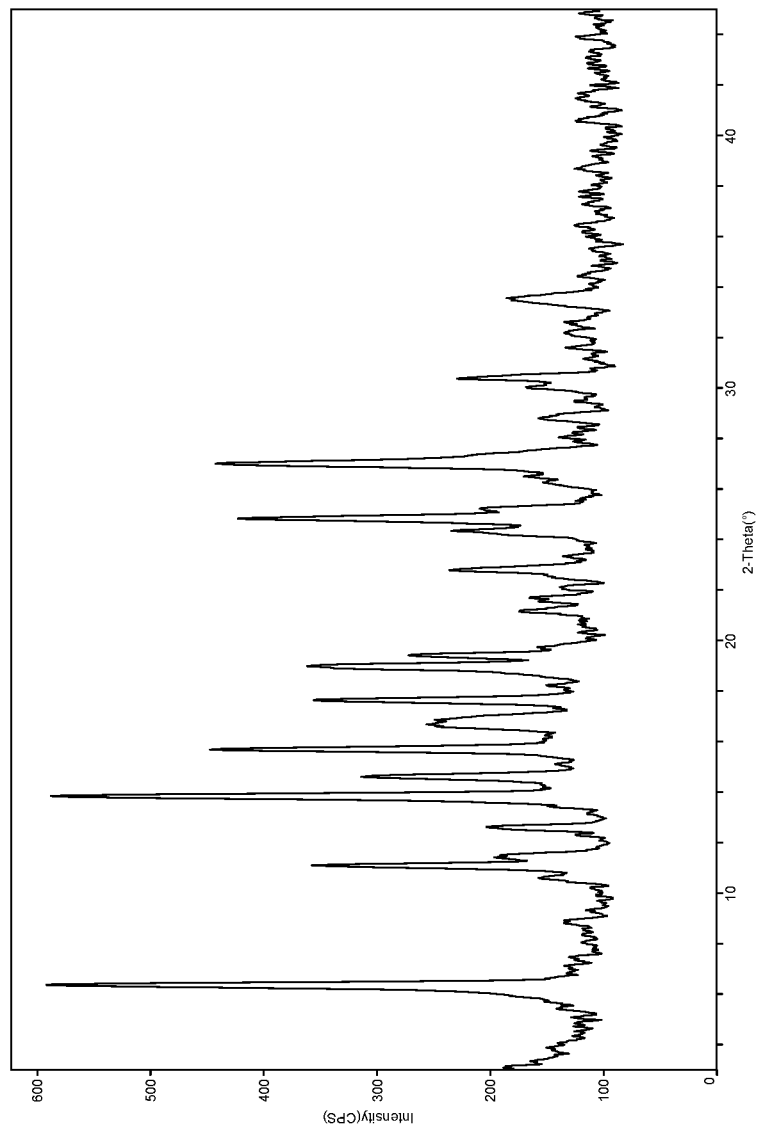
FIG. 25 shows an XRPD pattern of Compound 1 mono-hydrochloric acid salt Form VI.

In some embodiments, Compound 1 mono-hydrochloric acid salt Form VI can be characterized by the X-ray powder diffraction (XRPD) pattern substantially as shown in FIG. 25.

In some embodiments, Compound 1 mono-hydrochloric acid salt Form VI has at least one X-ray powder diffraction (XRPD) peak, in terms of 2-theta (±0.2 degrees), selected from 6.4, 11.1, 12.6, 13.8, 14.6, 15.7, 16.9, 17.6, 19.0 and 19.5 degrees. In some embodiments, Compound 1 mono-hydrochloric acid salt Form VI has at least two X-ray powder diffraction (XRPD) peaks, in terms of 2-theta (±0.2 degrees), selected from 6.4, 11.1, 12.6, 13.8, 14.6, 15.7, 16.9, 17.6, 19.0 and 19.5 degrees. In some embodiments, Compound 1 mono-hydrochloric acid salt Form VI has at least three X-ray powder diffraction (XRPD) peaks, in terms of 2-theta (±0.2 degrees), selected from 6.4, 11.1, 12.6, 13.8, 14.6, 15.7, 16.9, 17.6, 19.0 and 19.5 degrees. In some embodiments, Compound 1 mono-hydrochloric acid salt Form VI has at least four X-ray powder diffraction (XRPD) peaks, in terms of 2-theta (±0.2 degrees), selected from 6.4, 11.1, 12.6, 13.8, 14.6, 15.7, 16.9, 17.6, 19.0 and 19.5 degrees. In some embodiments, Compound 1 mono-hydrochloric acid salt Form VI has characteristic X-ray powder diffraction (XRPD) peaks, in terms of 2-theta (±0.2 degrees), at 6.4, 11.1, 12.6, 13.8, 14.6, 15.7, 16.9, 17.6, 19.0 and 19.5 degrees.

Figure 26:
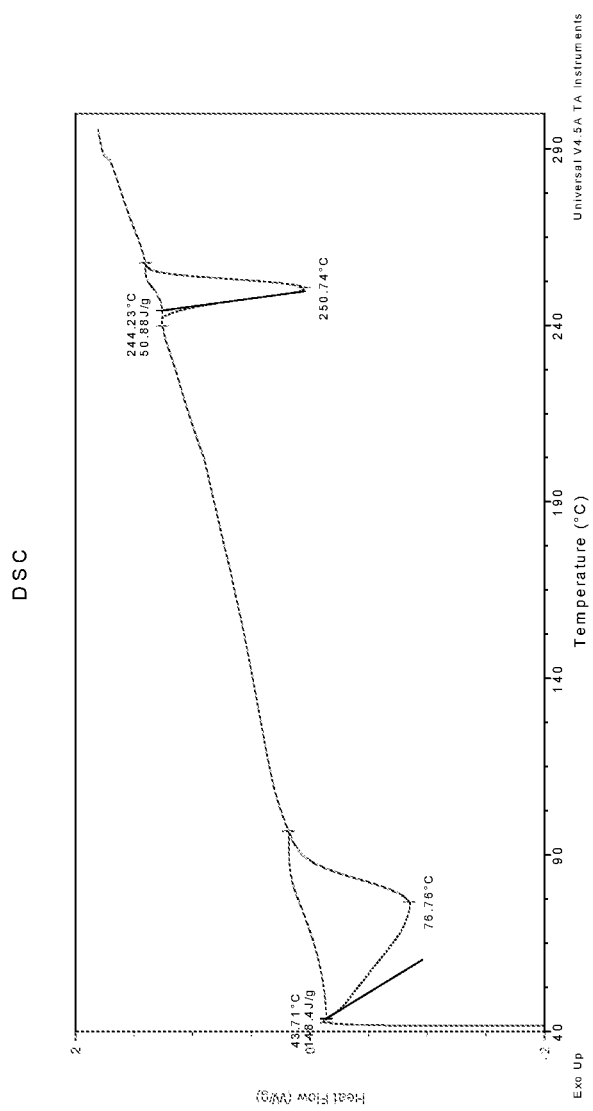
FIG. 26 shows a DSC thermogram of Compound 1 mono-hydrochloric acid salt Form VI.
Figure 27:
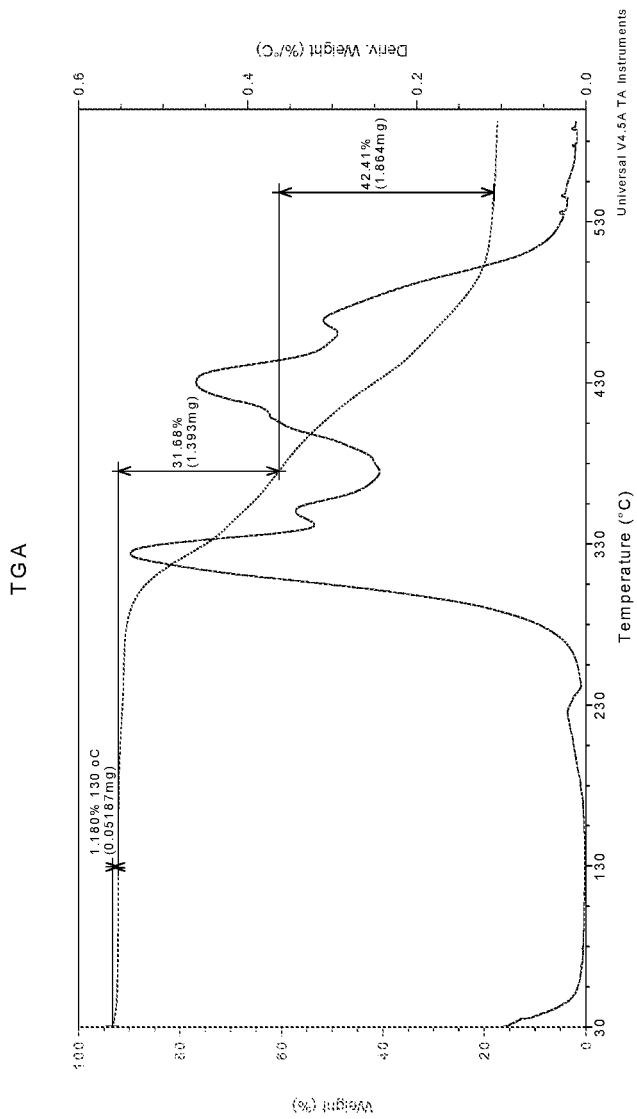
FIG. 27 shows a TGA thermogram of Compound 1 mono-hydrochloric acid salt Form VI.
Figure 28:
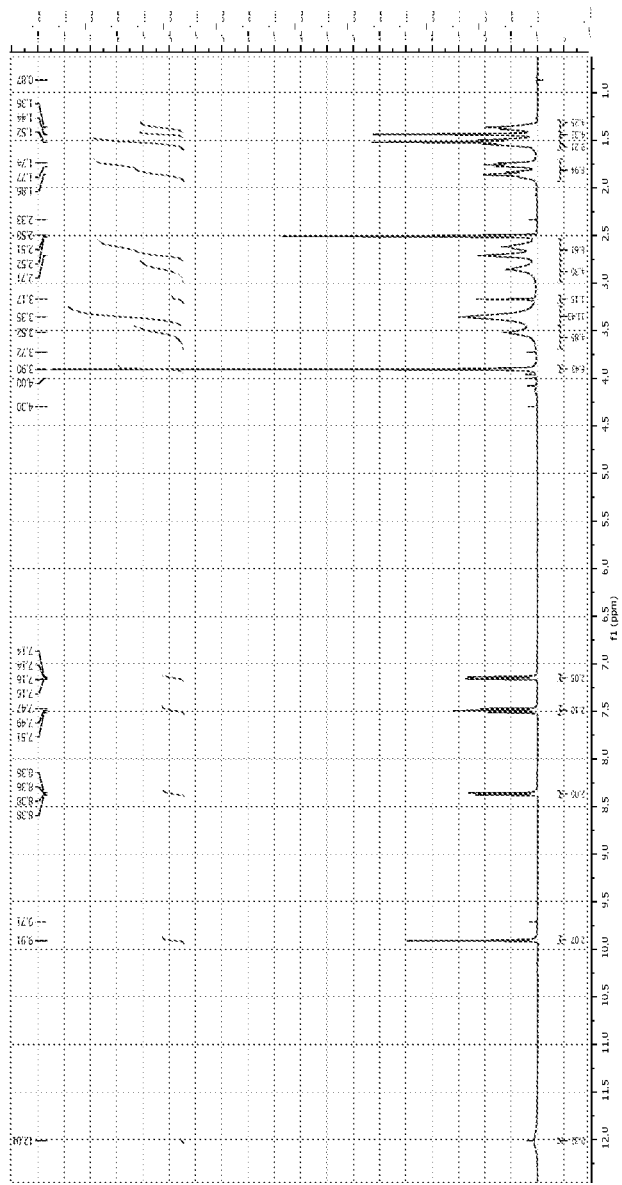
FIG. 28 shows a $^1$H NMR of Compound 1 mono-hydrochloric acid salt Form VI in DMSO-d6.

In some embodiments, Compound 1 mono-hydrochloric acid salt Form VI exhibits a DSC thermogram having a first endothermic peak with an onset temperature at 44±3° C. and a maximum at 77±3° C., and a second endothermic peak with an onset temperature at 244±3° C. and a maximum at 251±3° C. In some embodiments, Compound 1 mono-hydrochloric acid salt Form VI has a DSC thermogram substantially as depicted in FIG. 26. In some embodiments, Compound 1 mono-hydrochloric acid salt Form VI has a TGA thermogram substantially as depicted in FIG. 27. In some embodiments, Compound 1 mono-hydrochloric acid salt Form VI has a NMR spectrum substantially as depicted in FIG. 28.

Compound 1 di-hydrochloric acid salt can be prepared by any suitable method for preparation of di-hydrochloric acid addition salts. For example, Compound 1 can be reacted with hydrochloric acid (e.g., about 2.0 molar eq. or more) in a solvent and the resulting salt can be isolated by filtering the salt from solution. In certain embodiments, Compound 1 is reacted with about 2 to about 3 molar equivalents of hydrochloric acid. In certain embodiments, Compound 1 is reacted with about 2 to about 2.5 molar equivalents of hydrochloric acid. In certain embodiments, Compound 1 is reacted with about 2.2 molar equivalents of hydrochloric acid.

The solvent can comprise any solvent or mixture of solvents capable of at least partially dissolving Compound 1. In some embodiments, the solvent comprises an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol mono methyl ether, diethylene glycol monoethyl ether, cyclohexanol, benzyl alcohol, phenol, or glycerol. In some embodiments, the solvent comprises dioxane, dimethylsulfoxide, acetone, tetrahydrofuran, dichloromethane, methanol, ethanol, 1-propanol, or isopropanol. In some embodiments, the solvent comprises acetone. In some embodiments, the solvent comprises water. In some embodiments, the solvent comprises acetone and water.

In some embodiments, the solvent is a mixture of acetone and water.

In some embodiments, the solvent is about room temperature. In some embodiments, the solvent is heated to a temperature of about 55° C. In some embodiments, the temperature is from about 50° C. to about 80° C. In some embodiments, the temperature is from about 40° C. to about 60° C. In some embodiments, the temperature is from about 55° C. to about 60° C. In some embodiments, the temperature is about 45° C., about 50° C., about 55° C., about 60° C., about 65° C., about 70° C., about 75° C., or about 80° C.

In some embodiments, the solvent is heated to a temperature that can induce precipitation at a practical rate. In some embodiments, precipitation is completed within about 4 to about 24 hours, but longer and shorter periods are possible depending on the choice of precipitation solvent and temperature. In some embodiments, precipitation is completed within about 5 hours.

The precipitation of the di-hydrochloric acid salt, in some embodiments, is carried out by filtering the salt from solution.

In some embodiments, Compound 1 di-hydrochloric acid salt is amorphous. In some embodiments, Compound 1 di-hydrochloric acid salt is crystalline. In some embodiments, Compound 1 di-hydrochloric acid salt is a mixture comprising crystalline and amorphous forms.

In some embodiments, Compound 1 di-hydrochloric acid salt has Form I.

In some embodiments, Compound 1 di-hydrochloric acid salt Form I can be produced by a process comprising precipitating Compound 1 di-hydrochloric acid Form I from a solvent, following reacting of Compound 1 with hydrochloric acid (e.g., about 2.0 molar eq. or more) in the solvent. In some embodiments, the solvent is acetone, water, or a mixture thereof.

For example, Compound 1 di-hydrochloric acid salt Form I can be prepared by a process comprising:
 a) preparing a suspension of Compound 1 and at least 2 equivalents of hydrochloric acid in a solvent comprising acetone;
 b) heating the suspension of a) to above room temperature to form a clear solution;
 c) cooling the clear solution of b) to about room temperature;
 d) adding a solvent comprising acetone to the mixture of c) to form a cloudy solution; and
 e) filtering the cloudy solution of d) to provide said Form I as a solid.

For example, Compound 1 di-hydrochloric acid salt Form I can be prepared by a process comprising:
 a) preparing a suspension of Compound 1 and at least 2 equivalents (e.g., about 2.2 equivalents) of hydrochloric acid in a solvent comprising acetone;
 b) heating the suspension of a) to about 55° C. to form a clear solution;
 c) cooling the clear solution of b) to about room temperature followed by polish filtration to provide a mixture;
 d) adding a solvent comprising acetone to the mixture of c) to form a cloudy solution;
 e) filtering the cloudy solution of d) to provide said Form I as a solid;
 f) adding a solvent comprising acetone and water to the solid of e) to provide a mixture;
 g) heating the mixture of f) to a temperature of from about 55 to about 60° C.;
 h) cooling the mixture of g) to about room temperature;
 i) filtering the mixture of h) to provide a solid, and
 j) drying of the solid i) under vacuum at about 50° C.

Figure 7:
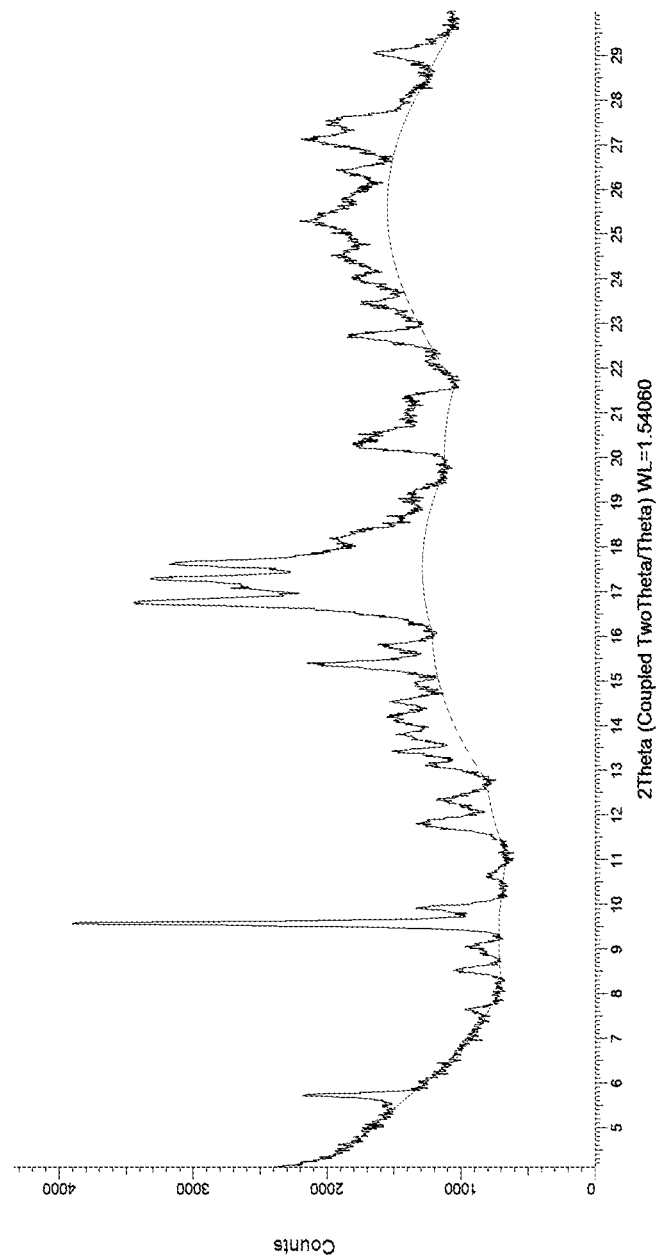
FIG. 7 shows an XRPD pattern of Compound 1 di-hydrochloric acid salt Form I.

In some embodiments, Compound 1 di-hydrochloric acid salt Form I can be characterized by the X-ray powder diffraction (XRPD) pattern substantially as shown in FIG. 7.

In some embodiments, Compound 1 di-hydrochloric acid salt Form I has at least one X-ray powder diffraction (XRPD) peak, in terms of 2-theta (±0.2 degrees), selected from 5.7, 8.5, 9.6, 9.9, 11.8, 12.3, 13.1, 13.4, 13.8, 14.2, 14.5, 15.4, 15.8, 16.8, 17.3 and 17.6 degrees. In some embodiments, Compound 1 di-hydrochloric acid salt Form I has at least two X-ray powder diffraction (XRPD) peaks, in terms of 2-theta (±0.2 degrees), selected from 5.7, 8.5, 9.6, 9.9, 11.8, 12.3, 13.1, 13.4, 13.8, 14.2, 14.5, 15.4, 15.8, 16.8, 17.3 and 17.6 degrees. In some embodiments, Compound 1 di-hydrochloric acid salt Form I has at least three X-ray powder diffraction (XRPD) peaks, in terms of 2-theta (±0.2 degrees), selected from 5.7, 8.5, 9.6, 9.9, 11.8, 12.3, 13.1, 13.4, 13.8, 14.2, 14.5, 15.4, 15.8, 16.8, 17.3 and 17.6 degrees. In some embodiments, Compound 1 di-hydrochloric acid salt Form I has at least four X-ray powder diffraction (XRPD) peaks, in terms of 2-theta (±0.2 degrees), selected from 5.7, 8.5, 9.6, 9.9, 11.8, 12.3, 13.1, 13.4, 13.8, 14.2, 14.5, 15.4, 15.8, 16.8, 17.3 and 17.6 degrees. In some embodiments, Compound 1 di-hydrochloric acid salt Form I has characteristic X-ray powder diffraction (XRPD) peaks, in terms of 2-theta (±0.2 degrees), at 5.7, 8.5, 9.6, 9.9, 11.8, 12.3, 13.1, 13.4, 13.8, 14.2, 14.5, 15.4, 15.8, 16.8, 17.3 and 17.6 degrees.

Figure 8:
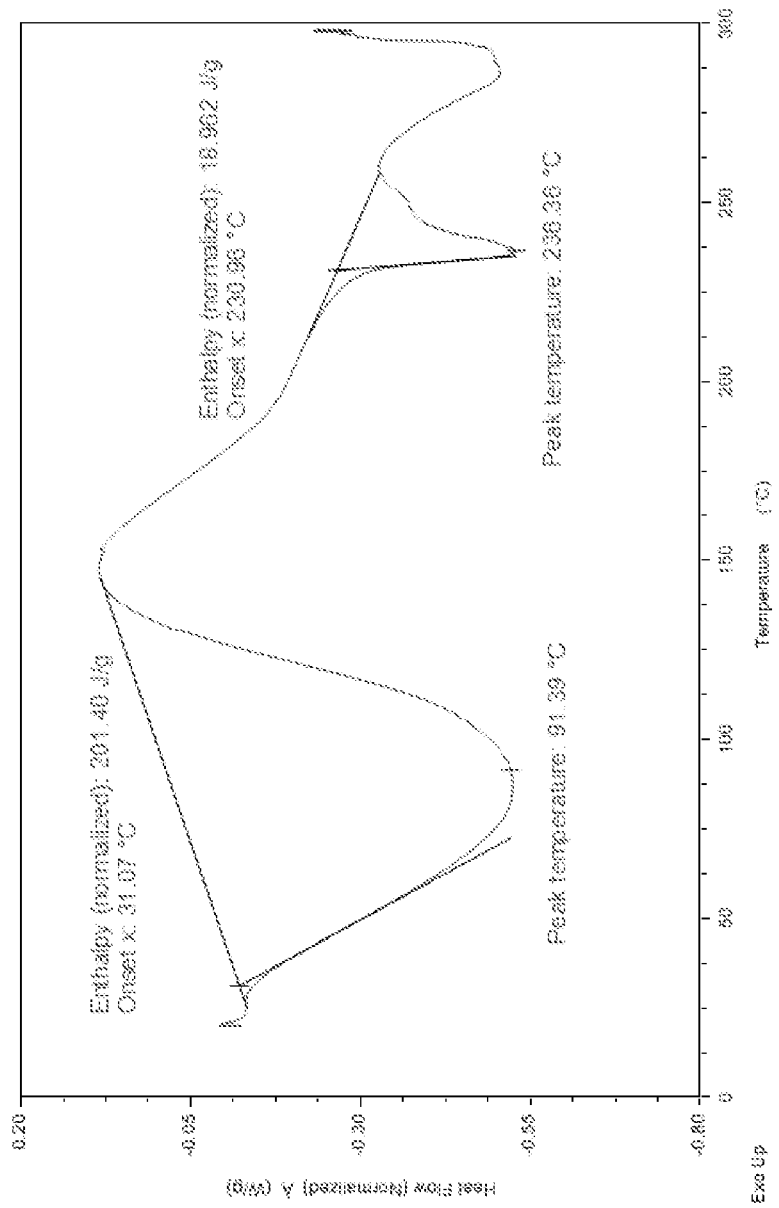
FIG. 8 shows a DSC thermogram of Compound 1 di-hydrochloric acid salt Form I.
Figure 9:
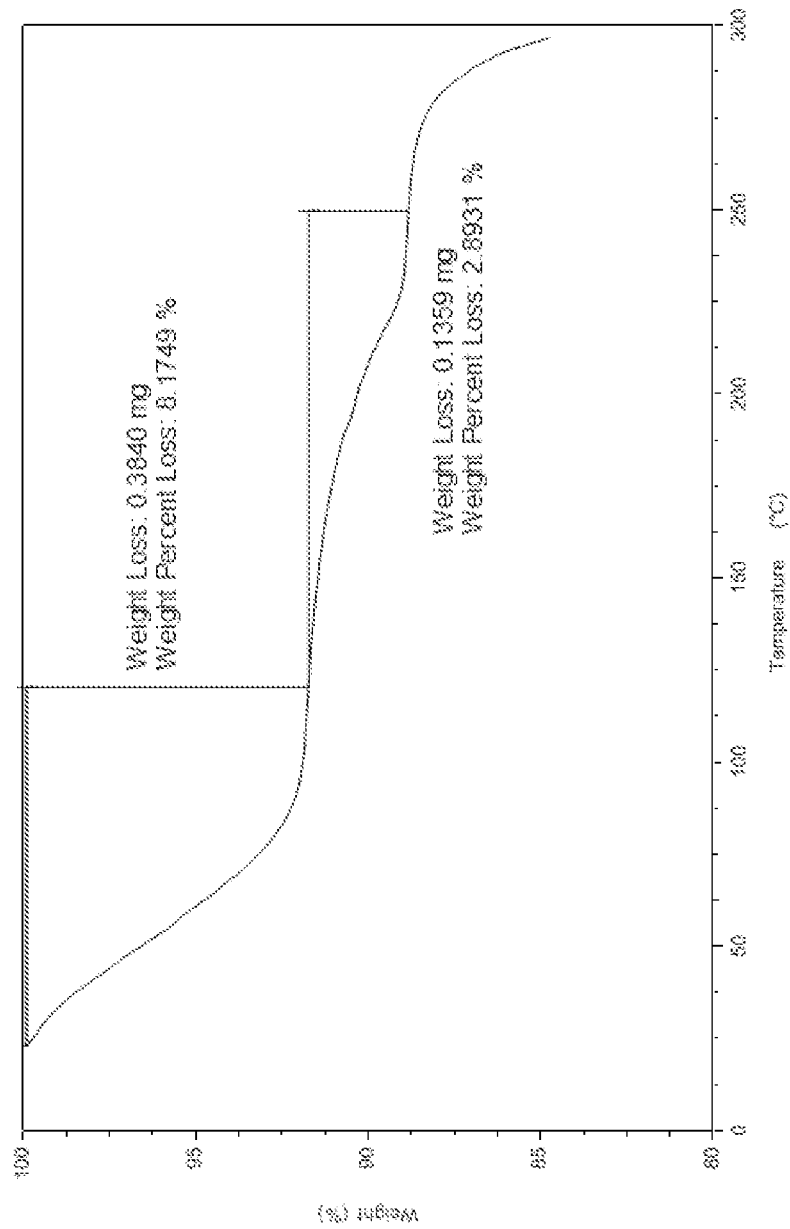
FIG. 9 shows a TGA thermogram of Compound 1 di-hydrochloric acid salt Form I.
Figure 10:
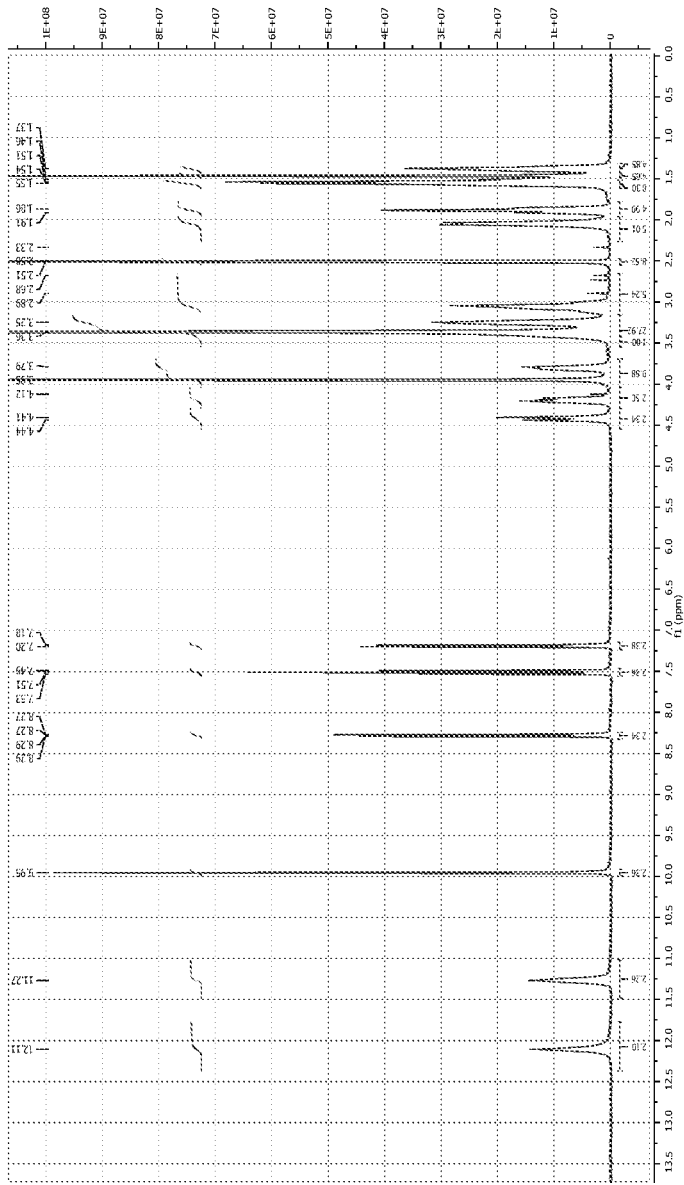
FIG. 10 shows a $^1$H NMR of Compound 1 di-hydrochloric acid salt Form I in DMSO-d6.

In some embodiments, Compound 1 di-hydrochloric acid salt Form I exhibits a DSC thermogram having a first endothermic peak with an onset temperature at 31.1° C. and a maximum at 91.4° C., and a second endothermic peak with an onset temperature at 231.0° C. and a maximum at 236.4° C. In some embodiments, Compound 1 di-hydrochloric acid salt Form I has a DSC thermogram substantially as depicted in FIG. 8. In some embodiments, Compound 1 di-hydrochloric acid salt Form I has a TGA thermogram substantially as depicted in FIG. 9. In some embodiments, Compound 1 mono-hydrochloric acid salt Form I has a NMR spectrum substantially as depicted in FIG. 10.

In some embodiments, Compound 1 di-hydrochloric acid salt has Form II.

In some embodiments, Compound 1 di-hydrochloric acid salt Form II is produced via dissolving amorphous Compound 1 di-hydrochloric acid salt in a solvent comprising about 10:3 acetonitrile/water, reducing the volume of the mixture by evaporation at about 70° C., adding acetonitrile and heating to about 70° C., stirring the resulting suspension at about room temperature, isolating the resulting solid, and drying the solid at about 50° C.

Figure 11:
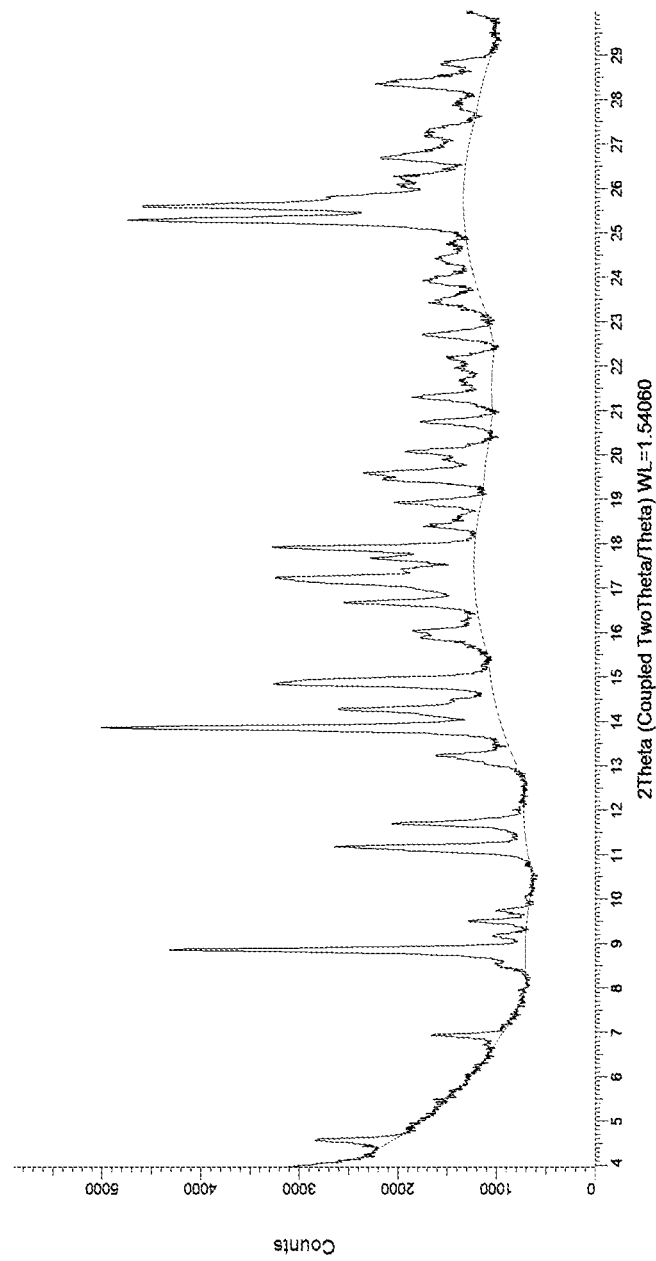
FIG. 11 shows an XRPD pattern of Compound 1 di-hydrochloric acid salt Form II.

In some embodiments, Compound 1 di-hydrochloric acid salt Form II can be characterized by the X-ray powder diffraction (XRPD) pattern substantially as shown in FIG. 11.

In some embodiments, Compound 1 di-hydrochloric acid salt Form II has at least one X-ray powder diffraction (XRPD) peak, in terms of 2-theta (±0.2 degrees), selected from 4.6, 6.9, 8.9, 11.2, 11.7, 13.2, 13.9, 14.3, 14.8, 16.0, 16.7, 17.2, 17.9, 25.3 and 25.6 degrees. In some embodiments, Compound 1 di-hydrochloric acid salt Form II has at least two X-ray powder diffraction (XRPD) peaks, in terms of 2-theta (±0.2 degrees), selected from 4.6, 6.9, 8.9, 11.2, 11.7, 13.2, 13.9, 14.3, 14.8, 16.0, 16.7, 17.2, 17.9, 25.3 and 25.6 degrees. In some embodiments, Compound 1 di-hydrochloric acid salt Form II has at least three X-ray powder diffraction (XRPD) peaks, in terms of 2-theta (±0.2 degrees), selected from 4.6, 6.9, 8.9, 11.2, 11.7, 13.2, 13.9, 14.3, 14.8, 16.0, 16.7, 17.2, 17.9, 25.3 and 25.6 degrees. In some embodiments, Compound 1 di-hydrochloric acid salt Form II has at least four X-ray powder diffraction (XRPD) peaks, in terms of 2-theta (±0.2 degrees), selected from 4.6, 6.9, 8.9, 11.2, 11.7, 13.2, 13.9, 14.3, 14.8, 16.0, 16.7, 17.2, 17.9, 25.3 and 25.6 degrees. In some embodiments, Compound 1 di-hydrochloric acid salt Form II has characteristic X-ray powder diffraction (XRPD) peaks, in terms of 2-theta (±0.2 degrees), at 4.6, 6.9, 8.9, 11.2, 11.7, 13.2, 13.9, 14.3, 14.8, 16.0, 16.7, 17.2, 17.9, 25.3 and 25.6 degrees.

Figure 12:
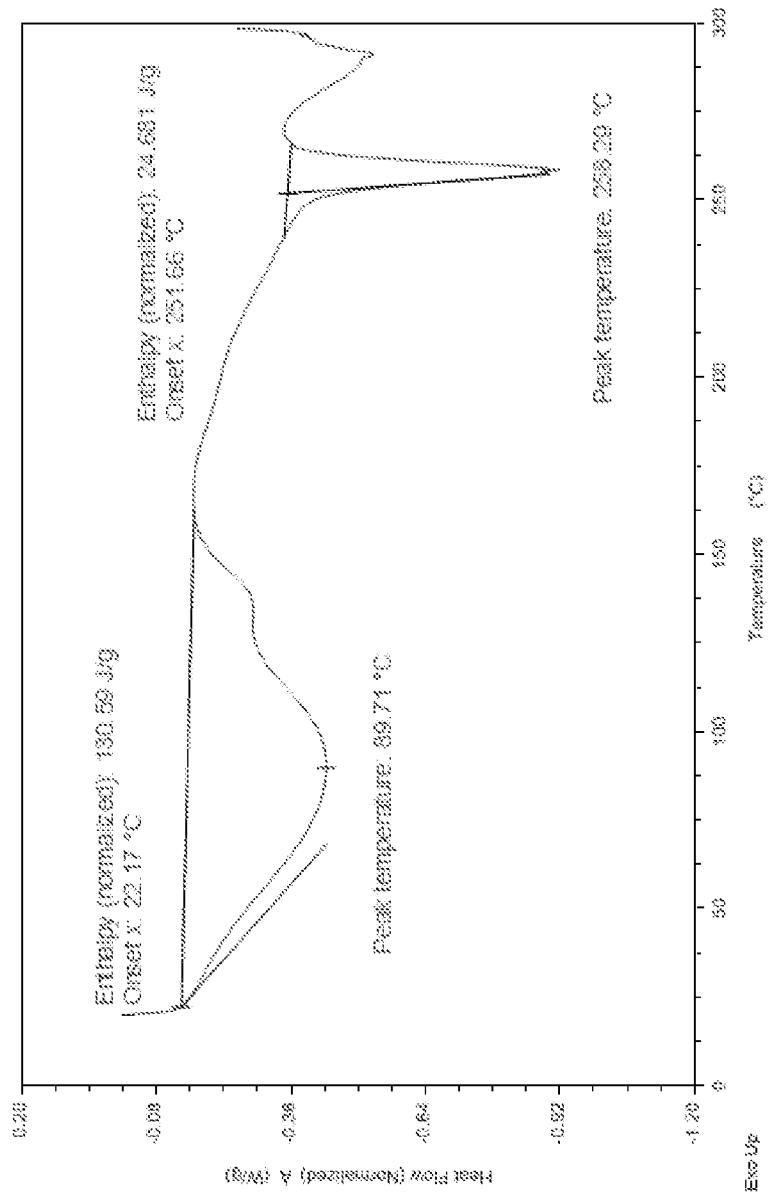
FIG. 12 shows a DSC thermogram of Compound 1 di-hydrochloric acid salt Form II.
Figure 13:
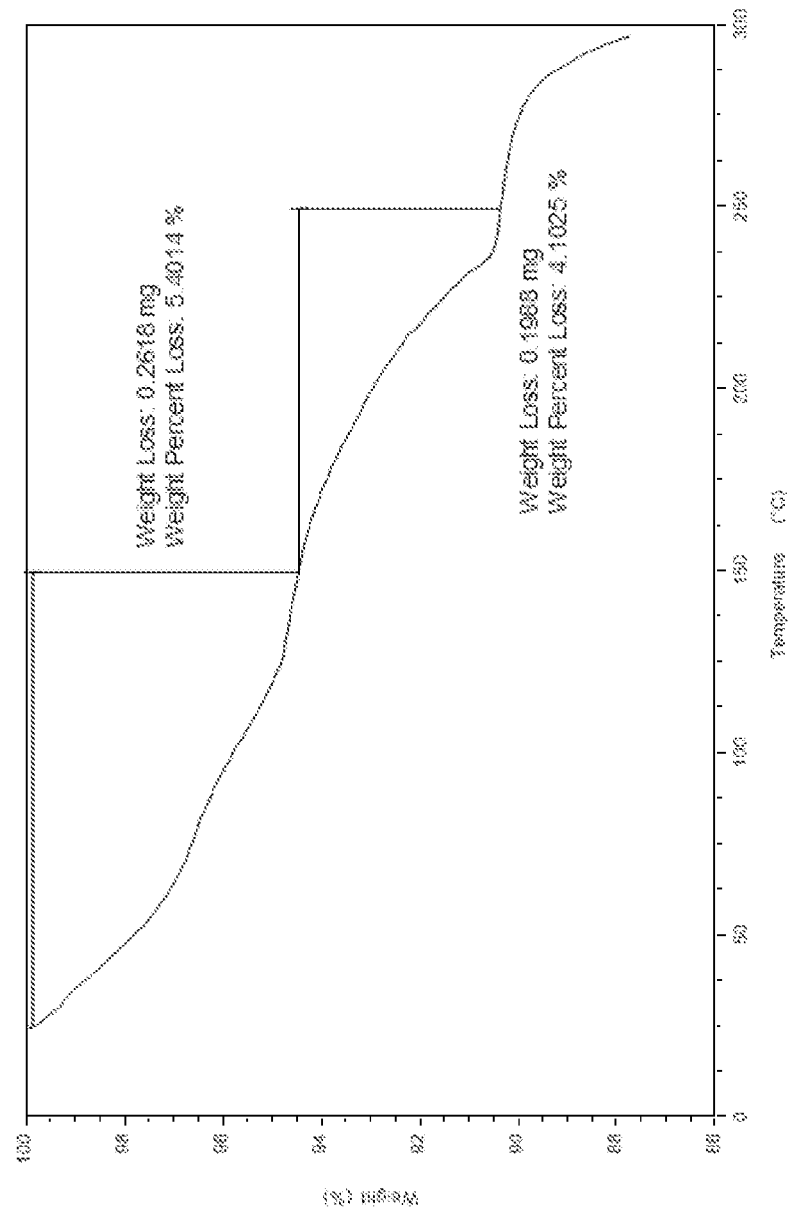
FIG. 13 shows a TGA thermogram of Compound 1 di-hydrochloric acid salt Form II.

In some embodiments, Compound 1 di-hydrochloric acid salt Form II exhibits a DSC thermogram having a first endothermic peak with an onset temperature at 22.2° C. and a maximum at 89.7° C., and a second endothermic peak with an onset temperature at 251.7° C. and a maximum at 258.3° C. In some embodiments, Compound 1 di-hydrochloric acid salt Form II has a DSC thermogram substantially as depicted in FIG. 12. In some embodiments, Compound 1 di-hydrochloric acid salt Form II has a TGA thermogram substantially as depicted in FIG. 13.

In some embodiments, Compound 1 di-hydrochloric acid salt has Form III.

In some embodiments, Compound 1 di-hydrochloric acid salt Form III is produced via adding Compound 1 di-hydrochloric acid salt Form I to a saturated or cloudy solution of Compound 1 di-hydrochloric acid salt Form I in a solvent comprising methanol, stirring (e.g., for at least 24 hours, or for about 3 days), and isolating the resulting solid.

Figure 14:
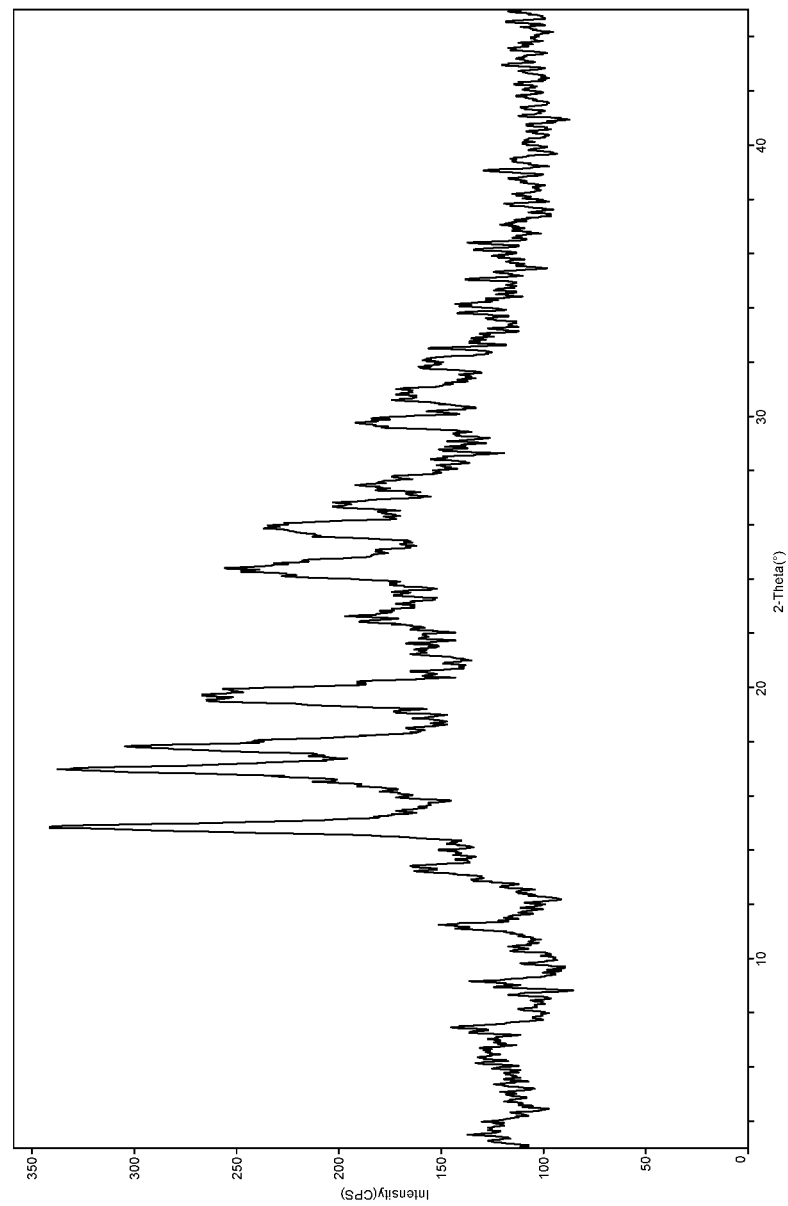
FIG. 14 shows an XRPD pattern of Compound 1 di-hydrochloric acid salt Form III.

In some embodiments, Compound 1 di-hydrochloric acid salt Form III can be characterized by the X-ray powder diffraction (XRPD) pattern substantially as shown in FIG. 14.

In some embodiments, Compound 1 di-hydrochloric acid salt Form III has at least one X-ray powder diffraction (XRPD) peak, in terms of 2-theta (±0.2 degrees), selected from 9.2, 11.2, 14.9, 17.0, 17.8, 19.7, 24.4 and 25.9 degrees. In some embodiments, Compound 1 di-hydrochloric acid salt Form III has at least two X-ray powder diffraction (XRPD) peaks, in terms of 2-theta (±0.2 degrees), selected from 9.2, 11.2, 14.9, 17.0, 17.8, 19.7, 24.4 and 25.9 degrees. In some embodiments, Compound 1 di-hydrochloric acid salt Form III has at least three X-ray powder diffraction (XRPD) peaks, in terms of 2-theta (±0.2 degrees), selected from 9.2, 11.2, 14.9, 17.0, 17.8, 19.7, 24.4 and 25.9 degrees. In some embodiments, Compound 1 di-hydrochloric acid salt Form III has at least four X-ray powder diffraction (XRPD) peaks, in terms of 2-theta (±0.2 degrees), selected from 9.2, 11.2, 14.9, 17.0, 17.8, 19.7, 24.4 and 25.9 degrees. In some embodiments, Compound 1 di-hydrochloric acid salt Form III has characteristic X-ray powder diffraction (XRPD) peaks, in terms of 2-theta (±0.2 degrees), at 9.2, 11.2, 14.9, 17.0, 17.8, 19.7, 24.4 and 25.9 degrees.

Figure 15:
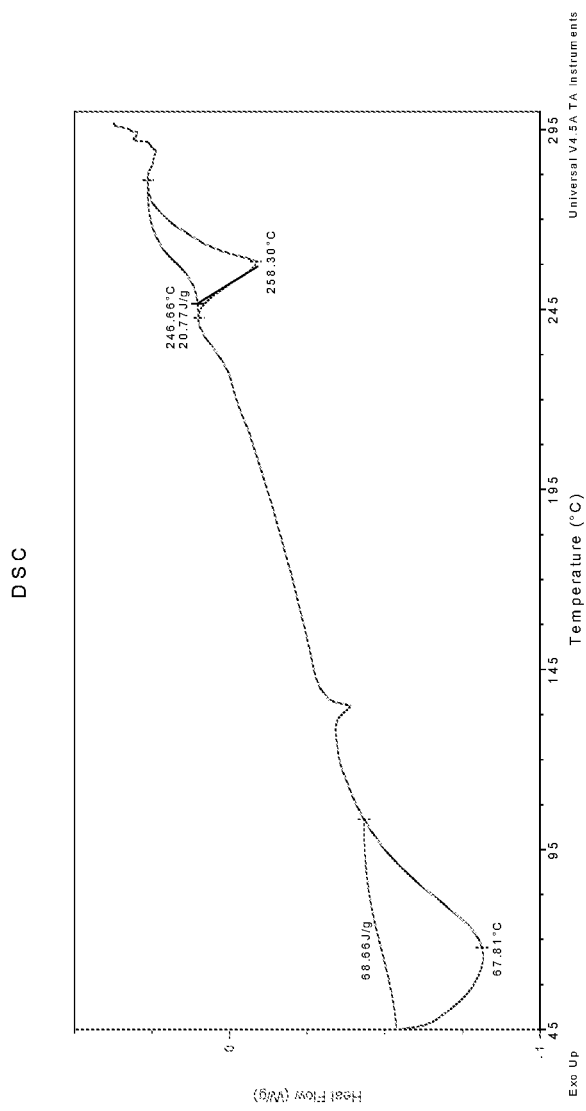
FIG. 15 shows a DSC thermogram of Compound 1 di-hydrochloric acid salt Form III.
Figure 16:
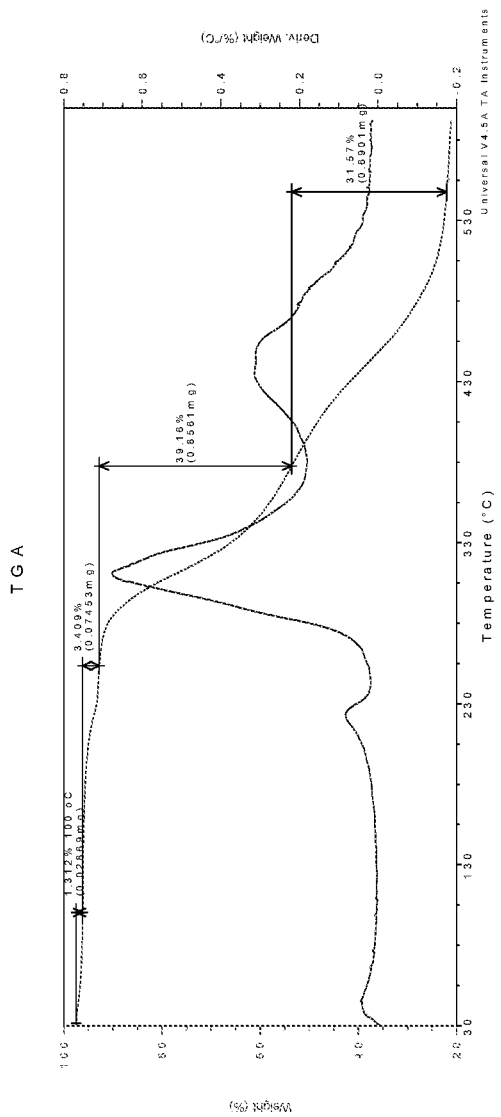
FIG. 16 shows a TGA thermogram of Compound 1 di-hydrochloric acid salt Form III.

In some embodiments, Compound 1 di-hydrochloric acid salt Form III exhibits a DSC thermogram having an endothermic peak with an onset temperature of 247±3° C. and a maximum at 258±3° C. In some embodiments, Compound 1 di-hydrochloric acid salt Form III has a DSC thermogram substantially as depicted in FIG. 15. In some embodiments, Compound 1 di-hydrochloric acid salt Form III has a TGA thermogram substantially as depicted in FIG. 16.

In some embodiments, Compound 1 di-hydrochloric acid salt has Form IV.

In some embodiments, Compound 1 di-hydrochloric acid salt Form IV is produced via adding Compound 1 di-hydrochloric acid salt Form I to a saturated or cloudy solution of Compound 1 di-hydrochloric acid salt Form I in a solvent comprising n-butanol, stirring (e.g., for at least 24 hours, or for about 3 days) at about 25° C., and isolating the resulting solid.

Figure 17:
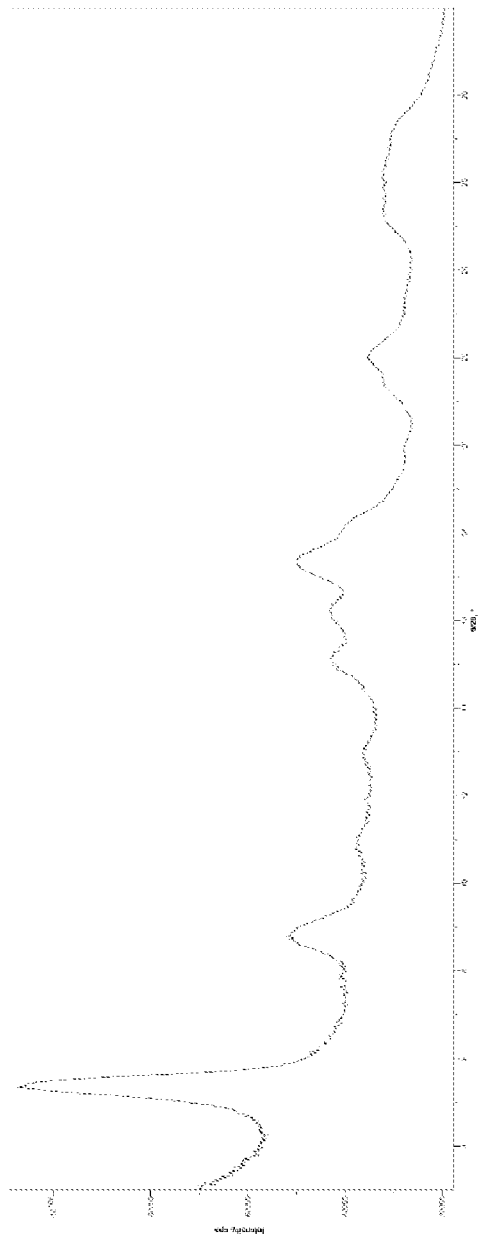
FIG. 17 shows an XRPD pattern of Compound 1 di-hydrochloric acid salt Form IV.

In some embodiments, Compound 1 di-hydrochloric acid salt Form IV can be characterized by the X-ray powder diffraction (XRPD) pattern substantially as shown in FIG. 17.

In some embodiments, Compound 1 di-hydrochloric acid salt Form IV has at least one X-ray powder diffraction (XRPD) peak, in terms of 2-theta (±0.2 degrees), selected from 5.4, 8.8, 10.9, 13.0, 15.1, 16.2, 17.5, 21.9 and 26.3 degrees. In some embodiments, Compound 1 di-hydrochloric acid salt Form IV has at least two X-ray powder diffraction (XRPD) peaks, in terms of 2-theta (±0.2 degrees), selected from 5.4, 8.8, 10.9, 13.0, 15.1, 16.2, 17.5, 21.9 and 26.3 degrees. In some embodiments, Compound 1 di-hydrochloric acid salt Form IV has at least three X-ray powder diffraction (XRPD) peaks, in terms of 2-theta (±0.2 degrees), selected from 5.4, 8.8, 10.9, 13.0, 15.1, 16.2, 17.5, 21.9 and 26.3 degrees. In some embodiments, Compound 1 di-hydrochloric acid salt Form IV has at least four X-ray powder diffraction (XRPD) peaks, in terms of 2-theta (±0.2 degrees), selected from 5.4, 8.8, 10.9, 13.0, 15.1, 16.2, 17.5, 21.9 and 26.3 degrees. In some embodiments, Compound 1 di-hydrochloric acid salt Form IV has characteristic X-ray powder diffraction (XRPD) peaks, in terms of 2-theta (±0.2 degrees), at 5.4, 8.8, 10.9, 13.0, 15.1, 16.2, 17.5, 21.9 and 26.3 degrees.

Figure 18:
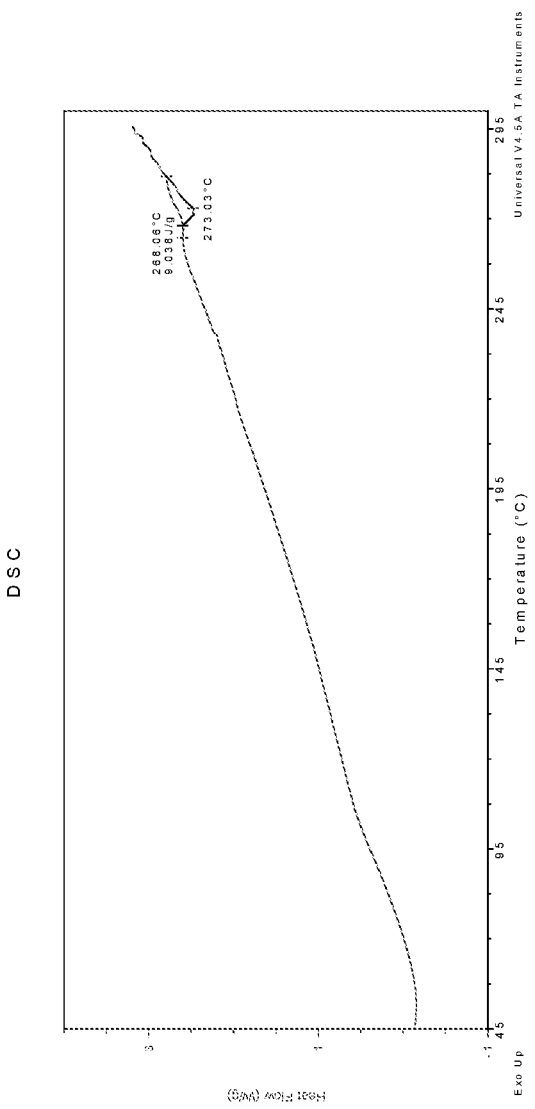
FIG. 18 shows a DSC thermogram of Compound 1 di-hydrochloric acid salt Form IV.
Figure 19:
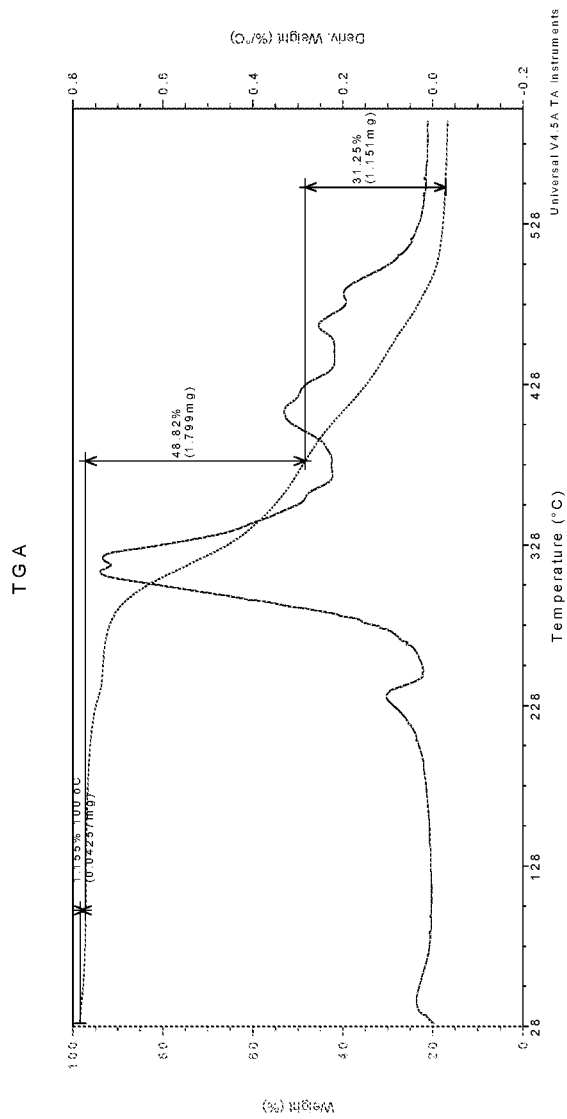
FIG. 19 shows a TGA thermogram of Compound 1 di-hydrochloric acid salt Form IV.
Figure 20:
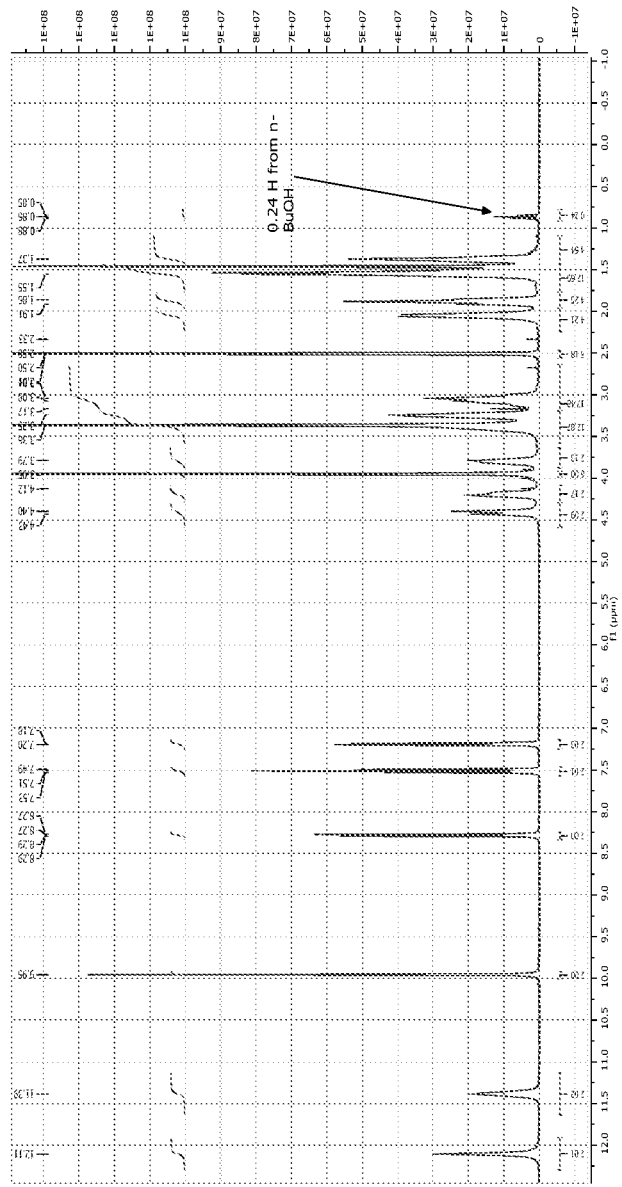
FIG. 20 shows a $^1$H NMR of Compound 1 di-hydrochloric acid salt Form IV in DMSO-d6.

In some embodiments, Compound 1 di-hydrochloric acid salt Form IV exhibits a DSC thermogram having an endothermic peak with an onset temperature of 268±3° C. and a maximum at 273±3° C. In some embodiments, Compound 1 di-hydrochloric acid salt Form IV has a DSC thermogram substantially as depicted in FIG. 18. In some embodiments, Compound 1 di-hydrochloric acid salt Form IV has a TGA thermogram substantially as depicted in FIG. 19. In some embodiments, Compound 1 mono-hydrochloric acid salt Form IV has a NMR spectrum substantially as depicted in FIG. 20.

In some embodiments, Compound 1 di-hydrochloric acid salt has Form V.

In some embodiments, Compound 1 di-hydrochloric acid salt Form V is produced via adding Compound 1 di-hydrochloric acid salt Form I to a saturated or cloudy solution of Compound 1 di-hydrochloric acid salt Form I in a solvent comprising n-propanol, stirring for at least 24 hours (e.g., about 3 days) at about 25° C., and isolating the resulting solid.

Figure 21:
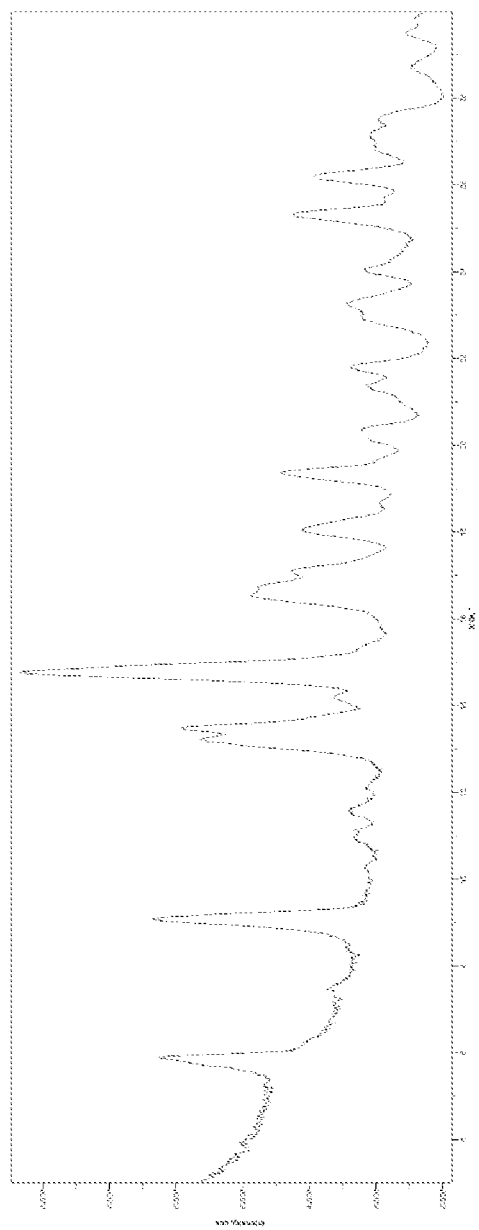
FIG. 21 shows an XRPD pattern of Compound 1 di-hydrochloric acid salt Form V.

In some embodiments, Compound 1 di-hydrochloric acid salt Form V can be characterized by the X-ray powder diffraction (XRPD) pattern substantially as shown in FIG. 21.

In some embodiments, Compound 1 di-hydrochloric acid salt Form V has at least one X-ray powder diffraction (XRPD) peak, in terms of 2-theta (±0.2 degrees), selected from 5.8, 9.1, 13.4, 14.8, 16.6, 17.1, 18.1 and 19.3 degrees. In some embodiments, Compound 1 di-hydrochloric acid salt Form V has at least two X-ray powder diffraction (XRPD) peaks, in terms of 2-theta (±0.2 degrees), selected from 5.8, 9.1, 13.4, 14.8, 16.6, 17.1, 18.1 and 19.3 degrees. In some embodiments, Compound 1 di-hydrochloric acid salt Form V has at least three X-ray powder diffraction (XRPD) peaks, in terms of 2-theta (±0.2 degrees), selected from 5.8, 9.1, 13.4, 14.8, 16.6, 17.1, 18.1 and 19.3 degrees. In some embodiments, Compound 1 di-hydrochloric acid salt Form V has at least four X-ray powder diffraction (XRPD) peaks, in terms of 2-theta (±0.2 degrees), selected from 5.8, 9.1, 13.4, 14.8, 16.6, 17.1, 18.1 and 19.3 degrees. In some embodiments, Compound 1 di-hydrochloric acid salt Form V has characteristic X-ray powder diffraction (XRPD) peaks, in terms of 2-theta (±0.2 degrees), at 5.8, 9.1, 13.4, 14.8, 16.6, 17.1, 18.1 and 19.3 degrees.

Figure 22:
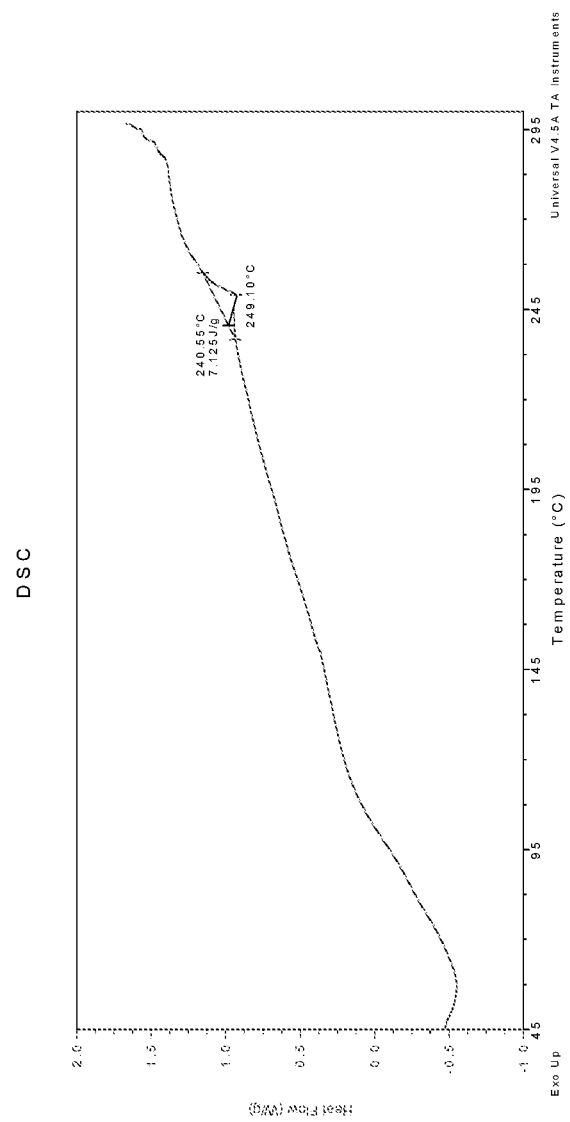
FIG. 22 shows a DSC thermogram of Compound 1 di-hydrochloric acid salt Form V.
Figure 23:
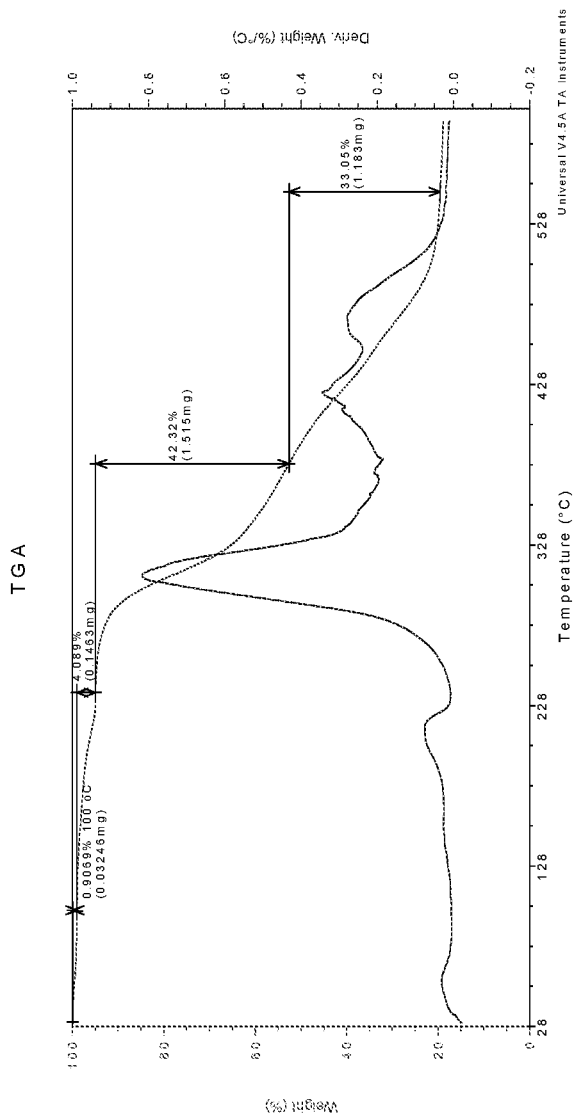
FIG. 23 shows a TGA thermogram of Compound 1 di-hydrochloric acid salt Form V.
Figure 24:
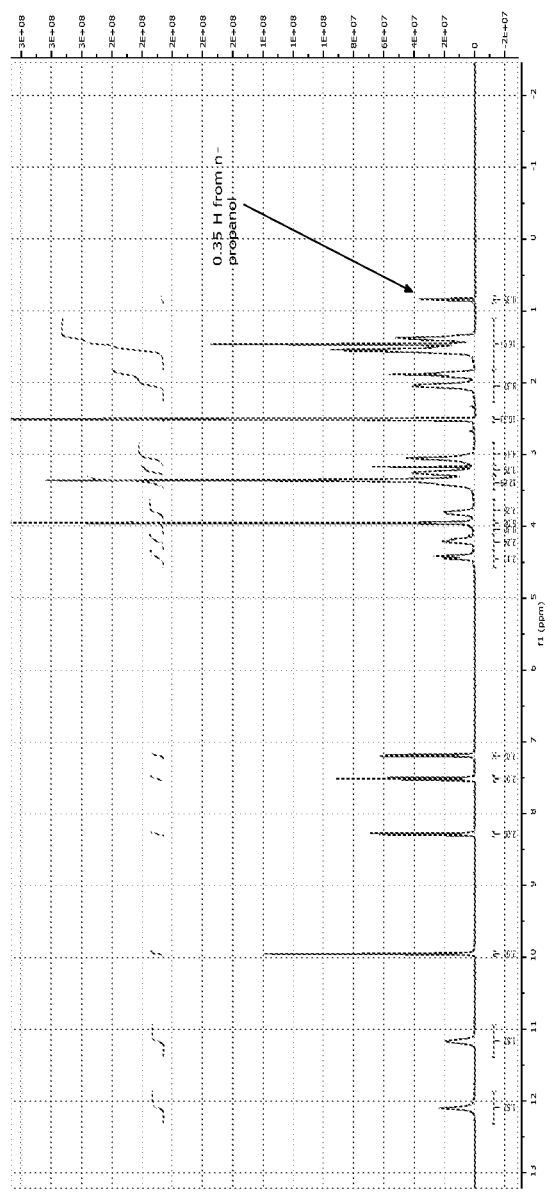
FIG. 24 shows a $^1$H NMR of Compound 1 di-hydrochloric acid salt Form V in DMSO-d6.

In some embodiments, Compound 1 di-hydrochloric acid salt Form V exhibits a DSC thermogram having an endothermic peak with an onset temperature of 241±3° C. and a maximum at 249±3° C. In some embodiments, Compound 1 di-hydrochloric acid salt Form V has a DSC thermogram substantially as depicted in FIG. 22. In some embodiments, Compound 1 di-hydrochloric acid salt Form V has a TGA thermogram substantially as depicted in FIG. 23. In some embodiments, Compound 1 mono-hydrochloric acid salt Form V has a NMR spectrum substantially as depicted in FIG. 24.

In some embodiments, Compound 1 di-hydrochloric acid salt has Form VII.

In some embodiments, Compound 1 di-hydrochloric acid salt Form VII is produced via preparation of a saturated solution of Compound 1 di-hydrochloric acid salt Form I in a solvent comprising about 10% water/acetonitrile at about 50° C., cooling to about 5° C., re-heating to about 50° C., cooling to about 5° C., repeating said previous steps of the process, and isolating the resulting solid.

Figure 29:
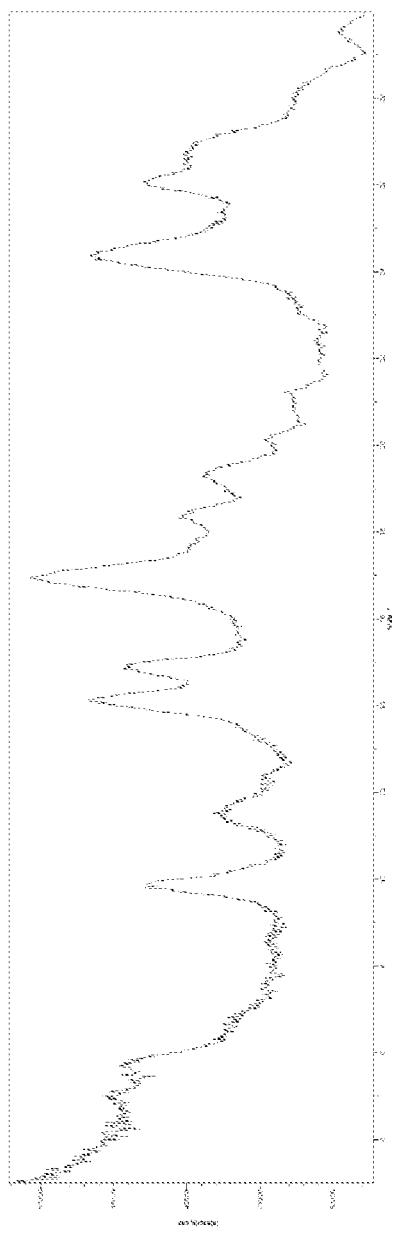
FIG. 29 shows an XRPD pattern of Compound 1 di-hydrochloric acid salt Form VII.

In some embodiments, Compound 1 di-hydrochloric acid salt Form VII can be characterized by the X-ray powder diffraction (XRPD) pattern substantially as shown in FIG. 29.

In some embodiments, Compound 1 di-hydrochloric acid salt Form VII has at least one X-ray powder diffraction (XRPD) peak, in terms of 2-theta (±0.2 degrees), selected from 5.7, 9.9, 11.5, 14.1, 14.9, 17.0 and 24.4 degrees. In some embodiments, Compound 1 di-hydrochloric acid salt Form VII has at least two X-ray powder diffraction (XRPD) peaks, in terms of 2-theta (±0.2 degrees), selected from 5.7, 9.9, 11.5, 14.1, 14.9, 17.0 and 24.4 degrees. In some embodiments, Compound 1 di-hydrochloric acid salt Form VII has at least three X-ray powder diffraction (XRPD) peaks, in terms of 2-theta (±0.2 degrees), selected from 5.7, 9.9, 11.5, 14.1, 14.9, 17.0 and 24.4 degrees. In some embodiments, Compound 1 di-hydrochloric acid salt Form VII has at least four X-ray powder diffraction (XRPD) peaks, in terms of 2-theta (±0.2 degrees), selected from 5.7, 9.9, 11.5, 14.1, 14.9, 17.0 and 24.4 degrees. In some embodiments, Compound 1 di-hydrochloric acid salt Form VII has characteristic X-ray powder diffraction (XRPD) peaks, in terms of 2-theta (±0.2 degrees), at 5.7, 9.9, 11.5, 14.1, 14.9, 17.0 and 24.4 degrees.

Figure 30:
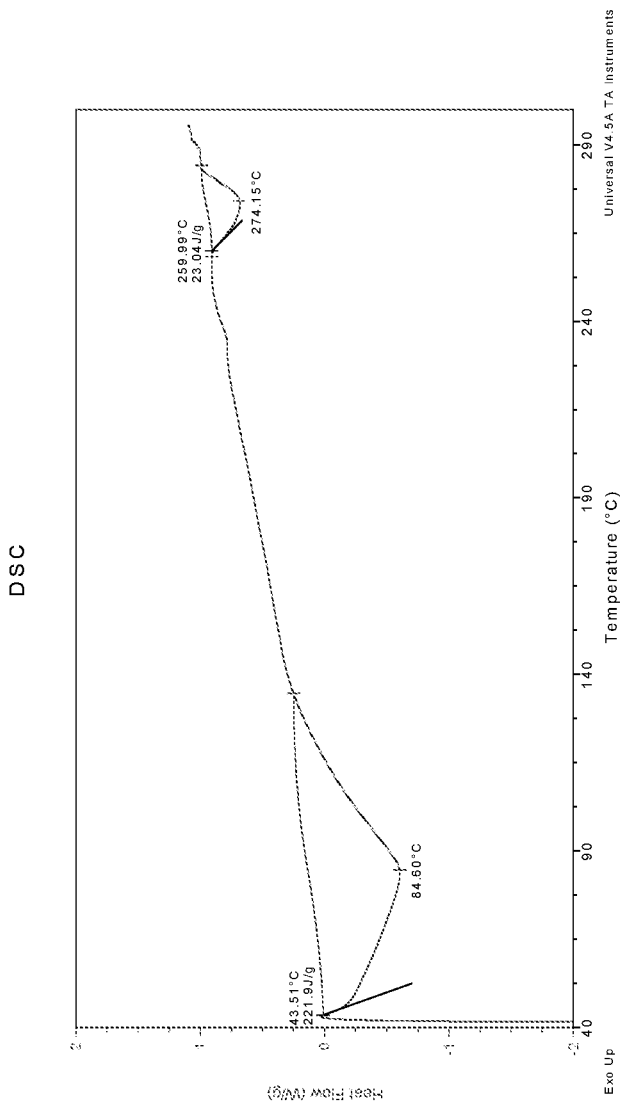
FIG. 30 shows a DSC thermogram of Compound 1 di-hydrochloric acid salt Form VII.
Figure 31:
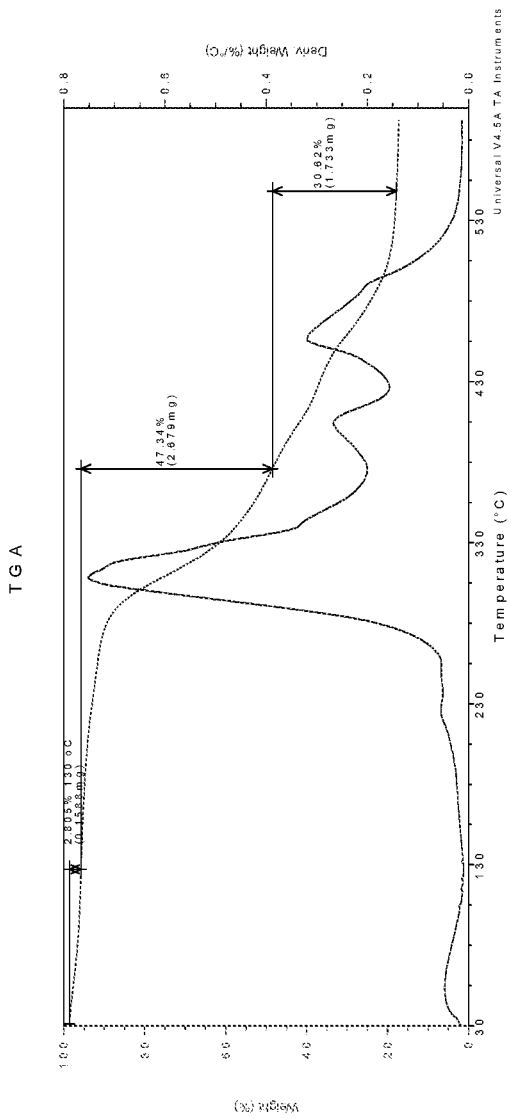
FIG. 31 shows a TGA thermogram of Compound 1 di-hydrochloric acid salt Form VII.
Figure 32:
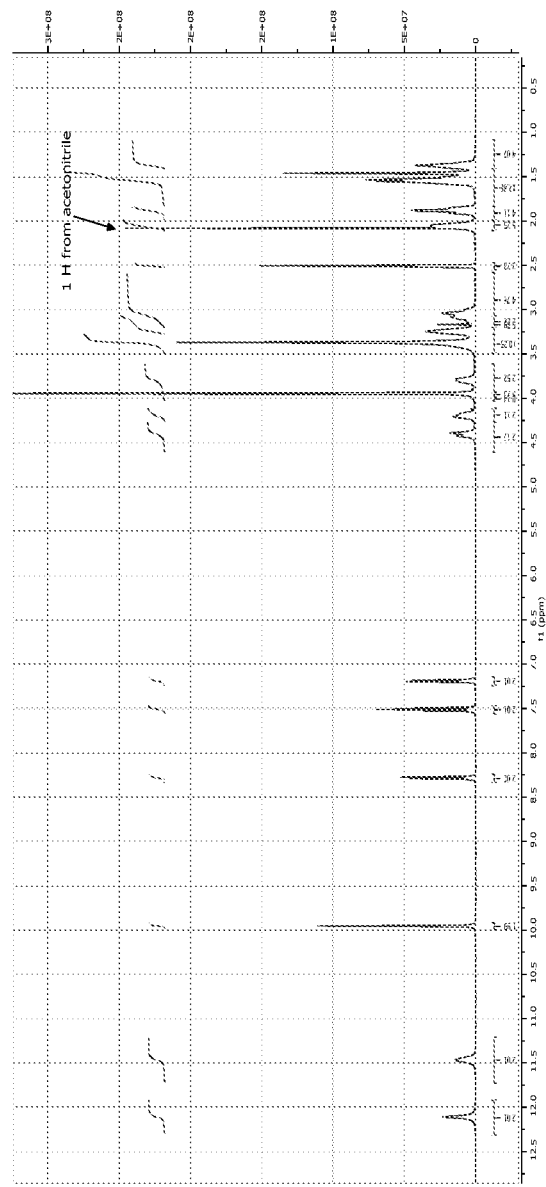
FIG. 32 shows a $^1$H NMR of Compound 1 di-hydrochloric acid salt Form VII in DMSO-d6.

In some embodiments, Compound 1 di-hydrochloric acid salt Form VII exhibits a DSC thermogram having a first endothermic peak with an onset temperature at 44±3° C. and a maximum at 85±3° C., and a second endothermic peak with an onset temperature at 260±3° C. and a maximum at 274±3° C. In some embodiments, Compound 1 di-hydrochloric acid salt Form VII has a DSC thermogram substantially as depicted in FIG. 30. In some embodiments, Compound 1 di-hydrochloric acid salt Form VII has a TGA thermogram substantially as depicted in FIG. 31. In some embodiments, Compound 1 mono-hydrochloric acid salt Form VII has a NMR spectrum substantially as depicted in FIG. 32.

In some embodiments, Compound 1 di-hydrochloric acid salt has Form VIII.

In some embodiments, Compound 1 di-hydrochloric acid salt Form VIII is produced via preparing a saturated or nearly saturated solution of Compound 1 di-hydrochloric acid salt Form I in a solvent comprising methanol, adding the solution to a solvent comprising toluene, and isolating the resulting solid. In some embodiments, Compound 1 di-hydrochloric acid salt Form VIII is produced via preparing a saturated or nearly saturated solution of Compound 1 di-hydrochloric acid salt Form I in a solvent comprising methanol, adding the solution to a solvent comprising isopropyl acetate, and isolating the resulting solid. In some embodiments, Compound 1 di-hydrochloric acid salt Form VIII is produced via preparing a saturated or nearly saturated solution of Compound 1 di-hydrochloric acid salt Form I in a solvent comprising methanol, adding the solution to a solvent comprising ethyl acetate, and isolating the resulting solid.

Figure 33:
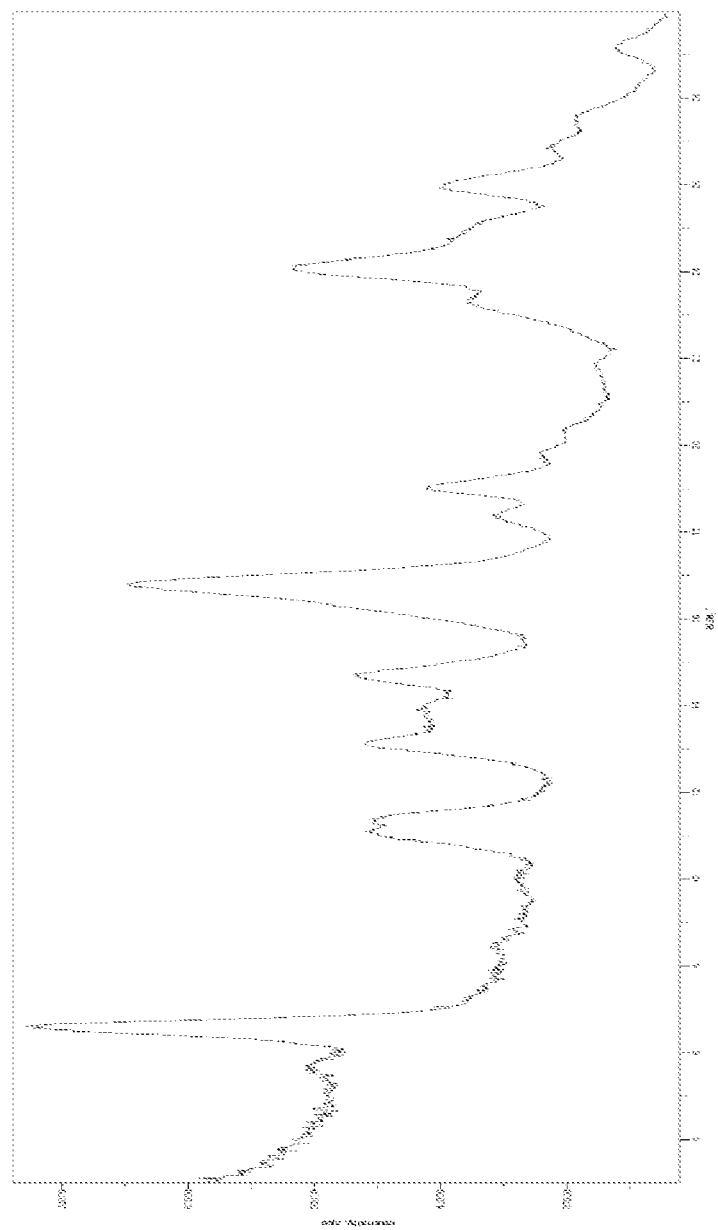
FIG. 33 shows an XRPD pattern of Compound 1 di-hydrochloric acid salt Form VIII.

In some embodiments, Compound 1 di-hydrochloric acid salt Form VIII can be characterized by the X-ray powder diffraction (XRPD) pattern substantially as shown in FIG. 33.

In some embodiments, Compound 1 di-hydrochloric acid salt Form VIII has at least one X-ray powder diffraction (XRPD) peak, in terms of 2-theta (±0.2 degrees), selected from 6.6, 11.2, 13.1, 14.7, 16.7, 19.0 and 24.1 degrees. In some embodiments, Compound 1 di-hydrochloric acid salt Form VIII has at least two X-ray powder diffraction (XRPD) peaks, in terms of 2-theta (±0.2 degrees), selected from 6.6, 11.2, 13.1, 14.7, 16.7, 19.0 and 24.1 degrees. In some embodiments, Compound 1 di-hydrochloric acid salt Form VIII has at least three X-ray powder diffraction (XRPD) peaks, in terms of 2-theta (±0.2 degrees), selected from 6.6, 11.2, 13.1, 14.7, 16.7, 19.0 and 24.1 degrees. In some embodiments, Compound 1 di-hydrochloric acid salt Form VIII has at least four X-ray powder diffraction (XRPD) peaks, in terms of 2-theta (±0.2 degrees), selected from 6.6, 11.2, 13.1, 14.7, 16.7, 19.0 and 24.1 degrees. In some embodiments, Compound 1 di-hydrochloric acid salt Form VIII has characteristic X-ray powder diffraction (XRPD) peaks, in terms of 2-theta (±0.2 degrees), at 6.6, 11.2, 13.1, 14.7, 16.7, 19.0 and 24.1 degrees.

Figure 34:
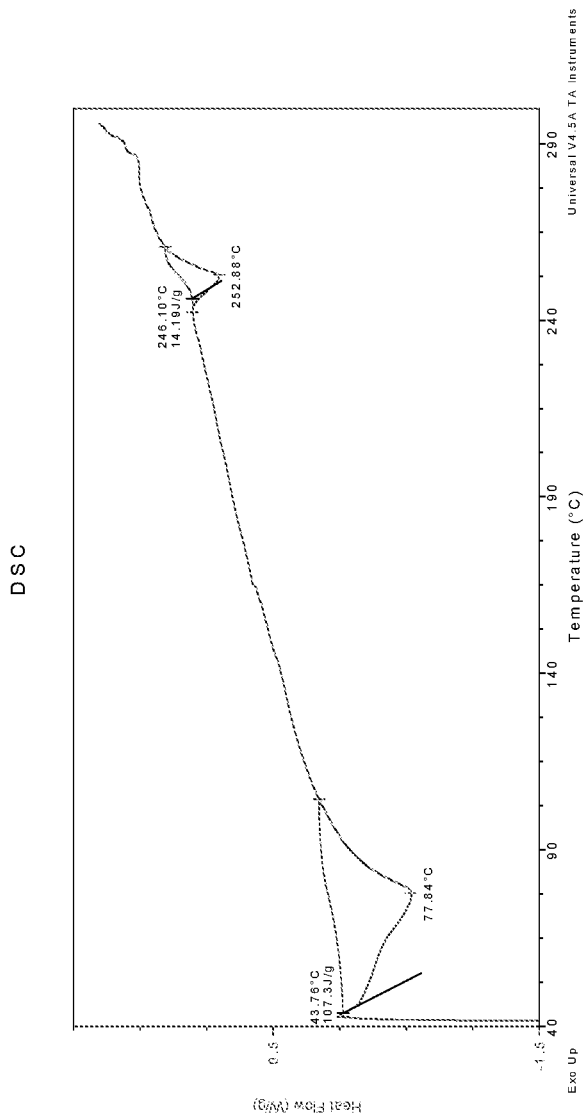
FIG. 34 shows a DSC thermogram of Compound 1 di-hydrochloric acid salt Form VIII.
Figure 35:
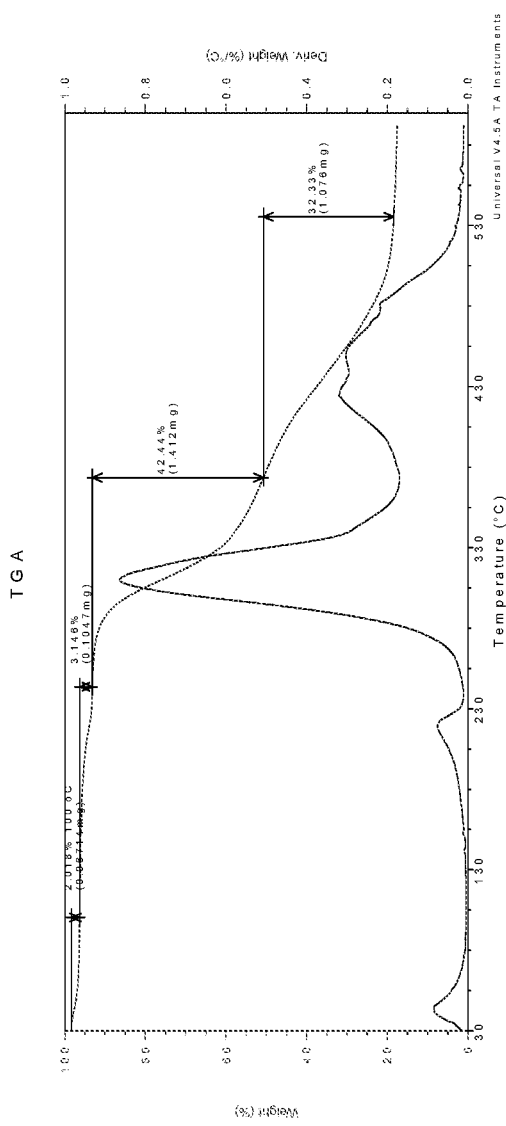
FIG. 35 shows a TGA thermogram of Compound 1 di-hydrochloric acid salt Form VIII.
Figure 36:
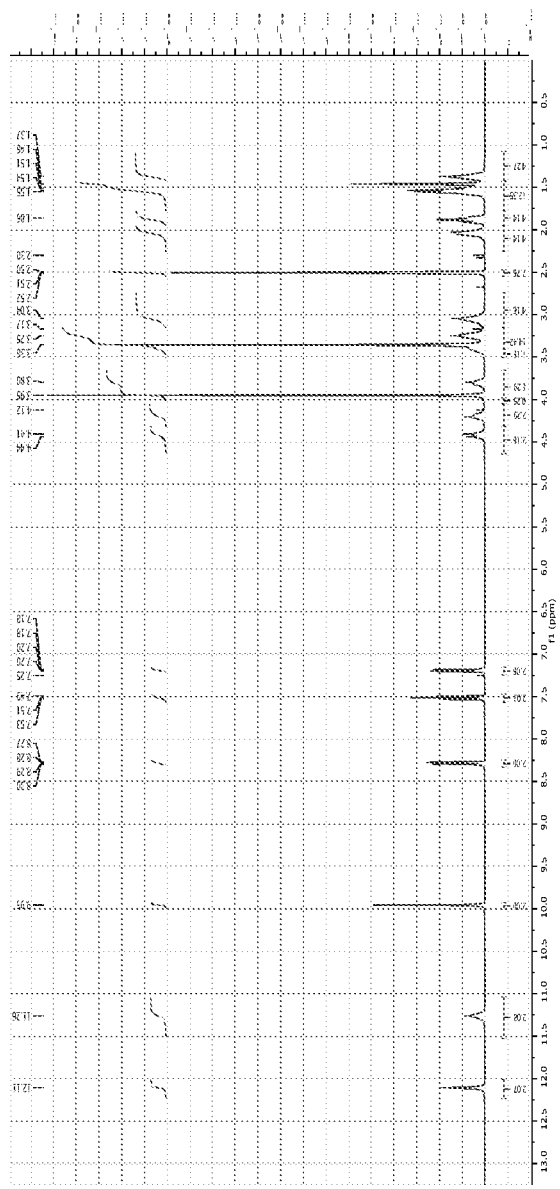
FIG. 36 shows a $^1$H NMR of Compound 1 di-hydrochloric acid salt Form VIII in DMSO-d6.

In some embodiments, Compound 1 di-hydrochloric acid salt Form VIII exhibits a DSC thermogram having a first endothermic peak with an onset temperature at 44±3° C. and a maximum at 78±3° C., and a second endothermic peak with an onset temperature at 246±3° C. and a maximum at 253±3° C. In some embodiments, Compound 1 di-hydrochloric acid salt Form VIII has a DSC thermogram substantially as depicted in FIG. 34. In some embodiments, Compound 1 di-hydrochloric acid salt Form VIII has a TGA thermogram substantially as depicted in FIG. 35. In some embodiments, Compound 1 mono-hydrochloric acid salt Form VIII has a NMR spectrum substantially as depicted in FIG. 36.

In some embodiments, Compound 1 di-hydrochloric acid salt has Form IX.

In some embodiments, Compound 1 di-hydrochloric acid salt Form IX is produced via preparation of a saturated solution of Compound 1 di-hydrochloric acid salt Form I in a solvent comprising methanol at about 50° C., cooling to about 25° C., re-heating the mixture to about 50° C., cooling to about 5° C., repeating the previous process steps, and isolating the resulting solid.

Figure 37:
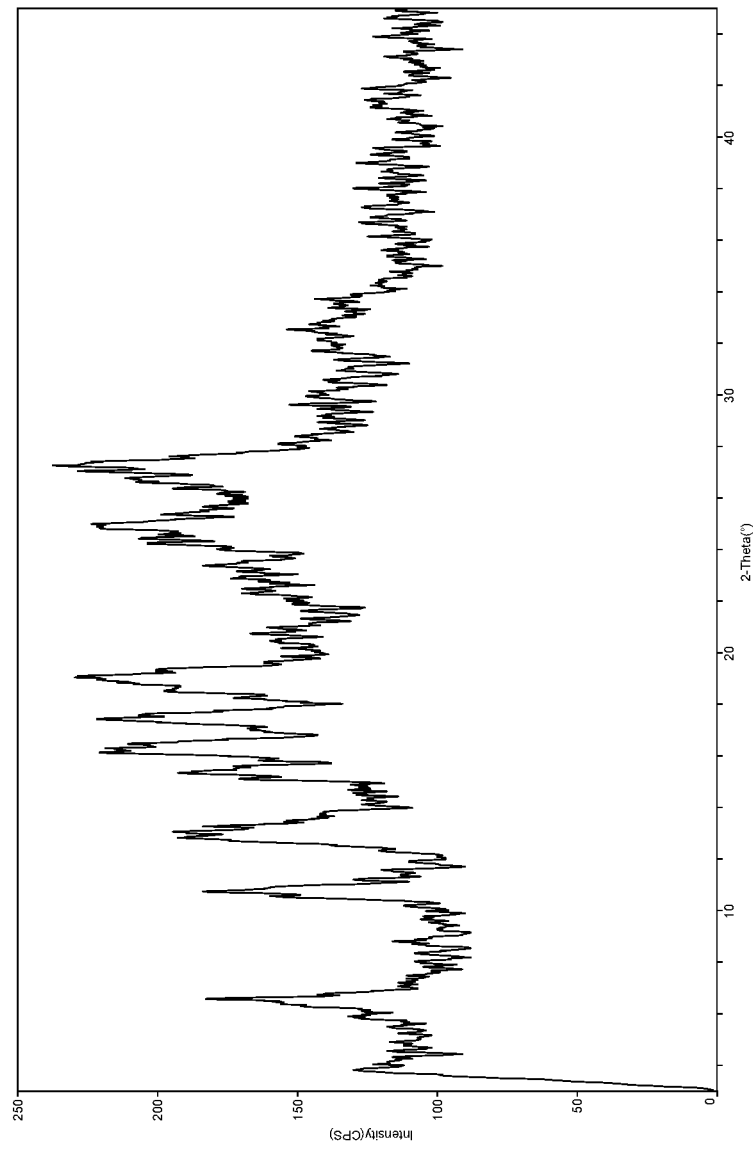
FIG. 37 shows an XRPD pattern of Compound 1 di-hydrochloric acid salt Form IX.

In some embodiments, Compound 1 di-hydrochloric acid salt Form IX can be characterized by the X-ray powder diffraction (XRPD) pattern substantially as shown in FIG. 37.

In some embodiments, Compound 1 di-hydrochloric acid salt Form IX has at least one X-ray powder diffraction (XRPD) peak, in terms of 2-theta (±0.2 degrees), selected from 3.8, 6.6, 10.7, 13.1, 15.3, 16.3, 17.5 and 19.1 degrees. In some embodiments, Compound 1 di-hydrochloric acid salt Form IX has at least two X-ray powder diffraction (XRPD) peaks, in terms of 2-theta (±0.2 degrees), selected from 3.8, 6.6, 10.7, 13.1, 15.3, 16.3, 17.5 and 19.1 degrees. In some embodiments, Compound 1 di-hydrochloric acid salt Form IX has at least three X-ray powder diffraction (XRPD) peaks, in terms of 2-theta (±0.2 degrees), selected from 3.8, 6.6, 10.7, 13.1, 15.3, 16.3, 17.5 and 19.1 degrees. In some embodiments, Compound 1 di-hydrochloric acid salt Form IX has at least four X-ray powder diffraction (XRPD) peaks, in terms of 2-theta (±0.2 degrees), selected from 3.8, 6.6, 10.7, 13.1, 15.3, 16.3, 17.5 and 19.1 degrees. In some embodiments, Compound 1 di-hydrochloric acid salt Form IX has characteristic X-ray powder diffraction (XRPD) peaks, in terms of 2-theta (±0.2 degrees), at 3.8, 6.6, 10.7, 13.1, 15.3, 16.3, 17.5 and 19.1 degrees.

Figure 38:
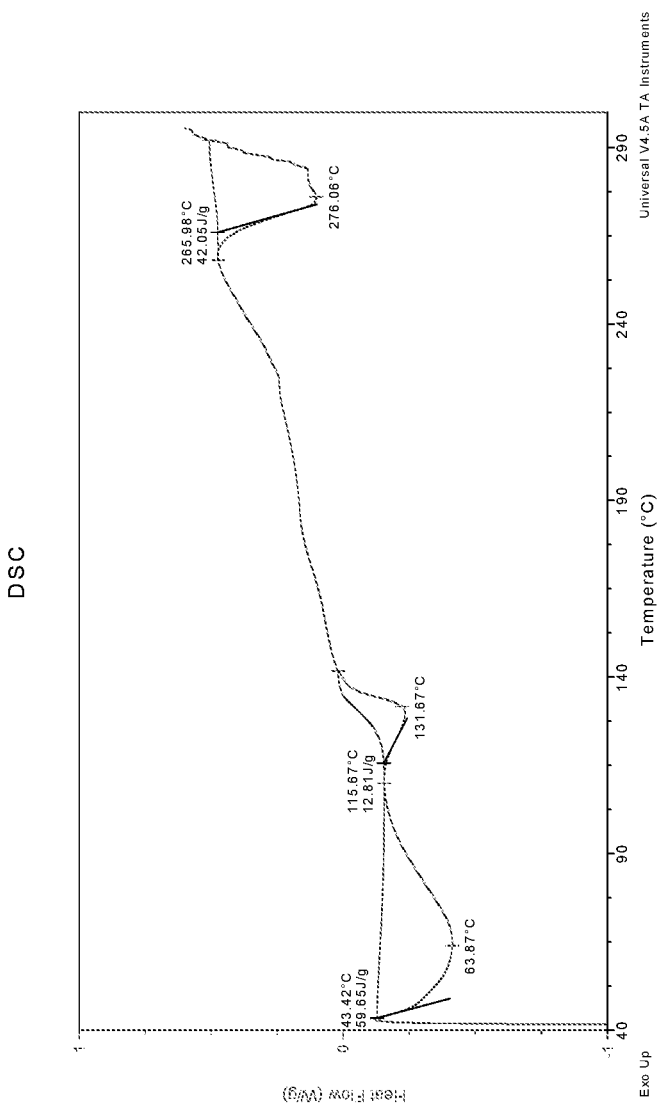
FIG. 38 shows a DSC thermogram of Compound 1 di-hydrochloric acid salt Form IX.
Figure 39:
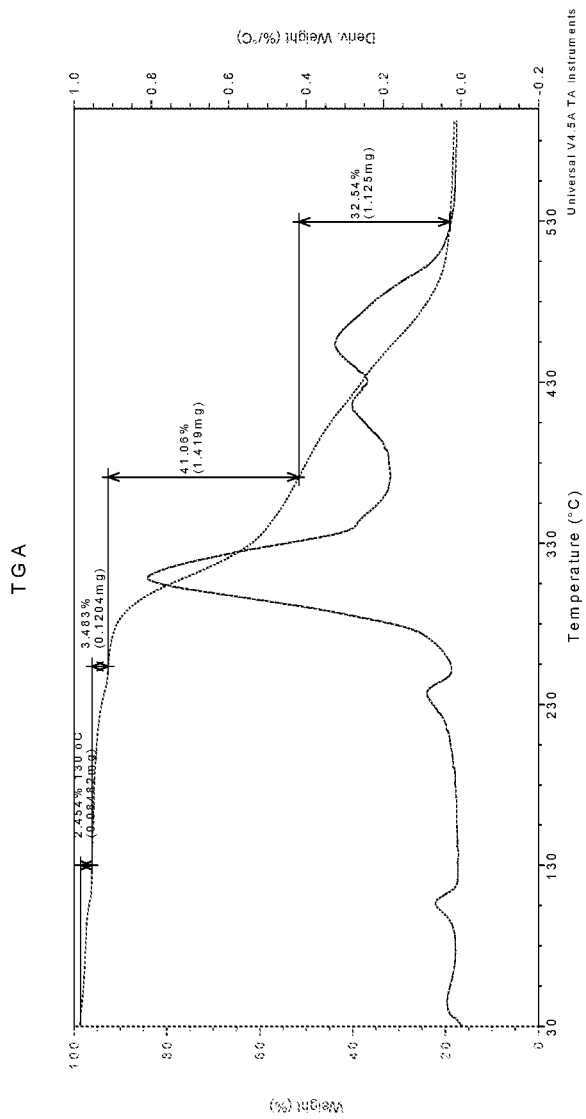
FIG. 39 shows a TGA thermogram of Compound 1 di-hydrochloric acid salt Form IX.

In some embodiments, Compound 1 di-hydrochloric acid salt Form IX exhibits a DSC thermogram having a first endothermic peak with an onset temperature at 43±3° C. and a maximum at 64±3° C., and a second endothermic peak at 116±3° C. and a maximum at 132±3° C., and a third endothermic peak at 266±3° C. and a maximum at 276±3° C. In some embodiments, Compound 1 di-hydrochloric acid salt Form IX has a DSC thermogram substantially as depicted in FIG. 38. In some embodiments, Compound 1 di-hydrochloric acid salt Form IX has a TGA thermogram substantially as depicted in FIG. 39.

Synthetic Processes

Compound 1, including salts thereof, can be prepared using known organic synthesis techniques and can be synthesized according to any of numerous possible synthetic routes. Compound 1 is described in U.S. patent application Ser. No. 16/409,026, the entirety of which is incorporated herein by reference.

The reactions for preparing Compound 1 can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of Compound 1 can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry; Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, vivo-butyl alcohol, tert-butyl alcohol, 2-ethoxy ethanol, di ethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran, acetonitrile, N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Compound 1 can be synthesized using a process shown in Scheme 1. Boc-protected compound 1-1 can be deprotected under acidic conditions (e.g., hydrochloric acid or trifluoroacetic acid) to provide amine 1-2. Palladium-catalyzed cross-coupling reaction of halo-substituted compound 1-2 with a boronic ester of formula 1-3 under standard conditions (such as Suzuki coupling reaction, e.g., in the presence of a palladium catalyst and a suitable base) can produce a compound of formula 1-4. The reaction of amine 1-4 with methyl 4-(2-oxoethyl)bicyclo[2.2.1]heptane-1-carboxylate 1-5 under reductive amination conditions (e.g, sodium triacetoxyborohydride or sodium cyanoborohydride as the reducing reagent) to generate a compound of formula 1-6. After removal of the Boc group of compound 1-6 under acidic conditions (e.g., hydrochloric acid or trifluoroacetic acid), the second ethane-2,1-diyl(bicyclo[2.2.1]heptane-1-carboxylic ester) group can be introduced to the resulting amine by reductive amination with the corresponding aldehydes or ketones to generate a compound of formula 1-7. Then ester 1-7 can be hydrolyzed under alkaline conditions to provide the desired Compound 1.

A compound of formula 1-1 can be synthesized using a process shown in Scheme 2. The free amine in compound 2-1 can be protected with Boc. The resulting compound can be deprotonated by a strong base such as, but not limited to, n-butyl lithium to generate the corresponding heteroaryl lithium intermediate, which can further react with an alkyl- chloroformate to give esters of formula 2-2. The reaction of ester 2-2 with halo-substituted aniline 2-3 in the presence of a suitable base such as, but not limited to, potassium tert-butoxide can furnish the desired compound of formula 1-1.

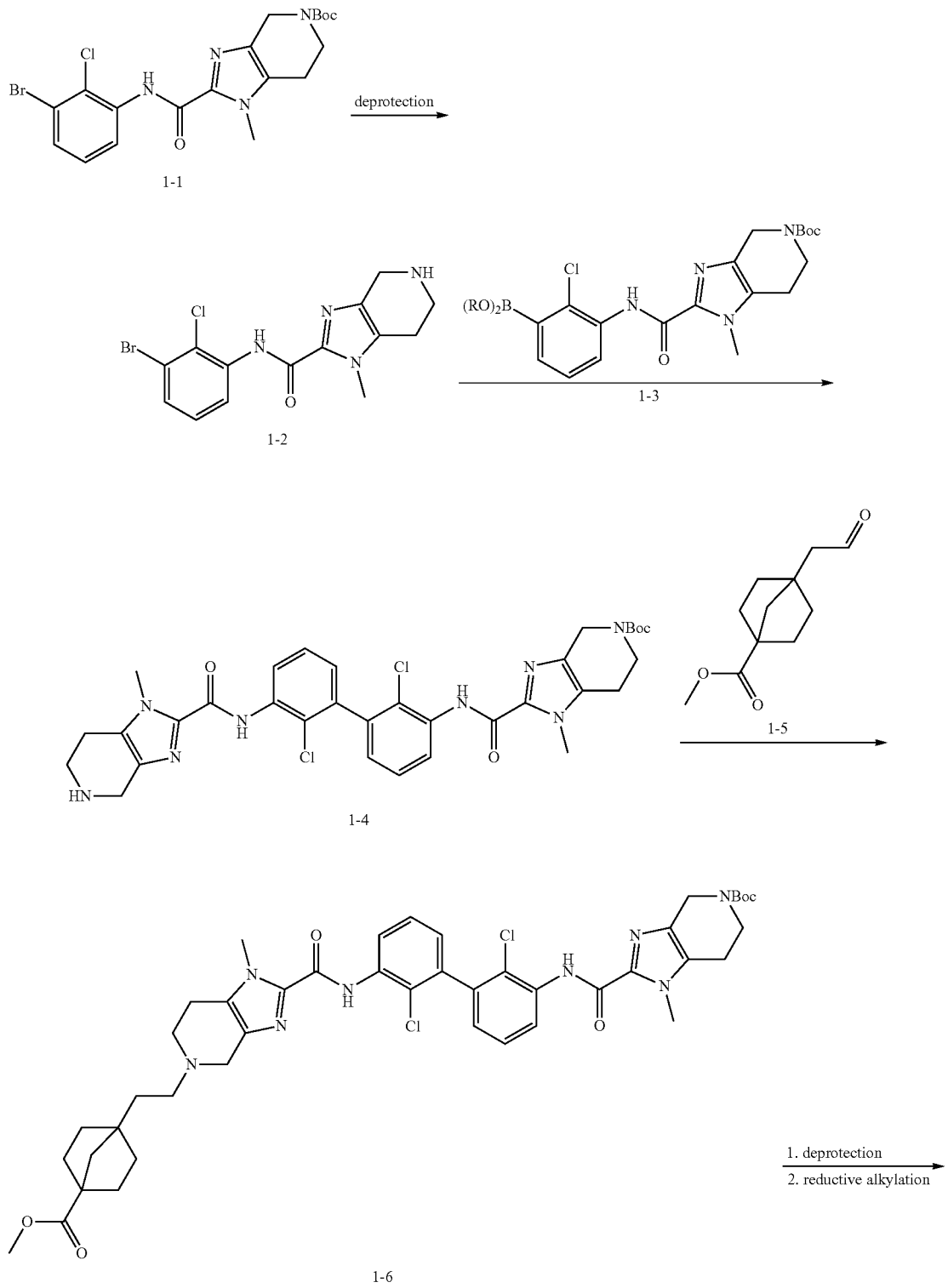

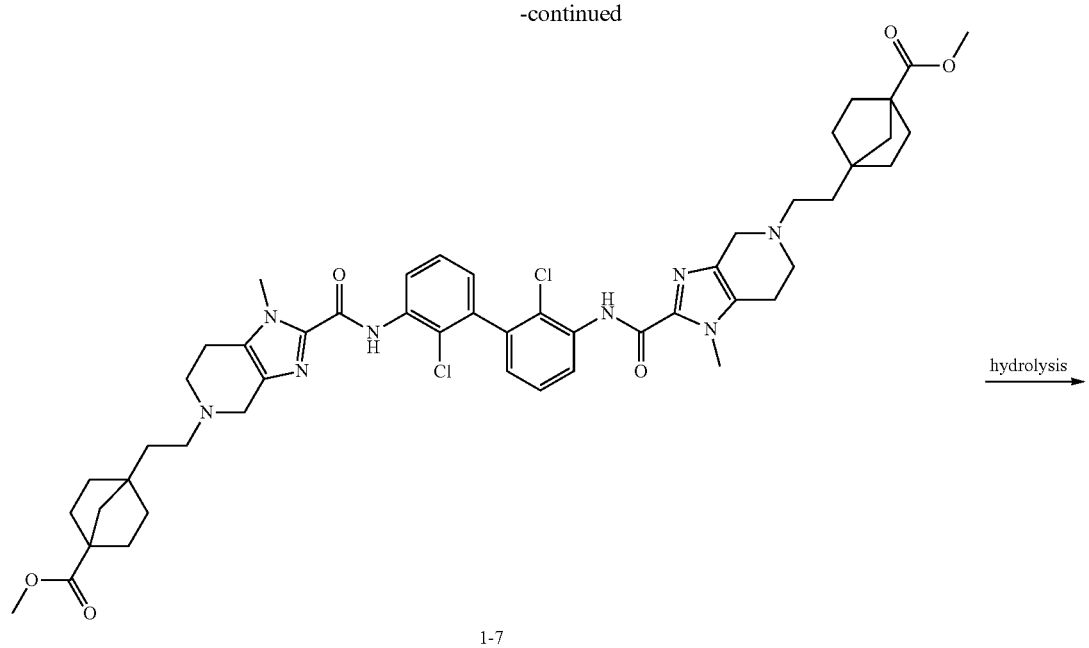
1-7
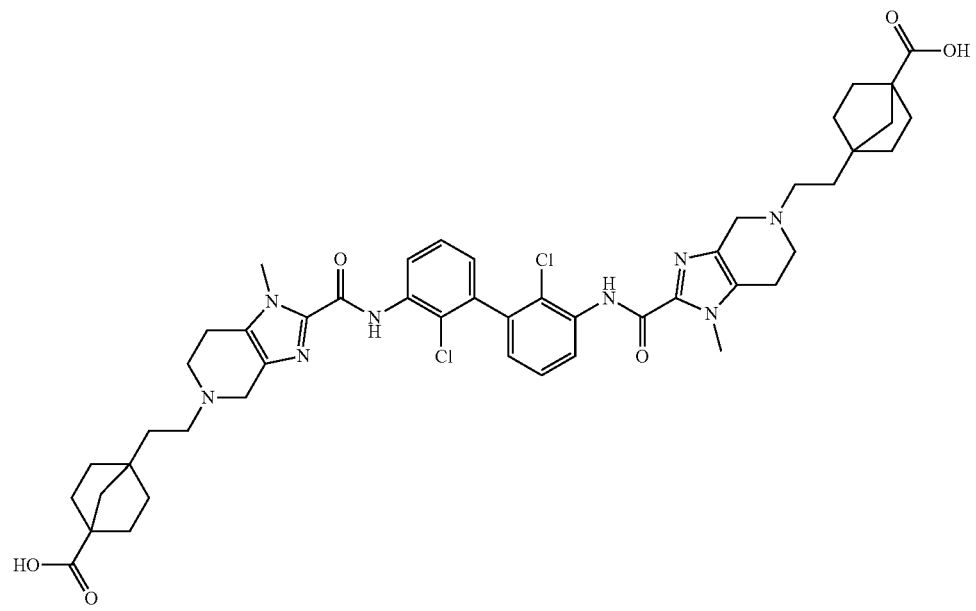
Compound 1
Scheme 2
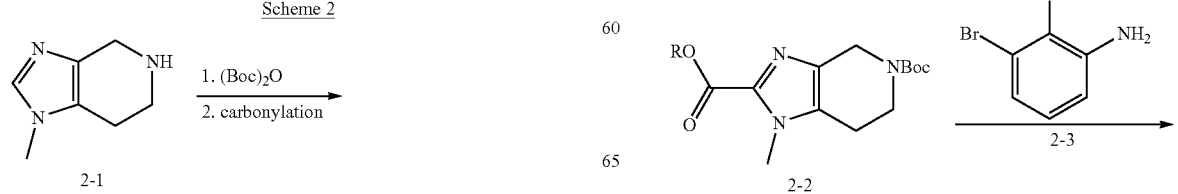

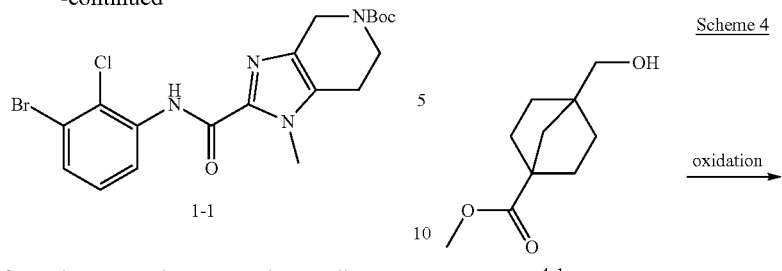

A compound of formula 1-3 can be prepared according to Scheme 3. Halo-substituted compound 1-1 can be converted to the boronic ester 1-3 under standard conditions [e.g., in the presence of bis(pinacolato)diboron and a palladium catalyst, such as, tetrakis(triphenylphosphine) palladium(O) and palladium(II) acetate],

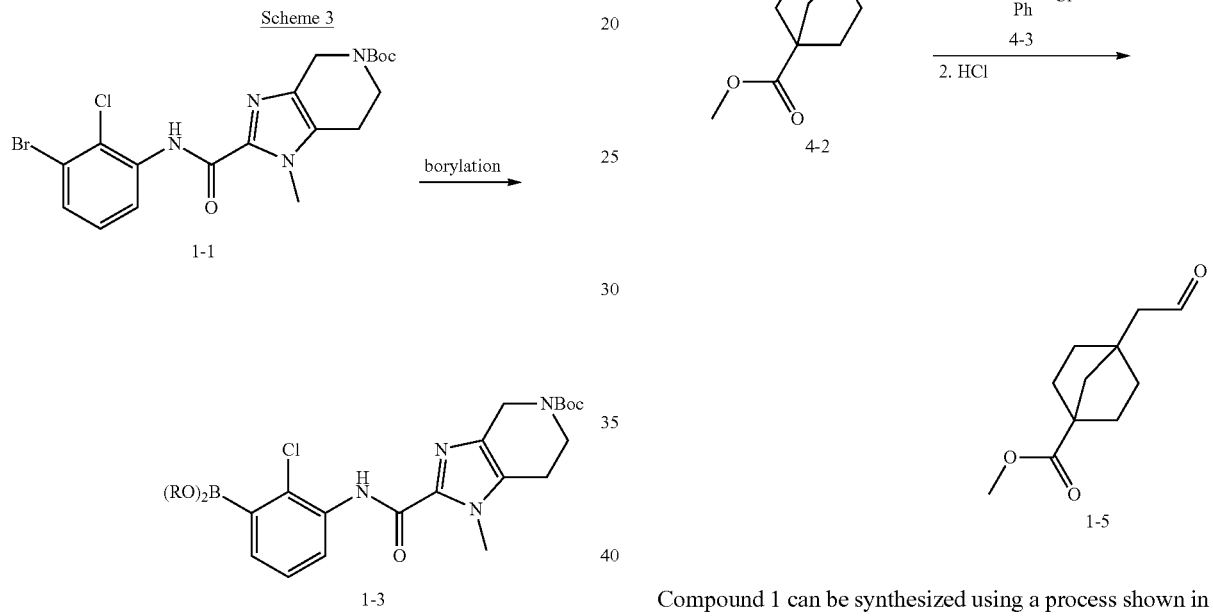

Compound 1-5 can be prepared according to Scheme 4. Alcohol 4-1 can be converted to aldehyde 4-2 in the presence of an oxidant such as, but not limited to, Dess-Martin periodinane or pyridinium chlorochromate. Aldehyde 4-2 can be extended by one carbon atom in a Wittig reaction with (methoxymethyl)triphenylphosphonium chloride 4-3 to form an enol ether, which can be further hydrolyzed under acidic conditions (e.g., hydrochloric acid) to provide the desired compound 1-5.

Compound 1 can be synthesized using a process shown in Scheme 5. The reaction of Compound 5-2 with Compound 5-1 in the presence of a suitable base such as, but not limited to, potassium tert-butoxide can furnish the desired Compound 5-3. After removal of the Boc group of compound 5-3 under acidic conditions to give Compound 5-5 (e.g., hydrochloric acid or trifluoroacetic acid), neutralization with a base gives Compound 5-6. The ethane-2,1-diyl(bicyclo [2.2.1]heptane-1-carboxylic acid groups can be introduced to the resulting diamine by reductive amination with Compound 5-4 to generate Compound 1.

Scheme 5

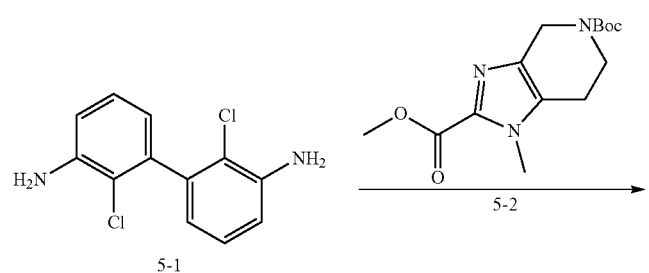

-continued

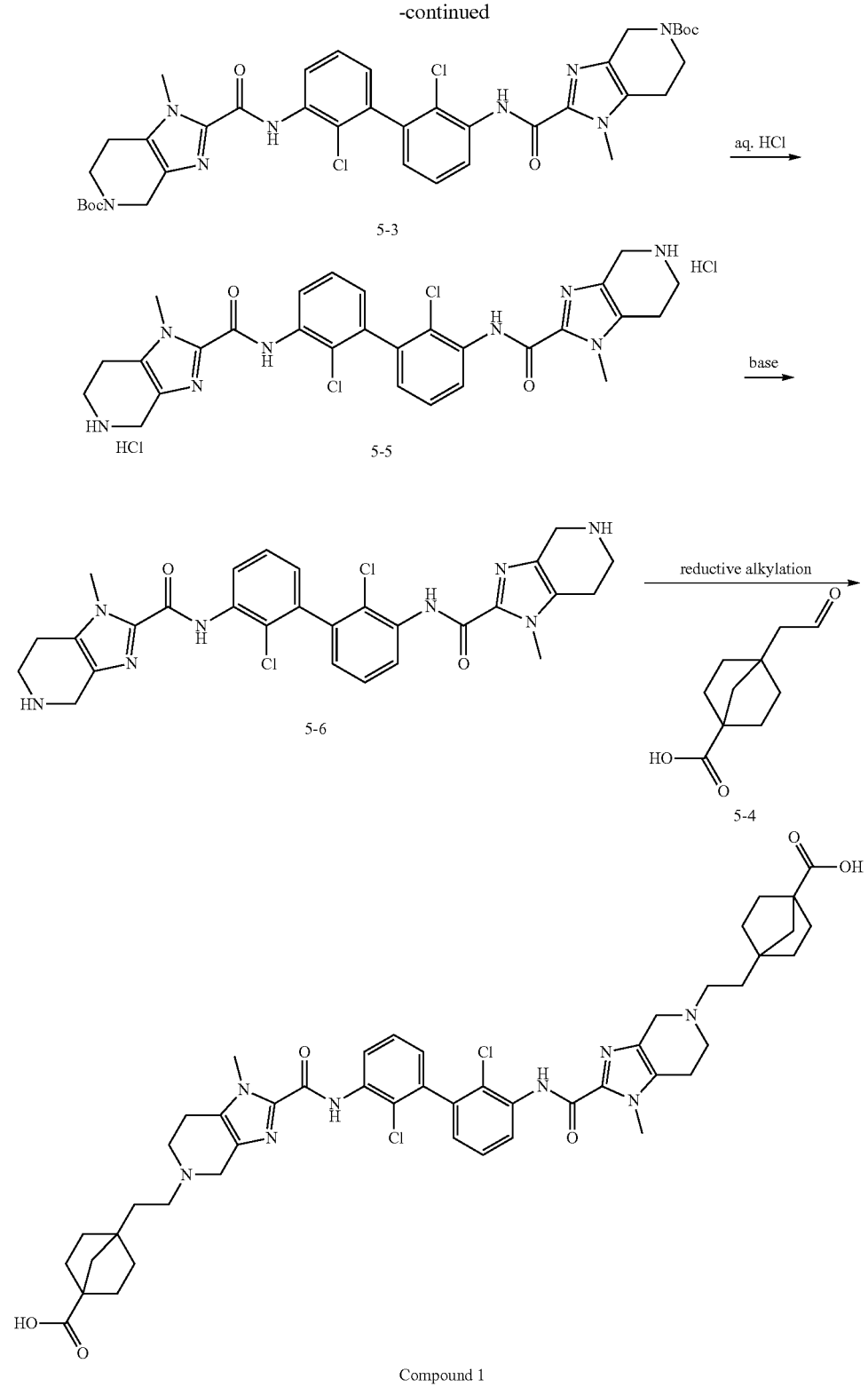

Compound 1

A compound of formula 5-1 can be prepared according to Scheme 6. Compound 2-3 can be converted to the boronic ester 6-1 under standard conditions [e.g., in the presence of bis(pinacolato)diboron and a palladium catalyst, such as, tetrakis(triphenylphosphine) palladium(O) and palladium (II) acetate]. Palladium-catalyzed cross-coupling reaction of compound 2-3 with a boronic ester of formula 6-1 under standard conditions (such as Suzuki coupling reaction, e.g., in the presence of a palladium catalyst and a suitable base) can produce a compound of formula 5-1.

Scheme 6

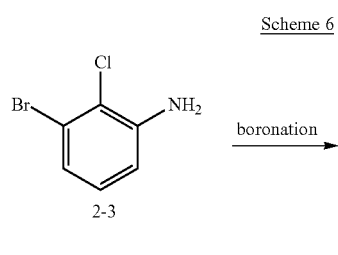

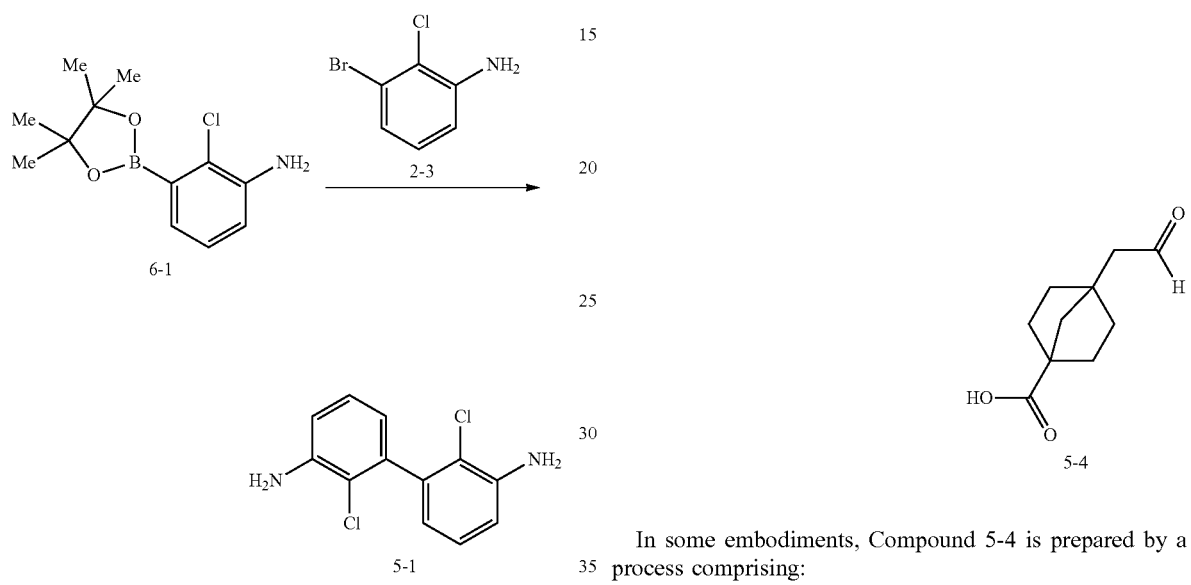

Scheme 7

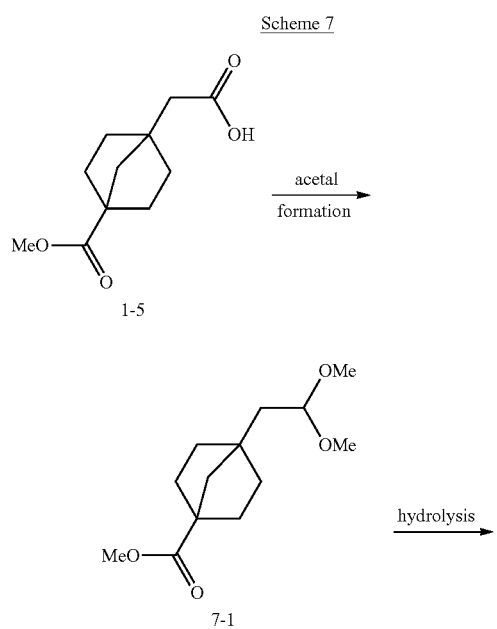

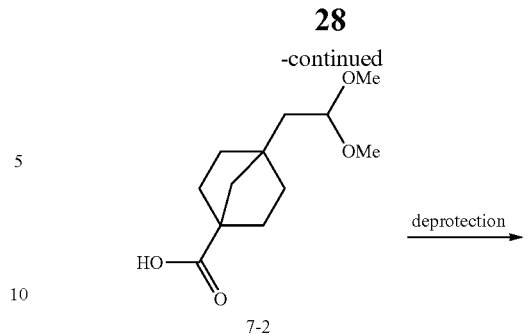

In some embodiments, Compound 5-4 is prepared by a process comprising:

converting Compound 1-5 to Compound 7-1;

converting Compound 7-1 to Compound 7-2; and converting Compound 7-2 to Compound 5-4.

In some embodiments, Compound 7-1 is prepared by a process comprising converting Compound 1-5 to Compound 7-1. In some embodiments, the converting of Compound 1-5 to Compound 7-1 is carried out in the presence of trimethyl orthoformate and an acid, such as, p-toluenesulfonic acid.

In some embodiments, Compound 7-2 is prepared by a process comprising converting Compound 7-1 to Compound 7-2. In some embodiments, the converting comprises hydrolysis of Compound 7-1.

In some embodiments, Compound 5-4 is prepared by a process comprising converting Compound 7-2 to Compound 5-4. In some embodiments, the converting comprises deprotecting Compound 7-2.

Compound 1 and Compound 1 di-hydrochloric acid salt can be synthesized using a process shown in Scheme 8. Removal of the Boc group of compound 5-3 under acidic conditions (e.g., hydrochloric acid or trifluoroacetic acid) followed by neutralization with a base gives Compound 5-6. The ethane-2,1-diyl(bicyclo[2.2.1]heptane-1-carboxylic acid groups can be introduced to the resulting diamine by reductive amination with Compound 5-4 to generate Compound 1. Crude Compound 1 di HCl salt can be formed via exposure of Compound 1 to aqueous HCl. Recrystallization of Crude Compound 1 di-hydrochloric acid salt in e.g., water and acetone, can be used to form the Compound 1 di-hydrochloric acid.

Scheme 8
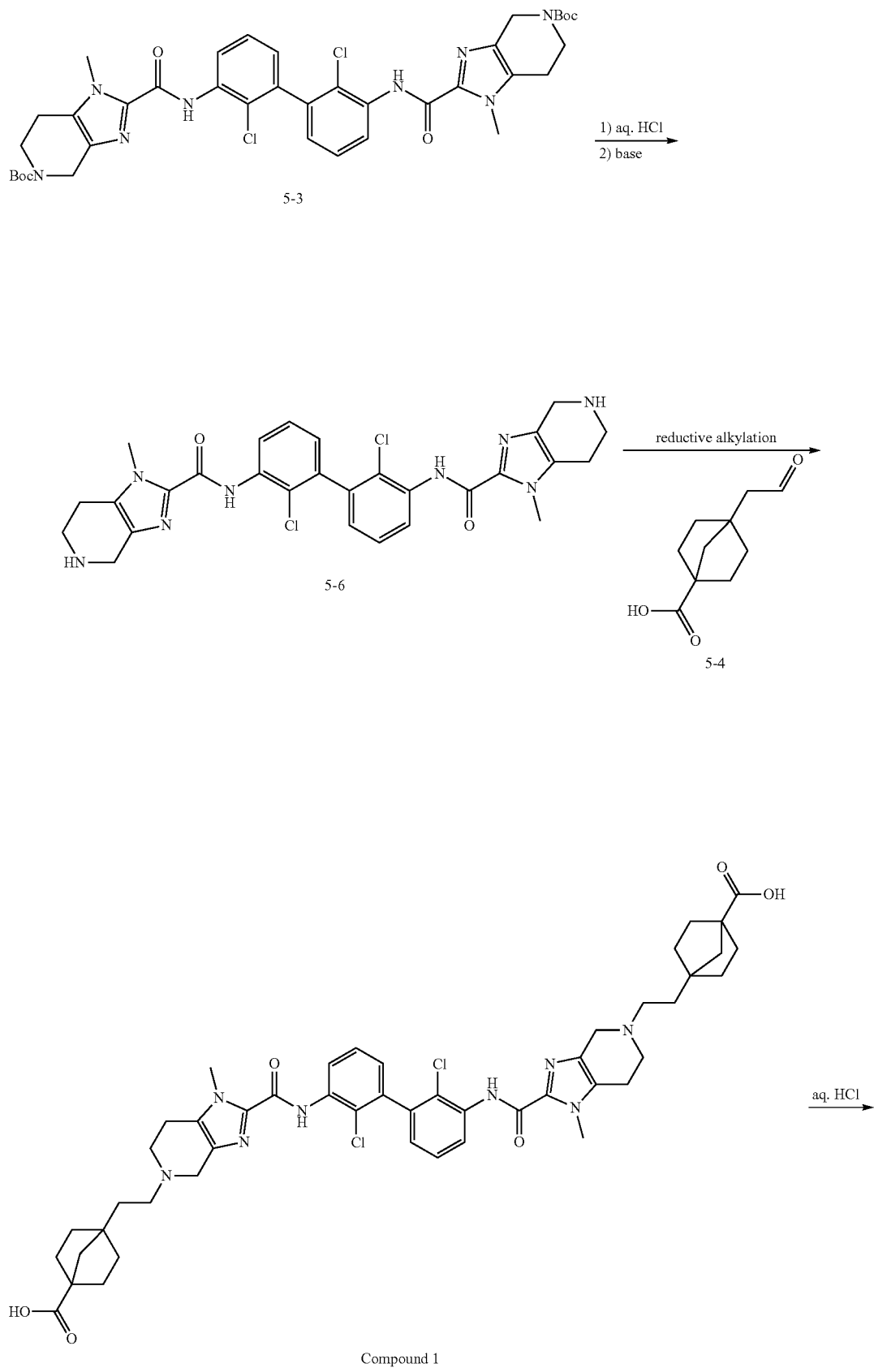

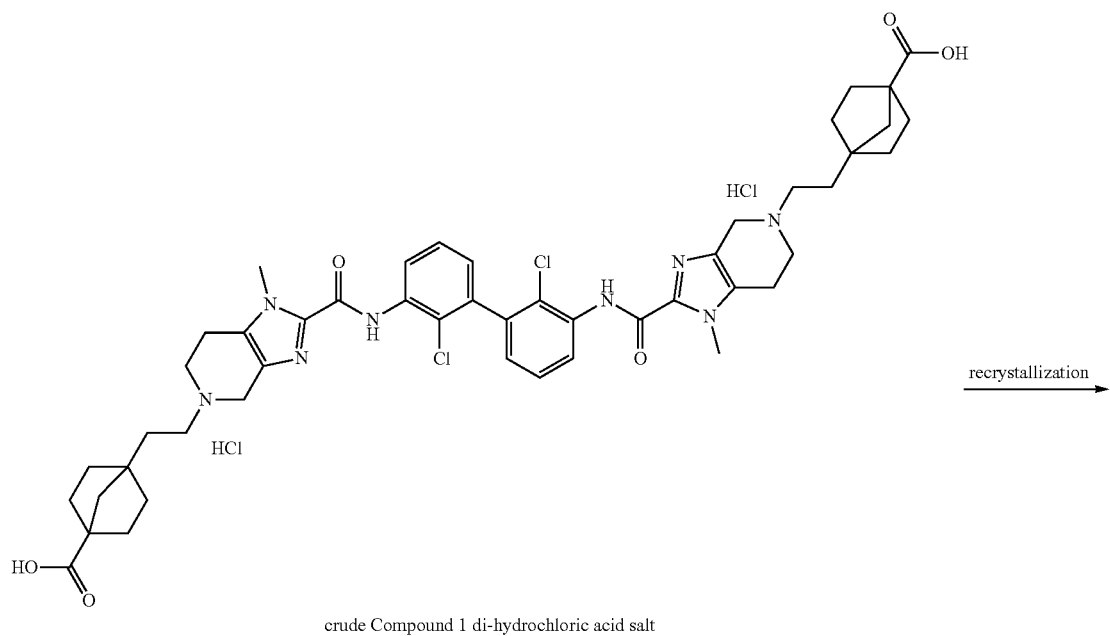
crude Compound 1 di-hydrochloric acid salt
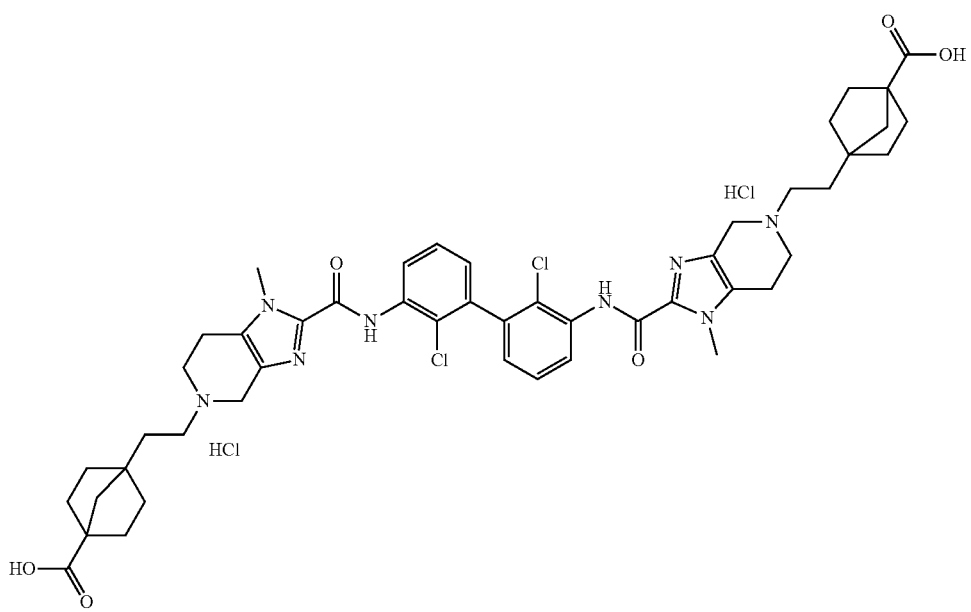
Compound 1 di-hydrochloric acid salt Accordingly, the present disclosure further provides a process of preparing Compound 1, or a salt thereof, comprising:

reacting Compound 5-6:

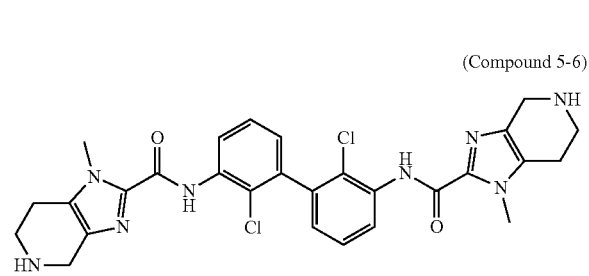 [SMILES: Cn1c(C(=O)Nc2cccc(-c3cccc(NC(=O)c4nc5c(n4C)CCNC5)c3Cl)c2Cl)nc2c1CCNC2]

(Compound 5-6)

with 4-(2-oxoethyl)bicyclo[2.2.1]heptane-1-carboxylic acid (Compound 5-4):

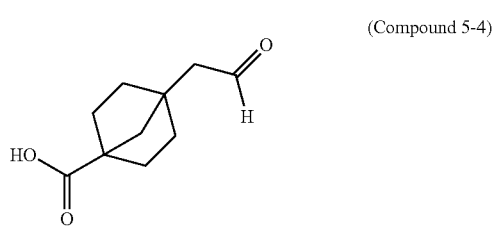 [SMILES: O=CCC12CCC(C(=O)O)(CC1)C2]

(Compound 5-4)

in the presence of a reducing agent to form said Compound 1, or salt thereof.

In some embodiments, said reducing agent is a borohydride reducing agent (e.g., NaB(OAc)$_3$H, NaBH$_4$, or other boron containing hydride reducing agent). In some embodiments, the reducing agent is sodium triacetoxyborohydride. In some embodiments, the reacting is in the presence of a protic acid. In some embodiments, the protic acid is trifluoroacetic acid, hydrochloric acid, or hydrobromic acid. In some embodiments, the protic acid is trifluoroacetic acid.

In some embodiments, the reacting is in a solvent. In some embodiments, the solvent comprises a polar aprotic solvent. In some embodiments, the solvent comprises dichloromethane. In some embodiments, the solvent does not comprise dichloro methane. In some embodiments, the solvent comprises acetonitrile. In some embodiments, the solvent comprises water. In some embodiments, the reacting of Compound 5-6 with Compound 5-4 comprises using about 2 to about 4 molar equivalents of Compound 5-4 relative to Compound 5-6, or about 3 molar equivalents of Compound 5-4 relative to Compound 5-6. In some embodiments, the reacting of Compound 5-6 with Compound 5-4 comprises using about 2 to about 4 molar equivalents of sodium triacetoxyborohydride relative to Compound 5-6, or about 3 molar equivalents of sodium triacetoxyborohydride relative to Compound 5-6.

In some embodiments, Compound 5-6 is prepared by a process comprising:

deprotecting Compound 5-3a:

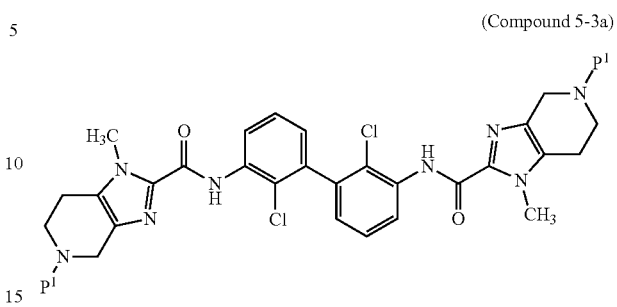

(Compound 5-3a)

to form Compound 5-6, wherein P$^1$ is an amine protecting group.

Appropriate P$^1$ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, P$^1$ is benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenyl sulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP). In some embodiments, P$^1$ is BOC.

In some embodiments, the deprotecting comprises reacting with hydrochloric acid in a solvent, followed by reaction with a base to form said Compound 5-6. In some embodiments, the hydrochloric acid is aqueous hydrochloric acid solution. In some embodiments, the solvent is an alcohol. In some embodiments, the alcohol can be a C$_{1-6}$ alkyl-OH such as methanol. In some embodiments, the reacting is carried out at a temperature of from about 20° C. to about 70° C., from about 25° C. to about 60° C., from about 30° C. to about 60° C., or from about 50° C. to about 55° C.

In some embodiments, the deprotecting comprises reacting said Compound 5-3a with hydrochloric acid in a solvent, followed by reaction with an alkaline carbonate in a solvent comprising water and THF to form said Compound 5-6.

In some embodiments, the deprotecting comprises reacting said Compound 5-3a with hydrochloric acid in a solvent comprising methanol, followed by reaction with a sodium bicarbonate in a solvent comprising water and THF to form said Compound 5-6.

In some embodiments, the deprotecting comprises:
reacting of said Compound 5-3a with hydrochloric acid in a solvent to form Compound 5-5:

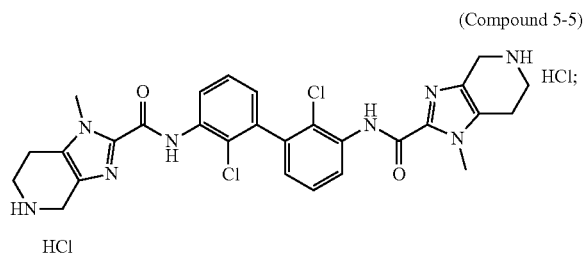 [SMILES: Cn1c(C(=O)Nc2cccc(-c3cccc(NC(=O)c4nc5c(n4C)CCNC5)c3Cl)c2Cl)nc2c1CCNC2 ; Cl]

(Compound 5-5)

neutralizing said Compound 5-5 with base to form said Compound 5-6.

In some embodiments, the Compound 5-3a is Compound 5-3:

(Compound 5-3)

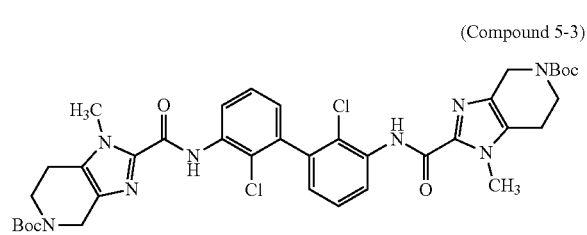 [SMILES: Cn1c(C(=O)Nc2cccc(-c3cccc(NC(=O)c4nc5c(n4C)CCN(C(=O)OC(C)(C)C)C5)c3Cl)c2Cl)nc2c1CCN(C(=O)OC(C)(C)C)C2]

In some embodiments, said Compound 5-3a is prepared by a process comprising:
reacting Compound 5-2a:

(Compound 5-2a)

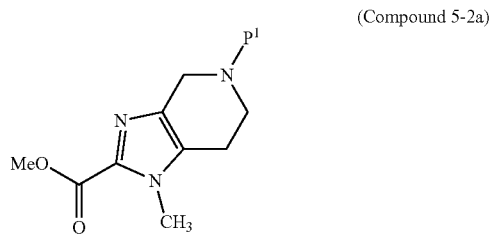

with Compound 5-1:

(Compound 5-1)

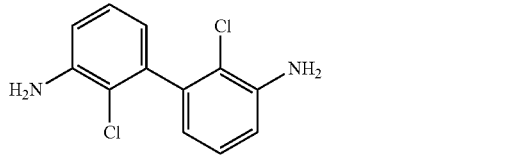

in the presence of a base in a solvent to form said Compound 5-3a, wherein $P^1$ is an amine protecting group.

In some embodiments, the base is an alkaline metal base. In some embodiments, the base is an alkaline alkoxide. In some embodiments, the base is potassium 2-methylpropan-2-olate. In some embodiments, the reacting of Compound 5-2a with Compound 5-1 is carried out in the presence of a solvent. In some embodiment, the solvent comprises a polar aprotic solvent such as tetrahydrofuran. In some embodiments, the reacting of Compound 5-2a with Compound 5-1 comprises using about 2 to about 4 molar equivalents of Compound 5-2a relative to Compound 5-1, about 2 to about 3 molar equivalents of Compound 5-2a relative to Compound 5-1, or about 2.5 molar equivalents of Compound 5-2a relative to Compound 5-1.

In some embodiments, the reacting of Compound 5-2a with Compound 5-1 is conducted in the presence of potassium 2-methylpropan-2-olate in a solvent comprising THF.

In some embodiments, the Compound 5-2a is Compound 5-2:

(Compound 5-2)

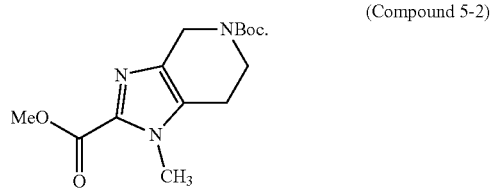 [SMILES: COC(=O)c1nc2c(n1C)CCN(C(=O)OC(C)(C)C)C2]

In some embodiments, Compound 5-1 is prepared by a process comprising:
reacting Compound 6-1a:

(Compound 6-1a)

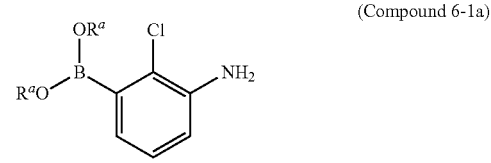

with Compound 2-3:

(Compound 2-3)

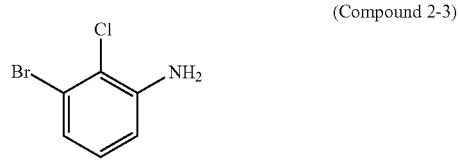

in the presence of a Suzuki catalyst and a base in a solvent to form said Compound 5-1, wherein:
each $R^a$ is independently selected from H and $C_{1-6}$ alkyl; or
each $R^a$, together with the oxygen atoms to which they are attached and the boron atom to which the oxygen atoms are attached, form a ring of formula

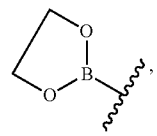

which is optionally substituted with 1, 2, 3, or 4 $C_{1-4}$ alkyl groups.

As used herein, the term "alkyl" refers to a saturated hydrocarbon group that may be straight-chain or branched. In some embodiments, the alkyl group contains 1 to 6 carbon atoms. Examples of alkyl moieties include, but are not limited to, chemical groups such as methyl, ethyl, n-propyl, isopropyl, n-butyl, tert-butyl, isobutyl, sec-butyl. In some embodiments, the alkyl moiety is methyl.

The Suzuki coupling reaction can be initiated using a number of palladium(O) and palladium(II) catalysts and performed under conditions known in the art (see, e.g., Miyaura and Suzuki, *Chem. Rev.* 1995, 95, 2457-2483, which is hereby incorporated in its entirety). In some embodiments, the palladium catalyst is $Pd(PPh_3)_4$ or $Pd(dppf)_2C_{1-2}$. In some embodiments, the catalyst is dichlorobis[di-tert-butyl(p-dimethylaminophenyl)phosphino]palladium.

In some embodiments, the reacting of Compound 6-1a and Compound 2-3 are carried out in the presence of dichlorobis[di-tert-butyl(p-dimethylaminophenyl)phosphino]palladium and potassium acetate in a solvent comprising dioxane and water.

In some embodiments, said Compound 6-1a is Compound 6-1:

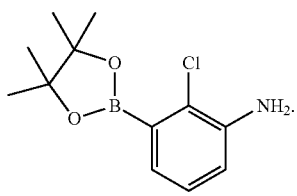
(Compound 6-1)

A compound of formula 5-4 can be prepared according to Scheme 7. Compound 1-5 can be converted to the acetal 7-1 under standard conditions [e.g., in the presence of trimethyl orthoformate and an acid, such as, p-toluenesulfonic acid]. Ester 7-1 can be hydrolyzed under alkaline conditions to provide acid 7-2. Then, the acetal of 7-2 can be deprotected under acidic conditions to produce the aldehyde 5-4.

In some embodiments, the present disclosure provides a compound selected from Compound 5-3a, Compound 5-3, Compound 5-4, and Compound 5-1:

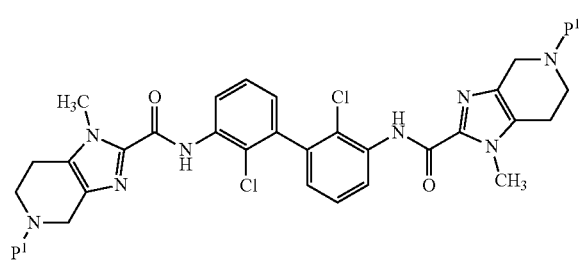
(Compound 5-3a)

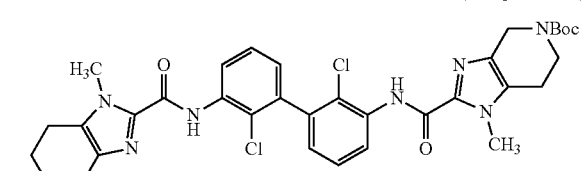
(Compound 5-3)

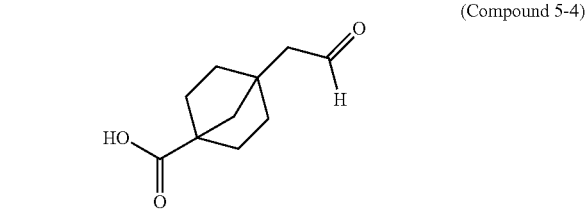
(Compound 5-4)

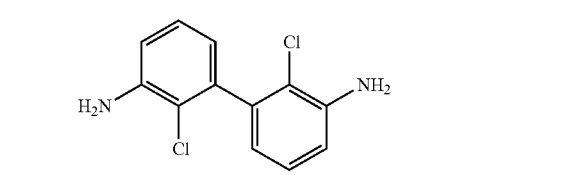
(Compound 5-1)

or a salt thereof.

Crystalline Free Base

In some embodiments, the crystalline free base of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) (Compound 1) is prepared by the process depicted in Scheme 5.

In some embodiments, Compound 1 crystalline free base can be characterized by the X-ray powder diffraction (XRPD) pattern substantially as shown in FIG. 1.

In some embodiments, Compound 1 crystalline free base has at least one X-ray powder diffraction (XRPD) peak, in terms of 2-theta (±0.2 degrees), selected from 6.2, 10.9, 11.3, 12.4, 13.7, 14.5, 15.5, 17.5, and 18.8 degrees. In some embodiments, Compound 1 crystalline free base has at least two X-ray powder diffraction (XRPD) peaks, in terms of 2-theta (±0.2 degrees), selected from 6.2, 10.9, 11.3, 12.4, 13.7, 14.5, 15.5, 17.5, and 18.8 degrees. In some embodiments, Compound 1 crystalline free base has at least three X-ray powder diffraction (XRPD) peaks, in terms of 2-theta (±0.2 degrees), selected from 6.2, 10.9, 11.3, 12.4, 13.7, 14.5, 15.5, 17.5, and 18.8 degrees. In some embodiments, Compound 1 crystalline free base has at least four X-ray powder diffraction (XRPD) peaks, in terms of 2-theta (±0.2 degrees), selected from 6.2, 10.9, 11.3, 12.4, 13.7, 14.5, 15.5, 17.5, and 18.8 degrees. In some embodiments, Compound 1 crystalline free base has characteristic X-ray powder diffraction (XRPD) peaks, in terms of 2-theta (±0.2 degrees), at 6.2, 10.9, 11.3, 12.4, 13.7, 14.5, 15.5, 17.5, and 18.8 degrees.

Figure 2:
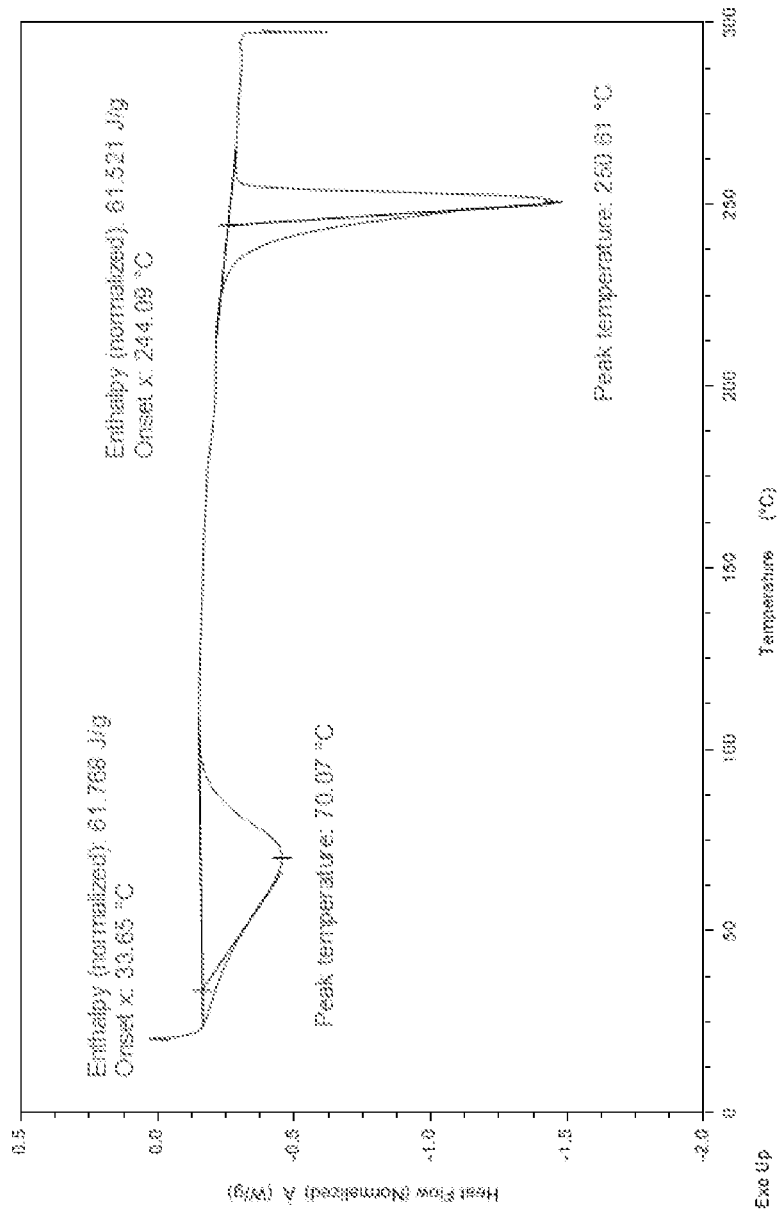
FIG. 2 shows a DSC thermogram of Compound 1 crystalline free base.
Figure 3:
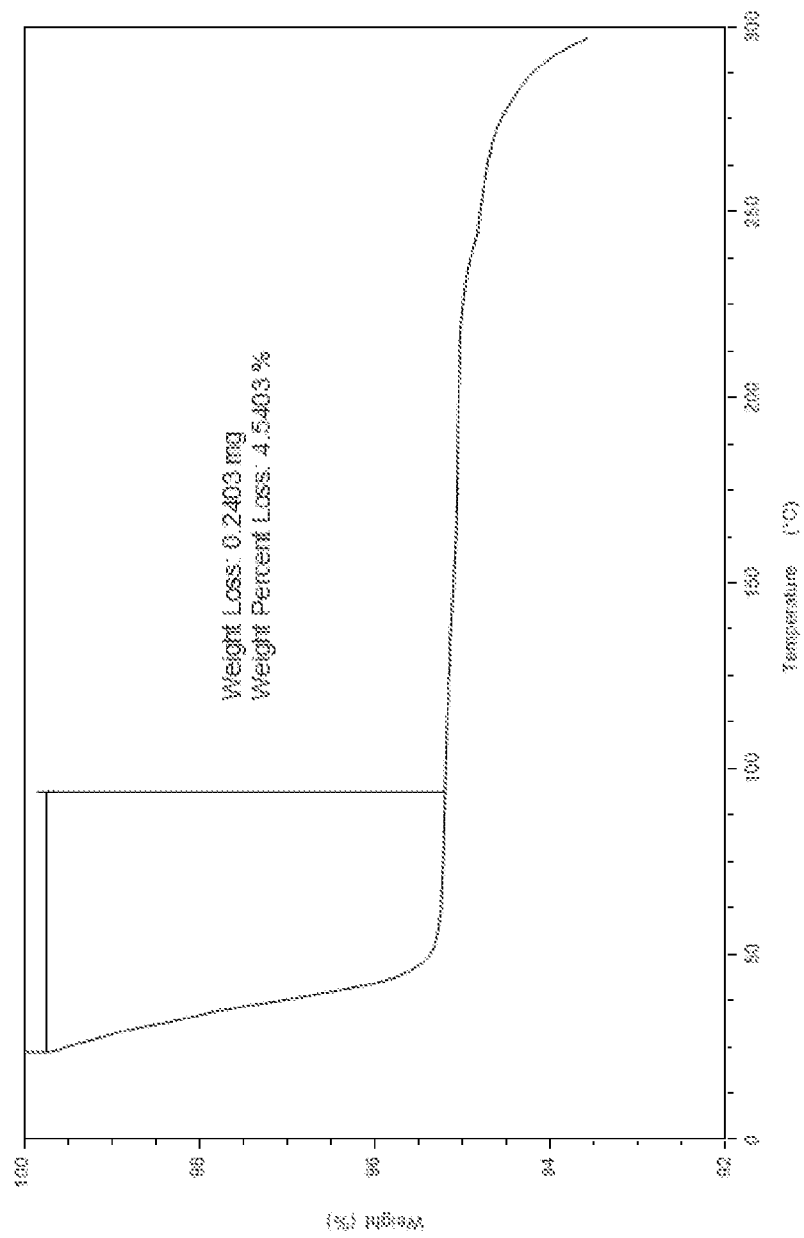
FIG. 3 shows a TGA thermogram of Compound 1 crystalline free base.

In some embodiments, Compound 1 crystalline free base exhibits a DSC thermogram having a first endothermic peak with an onset temperature of 33±3° C. and a maximum at 70±3° C. and a second endothermic peak with an onset temperature of 244±3° C. and a maximum at 250±3° C. In some embodiments, Compound 1 crystalline free base has a DSC thermogram substantially as depicted in FIG. 2. In some embodiments, Compound 1 crystalline free base has a TGA thermogram substantially as depicted in FIG. 3.

Methods of Use

Solid forms and salt forms described of the present disclosure can inhibit the activity of PD-1/PD-L1 protein/protein interaction and, thus, are useful in treating diseases and disorders associated with activity of PD-1 and the diseases and disorders associated with PD-L1 including its interaction with other proteins such as PD-1 and B7-1 (CD80). In certain embodiments, the solid forms and salt forms described of the present disclosure are useful for therapeutic administration to enhance, stimulate and/or increase immunity in cancer, chronic infection or sepsis, including enhancement of response to vaccination. In some embodiments, the present disclosure provides a method for inhibiting the PD-1/PD-L1 protein/protein interaction. The method includes administering to an individual or a patient a solid form, salt form or crystalline form thereof of Compound 1. The solid forms and salt forms described of the present disclosure can be used alone, in combination with other agents or therapies or as an adjuvant or neoadjuvant for the treatment of diseases or disorders, including cancer or infection diseases. For the uses described herein, any of the solid forms and salt forms described of the disclosure, including any of the embodiments or claims thereof, may be used.

The solid forms and salt forms described of the present disclosure inhibit the PD-1/PD-L1 protein/protein interaction, resulting in a PD-1 pathway blockade. The blockade of PD-1 can enhance the immune response to cancerous cells and infectious diseases in mammals, including humans. In some embodiments, the present disclosure provides treatment of an individual or a patient in vivo using a solid form, salt form or crystalline form thereof of Compound 1 such that growth of cancerous tumors is inhibited. A solid form, salt form or crystalline form thereof of Compound 1, can be used to inhibit the growth of cancerous tumors. Alternatively, a solid form, salt form or crystalline form thereof of Compound 1, can be used in conjunction with other agents or standard cancer treatments, as described below. In one embodiment, the present disclosure provides a method for inhibiting growth of tumor cells in vitro. The method includes contacting the tumor cells in vitro with a solid form, salt form or crystalline form thereof of Compound 1. In another embodiment, the present disclosure provides a method for inhibiting growth of tumor cells in an individual or a patient. The method includes administering to the individual or patient in need thereof a therapeutically effective amount of a solid form, salt form or crystalline form thereof of Compound 1.

In some embodiments, provided herein is a method for treating cancer. The method includes administering to a patient in need thereof, a therapeutically effective amount of a solid form, salt form or crystalline form thereof of Compound 1. Examples of cancers include those whose growth may be inhibited using salts of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a solid form, salt form or crystalline form thereof of Compound 1.

Examples of cancers that are treatable using the solid forms and salt forms described of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The solid forms and salt forms described of the present disclosure are also useful for the treatment of metastatic cancers, especially metastatic cancers that express PD-L1.

In some embodiments, cancers treatable with solid forms and salt forms described of the present disclosure include melanoma (e.g., metastatic malignant melanoma, cutaneous melanoma), renal cancer (e.g., clear cell carcinoma), prostate cancer (e.g., hormone refractory prostate adenocarcinoma), breast cancer (e.g., breast invasive carcinoma), colon cancer, lung cancer (e.g, non-small cell lung cancer and small cell lung cancer), squamous cell head and neck cancer (e.g, squamous cell carcinoma of the head and neck), urothelial cancer (e.g., bladder cancer, nonmuscle invasive bladder cancer (NMIBC)) and cancers with high microsatellite instability ($MSI^{high}$). Additionally, the disclosure includes refractory or recurrent malignancies whose growth may be inhibited using the salts of the disclosure.

In some embodiments, cancers that are treatable using the solid forms and salt forms described of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the solid forms and salt forms described of the present disclosure include, but are not limited to, cholangiocarcinoma, bile duct cancer, biliary tract cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the solid forms and salt forms described of the present disclosure can be used to treat sickle cell disease and sickle cell anemia.

In some embodiments, diseases and indications that are treatable using the solid forms and salt forms described of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, hamartoma, and teratoma.

Exemplary lung cancers include non-small cell lung cancer (NSCLC) (e.g., squamous cell NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (carcinoma, squamous cell carcinoma, adenocarcinoma, leiomyosarcoma, lymphoma), stomach (carcinoma, lymphoma, leiomyosarcoma, adenocarcinoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer (e.g., colorectal adenocarcinoma).

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). In some embodiments, the cancer is a urological cancer (e.g., papillary kidney carcinoma, testicular germ cell cancer, chromophobe renal cell carcinoma, clear cell renal carcinoma, or prostate adenocarcinoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, serous adenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma (e.g., cutaneous squamous cell carcinoma), Kaposi's sarcoma, moles dysplastic nevi, lipoma, angioma, dermatofibroma, and keloids. In some embodiments, diseases and indications that are treatable using the salts of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

PD-1 pathway blockade with solid forms and salt forms described of the present disclosure can also be used for treating infections such as viral, bacteria, fungus and parasite infections. The present disclosure provides a method for treating infections such as viral infections. The method includes administering to a patient in need thereof, a therapeutically effective amount of a solid form, salt form or crystalline form thereof of Compound 1. Examples of viruses causing infections treatable by methods of the present disclosure include, but are not limited to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limited to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, tuberculosis and arboviral encephalitis virus.

The present disclosure provides a method for treating bacterial infections. The method includes administering to a patient in need thereof, a therapeutically effective amount of a solid form, salt form or crystalline form thereof of Compound 1. Non-limiting examples of pathogenic bacteria causing infections treatable by methods of the disclosure include *chlamydia, rickettsial* bacteria, mycobacteria, staphylococci, streptococci, pneumococci, meningococci and conococci, *klebsiella, proteus, serratia, pseudomonas, legionella, diphtheria, salmonella*, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a solid form, salt form or crystalline form thereof of Compound 1. Non-limiting examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

The present disclosure provides a method for treating parasite infections. The method includes administering to a patient in need thereof, a therapeutically effective amount of a solid form, salt form or crystalline form thereof of Compound 1. Non-limiting examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

The present disclosure provides a method for treating neurodegenerative diseases or disorders. The method includes administering to a patient in need thereof, a therapeutically effective amount of a solid form, salt form or crystalline form thereof of Compound 1. Non-limiting examples of neurodegenerative diseases or disorders include Alzheimer's disease, Parkinson's disease, Huntington's disease, prion disease, Motor neurone diseases, Spinocerebellar ataxia and Spinal muscular atrophy.

It is believed that solid forms and salt forms, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active solid form, salt form or crystalline form thereof that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the solid forms and salt forms are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Immune-Checkpoint Therapies

Solid forms and salt forms described of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD122, CD96, CD73, CD47, CSF1R, JAK, PI3K delta, PI3K gamma, TAM, arginase, HPK1, A2AR, B7-H3, B7-H4, BTLA, CTLA-4, LAG3, TIM3, TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137 (4-1BB). In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the solid forms and salt forms described herein provided herein can be used in combination with one or more agents selected from KIR inhibitors, TIGIT inhibitors, LAIR1 inhibitors, CD160 inhibitors, 2B4 inhibitors and TGF beta inhibitors.

In some embodiments, the solid forms and salt forms provided herein can be used in combination with one or more agonists of immune checkpoint molecules, e.g., OX40, CD27, GITR, and CD137 (also known as 4-1BB).

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, cemiplimab, spartalizumab, camrelizumab, cetrelimab, toripalimab, sintilimab, SHR-1210, PDR001, MGA012, PDR001, AB122, AMP-224, JTX-4014, BGB-108, BCD-100, BAT1306, LZM009, AK105, HLX10, or TSR-042. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), durvalumab (Imfinzi®), atezolizumab (Tecentriq®), Avelumab (Bavencio®), MSB0010718C, tislelizumab, FAZ053, KN035, CS1001, SHR-1316, CBT-502, A167, STI-A101, CK-301, BGB-A333, MSB-2311, HLX20, or LY3300054. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 bispecific antibody. In some embodiments, the anti-PD-1/PD-L1 bispecific antibody is MCLA-136.

In some embodiments, the inhibitor is MCLA-145.

In some embodiments, the inhibitor of an immune checkpoint molecule is an inhibitor of CTLA-4, e.g., an anti- CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of PD-1 and CTLA-4, e.g., an anti-PD-1/CTLA-4 bispecific antibody. In some embodiments, the anti-PD-1/CTLA-4 antibody is AK104.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab. In some embodiments, the inhibitor of CD73 is MEDI9447.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the agonist of an immune checkpoint molecule is an agonist of GITR, e.g., an anti-GITR antibody. In some embodiments, the agonist is TRX518, MK-4166, INCAGN1876, MK-1248, AMG228, BMS-986156, GWN323, MEDI1873, orMEDI6469.

In some embodiments, the agonist of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, BMS-986178, or 9B12. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The solid forms and salt forms of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the solid forms and salt forms of the disclosure can be used in combination with one or more metabolic enzyme inhibitors. In some embodiments, the metabolic enzyme inhibitor is an inhibitor of IDO 1, TDO, or arginase. Examples of IDO 1 inhibitors include epacadostat, NLG919, BMS-986205, PF-06840003, IOM2983, RG-70099 and LY338196.

As provided throughout, the additional compounds, inhibitors, agents, etc. can be combined with the present solid form, salt form or crystalline form thereof in a single or continuous dosage form, or they can be administered simultaneously or sequentially as separate dosage forms.

Cancer Therapies

Cancer cell growth and survival can be impacted by dysfunction in multiple biological pathways. Thus, it may be useful to combine inhibitors of different mechanisms, such as enzyme inhibitors, signal transduction inhibitors, inhibitors of chromatin dynamics or modulators of immune responses, to treat such conditions. Targeting more than one signaling pathway (or more than one biological molecule involved in a given signaling pathway) may reduce the likelihood of drug-resistance arising in a cell population, or reduce the toxicity of treatment.

The solid forms and salt forms of the present disclosure can be used in combination with one or more other therapies for the treatment of diseases, such as cancer or infections. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the solid forms and salt forms of the present disclosure can be combined with one or more inhibitors of the following kinases for the treatment of cancer: Akt1, Akt2, Akt3, BCL2, CDK, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the solid forms and salt forms of the present disclosure can be combined with one or more of the following inhibitors for the treatment of cancer or infections. Non-limiting examples of inhibitors that can be combined with the solid forms and salt forms of the present disclosure for treatment of cancer and infections include an FGFR inhibitor (FGFR1, FGFR2, FGFR3 or FGFR4, e.g., pemigatinib (INCY54828), INCB62079), an EGFR (also known as ErB-1 or HER-1) inhibitor (e.g., erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2, e.g., ruxolitinib, baricitinib or itacitinib (INCB39110)), an IDO inhibitor (e.g., epacadostat, NLG919, or BMS-986205, MK7162), anLSD1 inhibitor (e.g., INCB59872 and INCB60003), a TDO inhibitor, a PI3K-delta inhibitor (e.g., Parsaclisib (INCB50465) and INCB50797), a PI3K-gamma inhibitor such as PI3K-gamma selective inhibitor, a Pim inhibitor (e.g., INCB53914), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib, talazoparib, or niraparib), a CSF1R inhibitor, a TAM receptor tyrosine kinase (Tyro-3, Axl, and Mer), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), an arginase inhibitor (INCB001158), a PARP inhibitor (such as rucaparib or olaparib), sitravatinib, a B-Raf inhibitor-MEK inhibitor combination (such as encorafenib plus binimetinib, dabrafenib plus trametinib, or cobimetinib plus vemurafenib), and an adenosine receptor antagonist or combinations thereof.

In some embodiments, the solid forms and salt forms of the present disclosure can be combined with a TLR7 agonist (e.g., imiquimod).

The solid forms and salt forms of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, STING agonists, RIG-I agonists, oncolytic virotherapy and immunomodulating small molecules, including thalidomide or JAK1/2 inhibitor, PI3Kδ inhibitor and the like. The solid forms and salt forms can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab), 4-1BB (e.g., urelumab, utomilumab), antibodies to PD-1 and PD-L1, or antibodies to cytokines (IL-10, TGF-β, etc.). Examples of antibodies to PD-1 and/or PD-L1 that can be combined with salts of the present disclosure for the treatment of cancer or infections such as viral, bacteria, fungus and parasite infections include, but are not limited to nivolumab, pembrolizumab, atezolizumab, durvalumab, avelumab and SHR-1210.

The solid forms and salt forms of the present disclosure can further be used in combination with one or more anti-inflammatory agents, steroids, immunosuppressants or therapeutic antibodies.

The solid forms and salt forms, can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The solid forms and salt forms, can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the solid forms and salt forms of the present disclosure can be used in combination with tumor specific antigen such as heat shock proteins isolated from tumor tissue itself. In some embodiments, the solid forms and salt forms, can be combined with dendritic cells immunization to activate potent anti-tumor responses.

The solid forms and salt forms of the present disclosure can be used in combination with bispecific macrocyclic peptides that target Fc alpha or Fc gamma receptor-expressing effectors cells to tumor cells. The solid forms and salt forms of the present disclosure can also be combined with macrocyclic peptides that activate host immune responsiveness.

The solid forms and salt forms of the present disclosure can be used in combination with bone marrow transplant for the treatment of a variety of tumors of hematopoietic origin.

The solid forms and salt forms, can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa.*

Viruses causing infections treatable by methods of the present disclosure include, but are not limited to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, coronavirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia, rickettsial* bacteria, mycobacteria, staphylococci, streptococci, pneumococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum.*

Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

When more than one pharmaceutical agent is administered to a patient, they can be administered simultaneously, separately, sequentially, or in combination (e.g., for more than two agents).

Formulation, Dosage Forms and Administration

When employed as pharmaceuticals, the solid forms and salt forms of the present disclosure can be administered in the form of pharmaceutical compositions. Thus the present disclosure provides a composition comprising a solid form, salt form or crystalline form thereof of Compound 1, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which comprise, as the active ingredient, the solid form, salt form or crystalline form thereof of the present disclosure, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active salt, soft and hard gelatin capsules, suppositories, sterile injectable solutions and sterile packaged powders.

In preparing a formulation, the active solid form, salt form or crystalline form thereof can be milled to provide the appropriate particle size prior to combining with the other ingredients. If the active salt is substantially insoluble, it can be milled to a particle size of less than 200 mesh. If the active solid form, salt form or crystalline form thereof is substantially water soluble, the particle size can be adjusted by milling to provide a substantially uniform distribution in the formulation, e.g., about 40 mesh.

The solid forms and salt forms of the present disclosure may be milled using known milling procedures such as wet milling to obtain a particle size appropriate for tablet formation and for other formulation types. Finely divided (nanoparticulate) preparations of the solid forms and salt forms of the present disclosure can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one solid form, salt form or crystalline form thereof of Compound 1. In some embodiments, the silicified microcrystalline cellulose comprises about 98% microcrystalline cellulose and about 2% silicon dioxide w/w.

In some embodiments, the composition is a sustained release composition comprising at least one solid form, salt form or crystalline form thereof of Compound 1, and at least one pharmaceutically acceptable carrier or excipient. In some embodiments, the composition comprises at least one solid form, salt form or crystalline form thereof of Compound 1, and at least one component selected from microcrystalline cellulose, lactose monohydrate, hydroxypropyl methylcellulose and polyethylene oxide. In some embodiments, the composition comprises at least one solid form, salt form or crystalline form thereof of Compound 1, and microcrystalline cellulose, lactose monohydrate and hydroxypropyl methylcellulose. In some embodiments, the composition comprises at least one solid form, salt form or crystalline form thereof of Compound 1, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active solid form, salt form or crystalline form thereof may be effective over a wide dosage range and is generally administered in a therapeutically effective amount. It will be understood, however, that the amount of the solid form, salt form or crystalline form thereof actually administered will usually be determined by a physician, according to the relevant circumstances, including the condition to be treated, the chosen route of administration, the actual solid form, salt form or crystalline form thereof administered, the age, weight, and response of the individual patient, the severity of the patient's symptoms and the like.

The therapeutic dosage of a solid form, salt form or crystalline form thereof of the present invention can vary according to, e.g., the particular use for which the treatment is made, the manner of administration of the solid form, salt form or crystalline form thereof, the health and condition of the patient, and the judgment of the prescribing physician. The proportion or concentration of a solid form, salt form or crystalline form thereof of the invention in a pharmaceutical composition can vary depending upon a number of factors including dosage, chemical characteristics (e.g, hydrophobicity), and the route of administration. For example, the solid forms and salt forms of the present disclosure can be provided in an aqueous physiological buffer solution containing about 0.1 to about 10% w/v of the salt for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the solid form, salt form or crystalline form thereof selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a solid form, salt form or crystalline form thereof of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the solid form, salt form or crystalline form thereof and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the salt of the invention. The topical formulations can be suitably packaged in tubes of, e.g., 100 g which are optionally associated with instructions for the treatment of the select indication, e.g., psoriasis or other skin condition.

The amount of solid form, salt form or crystalline form thereof or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the preparations typically will be between 3 and 11, more preferably from 5 to 9 and most preferably from 7 to 8.

The therapeutic dosage of a solid form, salt form or crystalline form thereof of the present invention can vary according to, e.g., the particular use for which the treatment is made, the manner of administration of the solid form, salt form or crystalline form thereof, the health and condition of the patient, and the judgment of the prescribing physician. The proportion or concentration of a solid form, salt form or crystalline form thereof of the invention in a pharmaceutical composition can vary depending upon a number of factors including dosage, chemical characteristics (e.g, hydrophobicity), and the route of administration. For example, the solid forms and salt forms of the present disclosure can be provided in an aqueous physiological buffer solution containing about 0.1 to about 10% w/v of the salt for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the salt selected, formulation of the excipient, and its route of administration. Effective doses can be extrapolated from dose-response curves derived from in vitro or animal model test systems.

Labeled Compounds and Assay Methods

The solid forms and salt forms of the present disclosure can further be useful in investigations of biological processes in normal and abnormal tissues. Thus, another aspect of the present invention relates to labeled solid forms and salt forms of the present disclosure (radio-labeled, fluorescent-labeled, etc) that would be useful not only in imaging techniques but also in assays, both in vitro and in vivo, for localizing and quantitating PD-1 or PD-L1 protein in tissue samples, including human, and for identifying PD-L1 ligands by inhibition binding of a labeled compound. Accordingly, the present invention includes PD-1/PD-L1 binding assays that contain such labeled salts.

The present invention further includes isotopically-substituted solid forms and salt forms of the present disclosure. An "isotopically-substituted" solid form, salt form or crystalline form thereof is a solid form, salt form or crystalline form thereof of the invention where one or more atoms are replaced or substituted by an atom having the same atomic number but a different atomic mass or mass number, e.g., a different atomic mass or mass number from the atomic mass or mass number typically found in nature (i.e., naturally occurring). It is to be understood that a "radio-labeled" solid form, salt form or crystalline form thereof is a solid form, salt form or crystalline form thereof that has incorporated at least one isotope that is radioactive (e.g., radionuclide). Suitable radionuclides that may be incorporated in salts of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled salts will depend on the specific application of that radio-labeled solid form, salt form or crystalline form thereof. For example, for in vitro PD-L1 protein labeling and competition assays, solid form, salt form or crystalline form thereof that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

In some embodiments, the radionuclide is selected from the group consisting of $^3$H, $^{14}$C, $^{125}$I, $^{35}$S and $^{82}$Br. Synthetic methods for incorporating radio-isotopes into organic compounds and salts are known in the art.

Specifically, a labeled solid form, salt form or crystalline form thereof of the invention can be used in a screening assay to identify and/or evaluate compounds. For example, a newly synthesized or identified solid form, salt form or crystalline form thereof (i.e., test solid form, salt form or crystalline form thereof) which is labeled can be evaluated for its ability to bind a PD-L1 protein by monitoring its concentration variation when contacting with the PD-L1 protein, through tracking of the labeling. For example, a test solid form, salt form or crystalline form thereof (labeled) can be evaluated for its ability to reduce binding of another compound which is known to bind to a PD-L1 protein (i.e., standard compound). Accordingly, the ability of a test solid form, salt form or crystalline form thereof to compete with the standard compound for binding to the PD-L1 protein directly correlates to its binding affinity. Conversely, in some other screening assays, the standard compound is labeled and test solid form, salt form or crystalline form thereof are unlabeled. Accordingly, the concentration of the labeled standard compound is monitored in order to evaluate the competition between the standard compound and the test solid form, salt form or crystalline form thereof, and the relative binding affinity of the test solid form, salt form or crystalline form thereof is thus ascertained.

Kits

The present disclosure also includes pharmaceutical kits useful, e.g., in the treatment or prevention of diseases or disorders associated with the activity of PD-L1 including its interaction with other proteins such as PD-1 and B7-1 (CD80), such as cancer or infections, which include one or more containers containing a pharmaceutical composition comprising a therapeutically effective amount of a solid form, salt form or crystalline form thereof of Compound 1, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following abbreviations may be used herein: aq. (aqueous); br (broad); d (doublet); dd (doublet of doublets); DCM (dichloromethane); DMF (N,N-dirnethylformarnide); DMSO (dimethylsulfoxide); Et (ethyl); EtOAc (ethyl acetate); EtOH (ethanol); g (gram(s)); h (hour(s)); HPLC (high performance liquid chromatography); Hz (hertz); IPAc (isopropyl acetate); J (coupling constant); LCMS (liquid chromatography—mass spectrometry); m (multiplet); M (molar); MS (Mass spectrometry); Me (methyl); MeCN (acetonitrile); MeOH (methanol); mg (milligram(s)); MIBK (methyl isobutyl ketone); min. (minutes(s)); mL (milliliter(s)); mmol (millimole(s)); MTBE (tert-butyl methyl ether); nM (nanomolar); NMR (nuclear magnetic resonance spectroscopy); Ph (phenyl); r.t. (room temperature); s (singlet); t (triplet or tertiary); TBS (tert-butyldimethylsilyl); tert (tertiary); tt (triplet of triplets); TFA (trifluoroacetic acid); THF (tetrahydrofuran); µg (microgram(s)); µL (microliter(s)); µM (micromolar); wt % (weight percent).

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The solid forms and salt forms of the present disclosure of the Examples have been found to inhibit the activity of PD-1/PD-L1 protein/protein interaction according to at least one assay described herein.

EXAMPLES

Experimental Methods

In some examples below, X-Ray Powder Diffraction analysis was carried out on a Rigaku MiniFlex X-ray Powder Diffractometer (XRPD) instrument. The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

In some examples below, X-Ray Powder Diffraction analysis was carried out on a Rigaku MiniFlex 300/600 X-ray Powder Diffractometer (XRPD) instrument. The general experimental procedures for XRPD were: (1) X-ray radiation from copper at 1.54186 Å with $K_\alpha$ filter; (2) X-ray power at 40 KV, 15 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min.

In some examples below, X-Ray Powder Diffraction analysis was carried out on a Bruker D8 Advance ECO X-ray Powder Diffractometer (XRPD) instrument. The general experimental procedures for XRPD were: (1) X-ray radiation from copper at 1.5418 Å and LYNXEYE™ detector; (2) X-ray power at 40 kV, 25 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min.

Differential Scanning Calorimetry (DSC) was carried out on a TA Instruments Differential Scanning Calorimetry, Model Q200 with autosampler. The DSC instrument conditions were as follows: 20-300° C. at 10° C./min; Tzero aluminum sample pan and lid; and nitrogen gas flow at 50 mL/min. Some experiments were run on a TA Instruments Differential Scanning Calorimetry, Model DSC2500 with autosampler. The DSC instrument conditions were as follows: 20-300° C. at 10° C./min; Tzero aluminum sample pan and lid; and nitrogen gas flow at 50 mL/min.

Thermogravimetric analysis (TGA) was carried out on a TA Instruments Thermogravimetric Analyzer, Discovery TGA5500 with autosampler. The general experimental conditions for TGA were: ramp from 25° C.-300° C. at 10° C./min; nitrogen purge, gas flow at 25 mL/min; platinum sample holder. Some experiments were run on a TA Instruments Thermogravimetric Analyzer, TGA Q500 with autosampler. The general experimental conditions for TGA were: ramp from 25° C.-600° C. at 20° C./min; nitrogen purge, gas flow at 25 mL/min; platinum sample pan.

Purity was determined by HPLC using the conditions shown below.

| Instrument | Agilent 1100 |
|---|---|
| Column | Zorbax SB-C18, 3.5 µm, 4.6 × 150 mm |
| Column Temperature | 40° C. |
| Mobile Phase A | 0.05% TFA in water |
| Mobile Phase B | 0.05% TFA In acetonitrile |
| Flow Rate | 1 mL/min |
| Injection Volume | 5 µL |
| Total Run Time | 24 min |
| UV Detector Wavelength | 254 nm |

| Gradient Table: | | |
|---|---|---|
| Time (min) | Mobile Phase A | Mobile Phase B |
| 0 | 95 | 5 |
| 15 | 5 | 95 |
| 18 | 5 | 95 |
| 18.5 | 95 | 5 |
| 24 | 95 | 5 |

Qualitative NMR analysis ($^1$H) was conducted on Bruker BioSpin GmbH 400 NMR spectrometer. The NMR sample was prepared by dissolving about 6-7 mg of Compound 1 Di-HCl salt in 0.6-0.7 of DMSO-$d_6$ and transferred to NMR tube. Quantitative $^1$H NMR data were collected using a 30-degree proton pulse sequence with a delay time of 1.0 second, pulse width of 15, at 300 Fahrenheit. 16 scans were taken for each experiment.

Example A1. Preparation of 4-(2-oxoethyl)bicyclo[2.2.1]heptane-1-carboxylic acid

Step 1: methyl 4-(2,2-dimethoxyethyl)bicyclo[2.2.1]heptane-1-carboxylate

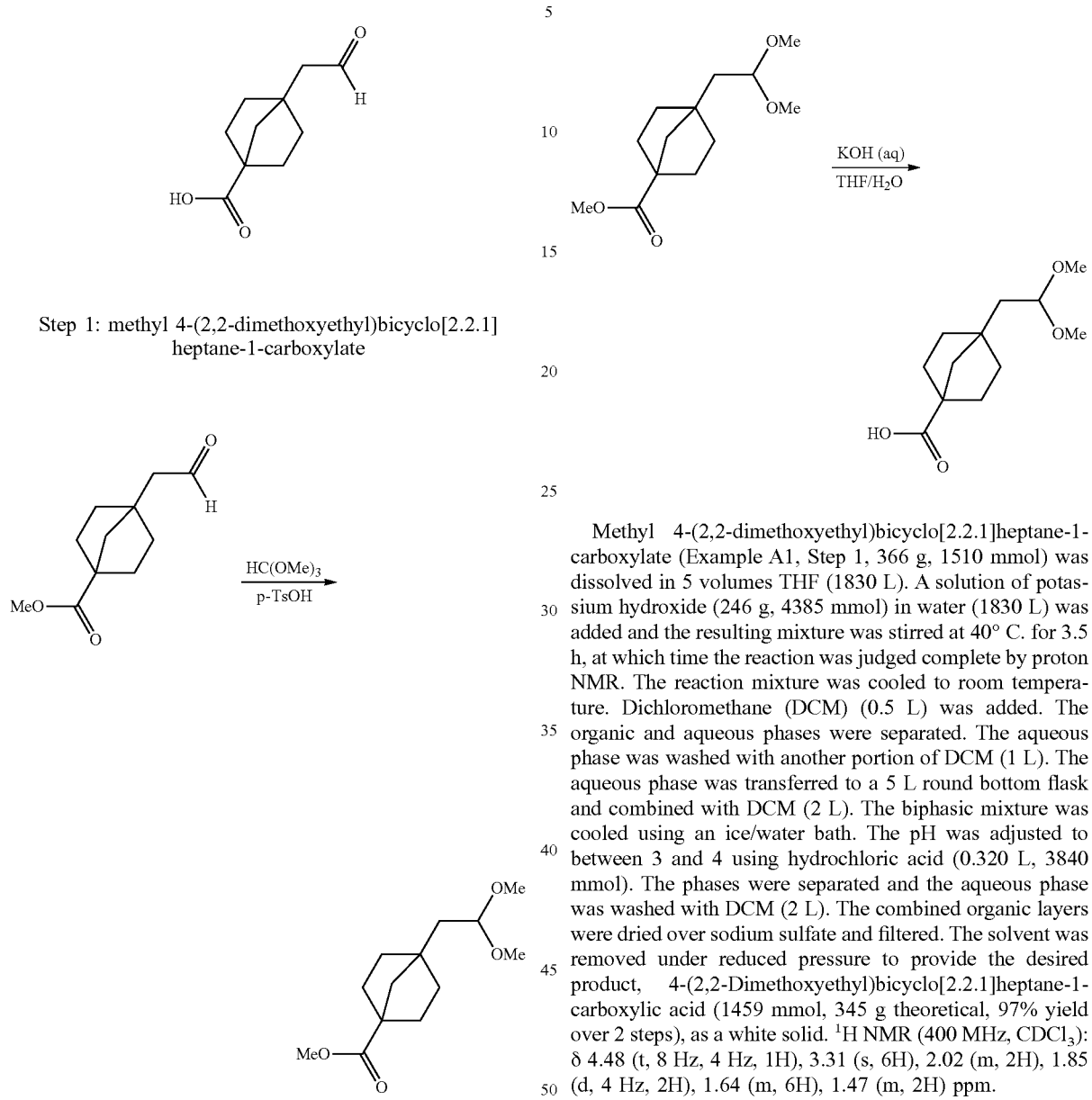

Methyl 4-(2-oxoethyl)bicyclo[2.2.1]heptane-1-carboxylate (296.49 g, 1511 mmol) and trimethyl orthoformate (334 ml, 3022 mmol) were combined in a 2 L round bottom flask, p-Toluenesulfonic acid monohydrate (1.150 g, 6.04 mmol) was added to the reaction mixture (exotherm). The reaction mixture was heated at 50° C. for 2 h, at which time the reaction was judged complete by proton NMR. The reaction mixture was cooled to room temperature and the solvent was removed under reduced pressure. The resulting viscous liquid, which is the crude desired product, was used as is for the next ester saponification reaction. NMR (400 MHz, CDCl$_3$): δ 4.45 (t, 8 Hz, 1H), 3.67 (s, 3H), 3.30 (s, 6H), 1.97 (m, 2H), 1.83 (d, 4 Hz, 2H), 1.63 (m, 6H), 1.45 (m, 2H) ppm.

Step 2; 4-(2,2-Dimethoxyethyl)bicyclo[2.2.1]heptane-1-carboxylic acid

Methyl 4-(2,2-dimethoxyethyl)bicyclo[2.2.1]heptane-1-carboxylate (Example A1, Step 1, 366 g, 1510 mmol) was dissolved in 5 volumes THF (1830 L). A solution of potassium hydroxide (246 g, 4385 mmol) in water (1830 L) was added and the resulting mixture was stirred at 40° C. for 3.5 h, at which time the reaction was judged complete by proton NMR. The reaction mixture was cooled to room temperature. Dichloromethane (DCM) (0.5 L) was added. The organic and aqueous phases were separated. The aqueous phase was washed with another portion of DCM (1 L). The aqueous phase was transferred to a 5 L round bottom flask and combined with DCM (2 L). The biphasic mixture was cooled using an ice/water bath. The pH was adjusted to between 3 and 4 using hydrochloric acid (0.320 L, 3840 mmol). The phases were separated and the aqueous phase was washed with DCM (2 L). The combined organic layers were dried over sodium sulfate and filtered. The solvent was removed under reduced pressure to provide the desired product, 4-(2,2-Dimethoxyethyl)bicyclo[2.2.1]heptane-1-carboxylic acid (1459 mmol, 345 g theoretical, 97% yield over 2 steps), as a white solid. $^1$H NMR (400 MHz, CDCl$_3$): δ 4.48 (t, 8 Hz, 4 Hz, 1H), 3.31 (s, 6H), 2.02 (m, 2H), 1.85 (d, 4 Hz, 2H), 1.64 (m, 6H), 1.47 (m, 2H) ppm.

Step 3; 4-(2-Oxoethyl)bicyclo[2.2.1]heptane-1-carboxylic acid

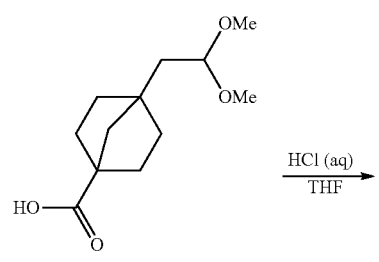

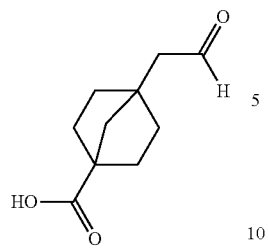

4-(2,2-Dimethoxyethyl)bicyclo[2.2.1]heptane-1-carboxylic acid (Example A1, Step 2, 194 g, 850 mmol) was charged to a 5 L round bottom flask and dissolved in four volumes THF (800 ml). 2.0 N hydrochloric acid (2500 ml, 5000 mmol) was added and the mixture was stirred at room temperature for 1.5 h at which time the reaction was judged complete by proton NMR. The reaction mixture was cooled in an ice-water bath. Sodium bicarbonate (527 g, 6272 mmol) was added (portionwise to avoid overflow) to adjust the pH to between 7-8. Another portion of water (500 mL) was added. The organic and aqueous phases were extracted. The aqueous phase was washed with additional DCM (800 mL). The aqueous phase was transferred to a 5 L round bottom flask and hydrochloric acid (123 ml, 1476 mmol) was used to adjust the pH to between 3 and 4. The aqueous phase was then extracted three times with DCM (1 L). The combined organic layers were dried with sodium sulfate and filtered. The solvent was removed under reduced pressure to provide the desired product, 4-(2-oxoethyl)bicyclo[2.2.1]heptane-1-carboxylic acid (145.8 g, 800 mmol, 155 g theoretical, 94% yield), as a white solid. MS calculated for $C_{10}H_{14}O_3$ $M^+$: m/z=182.0; found $(M-H_2O)^+$: m/z=164.1; $^1H$ NMR (400 MHz, $CDCl_3$): δ 9.78 (s, 1H), 2.61 (d, 4 Hz, 2H), 2.04 (m, 2H), 1.63 (m, 8H).

Example 1a. Preparation of the Compound 1 Crystalline Free Base (Method 1)

Step 1: 2,2'-dichloro-[1,1'-biphenyl]-3,3'-diamine

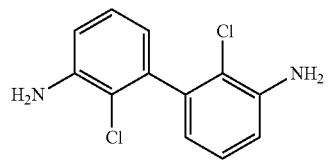

3-Bromo-2-chloroaniline (1020 g, 4841 mmol), 4,4,4',4',5,5,5',5'-octamethyl-2,2'-bi(1,3,2-dioxaborolane) (676 g, 2663 mmol), potassium acetate (1901 g, 1.94E+04 mmol) and Pd-132 (bis(di-tert-butyl(4-dimethylaminophenyl)phosphine)dichloropalladium(II)) (10.28 g, 14.52 mmol) were charged into a 22 L reactor. Dioxane (4500 ml) and water (1500 ml) were added and the reaction mixture was purged with nitrogen to remove oxygen from the reaction mixture. The reaction mixture was stirred and heated to 86-88° C. The reaction mixture was stirred for 3.5 h at which time HPLC showed the reaction was incomplete. Additional 4,4,4',4',5,5,5',5'-octamethyl-2,2'-bi(1,3,2-dioxaborolane) (62 g, 244 mmol) was charged. After another 1.5 h, the reaction was judged complete by HPLC. The reaction mixture was cooled to <50° C. and water (7500 mL) was added. The mixture was agitated overnight at ambient temperature. The resultant solid was filtered and washed with water (4 portions of 2000 mL). The solid was dried on the funnel. The crude solid obtained was dissolved in a mixture of MeOH (600 mL) and dichloromethane (DCM, 12 L). Then it was agitated with activated charcoal (100 g) and silica gel (630 g) for 1 h. The mixture was filtered through a pad of celite and washed with a mixture of methanol (MeOH) in DCM (5% volume ratio, 6 L total). The filtrate was concentrated to remove most of the DCM and MeOH (~90% of the solvents) and MTBE (4000 mL) was charged. The mixture was further concentrated to remove additional solvent. Another portion of methyl t-butyl ether (MTBE) (2000 mL) was charged and the solution was concentrated to adjust the volume of MTBE

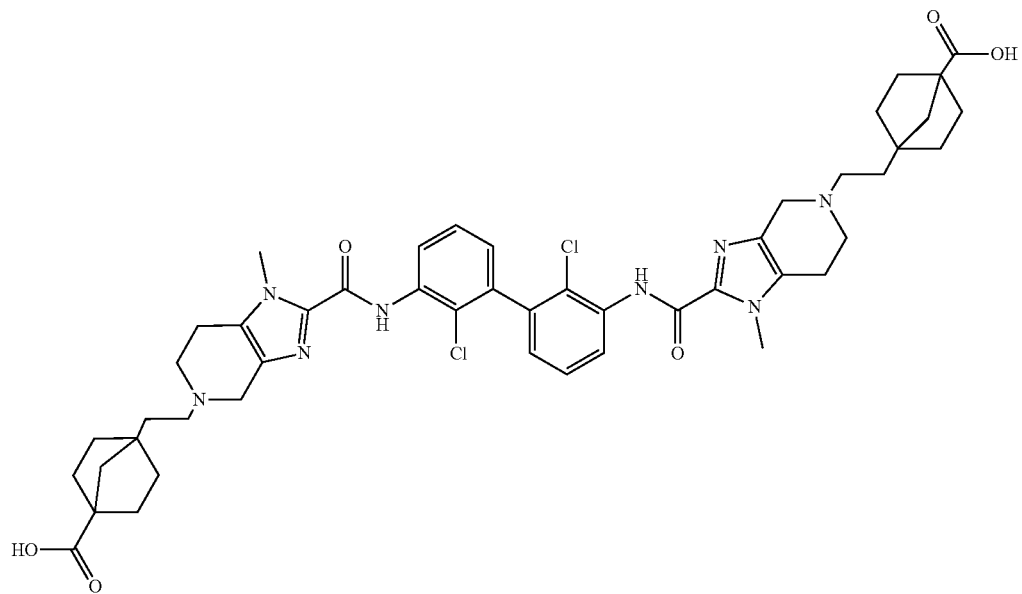 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCC13CCC(C(=O)O)(CC1)C3)C2]

to ~1000-1500 mL by weight. n-Heptane (1600 mL) was charged and the solution was agitated at 50° C. (water bath temperature) on the rotavap for 1 h. The mixture was cooled with agitation overnight. The solid was filtered and washed with a mixture of MTBE and n-heptane (300 mL MTBE+700 mL n-heptane). The solid was dried on the filter to provide the desired product as a yellow solid (1079 g, 88% yield). LCMS calculated for $C_{12}H_{11}Cl_2N_2$ $(M+H)^+$: m/z=253.02; found 253.1; $^1H$ NMR (400 MHz, DMSO-$d_6$): δ 7.04 (dd, 2H), 6.80 (dd, 2H), 6.40 (dd, 2H), 5.37 (s, 4H) ppm.

Step 2; di-tert-butyl 2,2'-(((2,2'-dichloro-[1,1'-biphenyl]-3,3 diyl)bis(azanediyl))bis(carbonyl))bis(1-methyl-1,4,6,7-tetrahydro-5H-imidazo[4,5-c]pyridine-5-carboxylate)

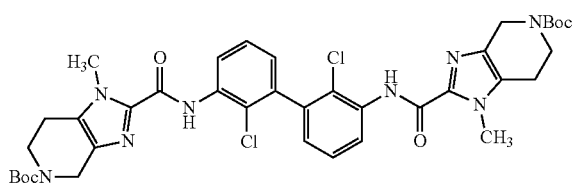 [SMILES: Cn1c(C(=O)Nc2cccc(-c3cccc(NC(=O)c4nc5c(n4C)CCN(C(=O)OC(C)(C)C)C5)c3Cl)c2Cl)nc2c1CCN(C(=O)OC(C)(C)C)C2]

2,2'-Dichloro-[1,1'-biphenyl]-3,3'-diamine (490 g, 1587 mmol) and 5-(tert-butyl) 2-methyl 1-methyl-1,4,6,7-tetrahydro-5H-imidazo[4,5-c]pyridine-2,5-dicarboxylate (1125 g, 3810 mmol) were charged to a 22 L reactor and dissolved in tetrahydrofuran (THF) (2000 ml). The mixture was stirred vigorously and potassium 2-methylpropan-2-olate (3810 ml, 3810 mmol) (1.0 M solution in THF) was charged. The mixture was agitated at ambient temperature for 1.5 h, at which time HPLC showed the reaction was complete. Water (12.00 L) was charged to quench the reaction and precipitate the product. A minor exotherm was observed, with an increase in the reaction mixture temperature from 25° C. to 30° C. The solution was cooled to 25° C. and then the resulting solid was isolated by filtration. The solid was washed with water and n-heptane to afford the desired product as a white solid (1185 g, 96% yield, 99.3% purity by HPLC area (220 nm, pH 2). LCMS calculated for $C_{38}H_{44}Cl_2N_8O_6$ $M^+$: m/z=778.28; found $[(M+2H)/2]^+$: m/z=390.2; $^1H$ NMR (400 MHz, DMSO-$d_6$): δ 9.89 (s, 2H), 8.52 (m, 2H), 7.39 (t, 2H), 7.06 (dd, 2H), 4.52 (s, 4H), 4.0 (s, 6H), 3.81 (s, 4H), 2.71 (t, 4H), 1.29 (s, 18H) ppm.

Step 3; N, N'-(2,2'-dichloro-[1,1'-biphenyl]-3,3'-diyl)bis(1-methyl-4,5,6,7-tetrahydro-1H-imidazo[4,5-c]pyridine-2-carboxamide) dihydrochloride

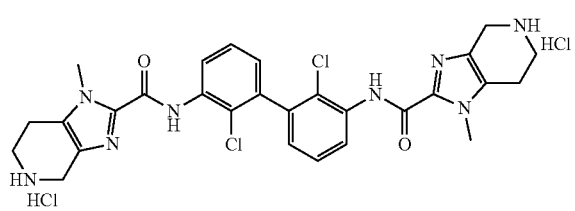 [SMILES: Cn1c(C(=O)Nc2cccc(-c3cccc(NC(=O)c4nc5c(n4C)CCNC5)c3Cl)c2Cl)nc2c1CCNC2 ; Cl ; Cl]

To a 22 L reactor was added di-tert-butyl 2,2'-(((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-5-carboxylate) (1165 g, 1494 mmol) and MeOH (11000 ml). The mixture was agitated thoroughly and hydrogen chloride (1245 ml, 1.49E+04 mmol) (concentrated aqueous solution, 12 N) was charged. The reaction temperature increased from 21° C. to 33° C. The reaction mixture was stirred at 50-52° C. for 1.5 h, at which time the reaction was judged complete by HPLC. The mixture was cooled to below 25° C. The solid was filtered and washed with MeOH, then Acetonitrile, then MTBE and dried to provide the desired product as the dihydrochloride salt (986 g, 1494 mmol, 101% yield). The product was used as is in the next step.

Step 4; N,N'-(2,2'-dichloro-[1,1'-biphenyl]-3,3'-diyl) bis(1-methyl-4,5,6,7-tetrahydro-1H-imidazo[4,5-c] pyridine-2-carboxamide)

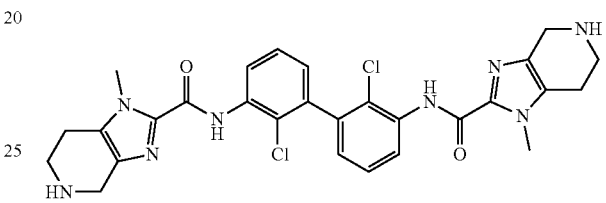

N,N'-(2,2'-Dichloro-[1,1'-biphenyl]-3,3'-diyl)bis(1-methyl-4,5,6,7-tetrahydro-1H-imidazo[4,5-c]pyridine-2-carboxamide) dihydrochloride (326 g, 500 mmol) was charged to a 3 neck 5 L round bottomed flask. THF (1000 ml) was charged and the mixture was agitated. A solution of Sodium Bicarbonate (92 g, 1099 mmol) in water (1200 ml) was charged in one portion at ambient temperature. The mixture was stirred at ambient temperature for 3 h, at which time the pH was measured to be ~8. The solid was filtered and washed with water (3 portions of 500 mL) and n-heptane (3 portions of 600 mL). The solid was dried on the funnel and then transferred to a vacuum oven with a nitrogen sweep at 45° C. This afforded N,N'-(2,2'-dichloro-[1,1'-biphenyl]-3,3'-diyl)bis(1-methyl-4,5,6,7-tetrahydro-1H-imidazo[4,5-c]pyridine-2-carboxamide) (296.7 g, 99.4% purity by HPLC area (220 nm, pH 2), 96% yield). LCMS calculated for $C_{28}H_{29}Cl_2N_8O_2$ $(M+H)^+$: m/z=579.17; found 579.2; $^1H$ NMR (400 MHz, DMSO-$d_6$) δ 9.93 (s, 2H), 9.32 (m, 2H), 8.30 (ddd, 2H), 7.52 (t, 2H), 7.19 (dd, 2H), 4.22 (s, 4H), 3.96 (s, 6H), 3.50 (m, 4H), 2.96 (m, 4H) ppm.

Step 5; 4,4'-(((((2,2'-dichloro-[1,1'-biphenyl]-3,3'-diyl)bis(azanediyl))bis (carbonyl))bis(1-methyl-1,4, 6,7-tetrahydro-5H-imidazo[4,5-c]pyridine-2,5-diyl)) bis(ethane-2,1-diyl))bis(bicyclo[2.2.1]heptane-1-carboxylic acid) (Compound 1)

In a 1 L round bottomed flask, N,N'-(2,2'-dichloro-[1,1'-biphenyl]-3,3'-diyl)bis(1-methyl-4,5,6,7-tetrahydro-1H-imidazo[4,5-c]pyridine-2-carboxamide) (Example 1a, Step 4, 7.4 g, 12.77 mmol) was slurried in DCM (150 ml). Then, 4-(2-oxoethyl)bicyclo[2.2.1]heptane-1-carboxylic acid (Example A1, Step 3), 7.45 g, 40.9 mmol) was added. The mixture was stirred at rt for 3 h. After which time, sodium triacetoxyborohydride (8.12 g, 38.3 mmol) was added and the reaction mixture was stirred at rt for 1 h, until HPLC showed starting material was consumed. The reaction was quenched with sodium bicarbonate (3.22 g, 38.3 mmol) in 100 mL water. Thick solids formed. Acetonitrile (100 ml)

was added to aid stirring and provide a better solid form for filtration. The mixture was slurried for 30 min, filtered and washed with a DCM/acetonitrile (ACN)/water mixture. The solid was dried on the filter to provide Compound 1 crystalline free base.

The crystallinity of the crystalline free base was confirmed by XRPD (FIG. 1, Table 1) and further supported by DSC (FIG. 2), indicating the crystalline compound having a first endothermic peak with an onset temperature at 33.7° C. and a maximum at 70.1° C., and a second endothermic peak with an onset temperature at 244.1° C. and a maximum at 250.6° C. TGA of the crystalline free base is provided in FIG. 3, and exhibited approximately 4.5% of weight loss below 100° C.

TABLE 1

| XRPD Peak Data for the Compound 1 Crystalline Free Base | |
|---|---|
| 2-Theta (°) | Relative Intensity (%) |
| 6.2 | 100 |
| 8.7 | 4.1 |
| 10.5 | 6.0 |
| 10.9 | 21.0 |
| 11.3 | 15.6 |
| 12.4 | 14.5 |

TABLE 1-continued

| XRPD Peak Data for the Compound 1 Crystalline Free Base | |
|---|---|
| 2-Theta (°) | Relative Intensity (%) |
| 13.7 | 59.3 |
| 14.5 | 24.1 |
| 15.5 | 27.4 |
| 16.0 | 4.0 |
| 16.6 | 12.7 |
| 16.9 | 6.1 |
| 17.5 | 14.4 |
| 18.8 | 18.5 |
| 19.2 | 11.3 |
| 20.2 | 0.7 |
| 21.0 | 3.5 |
| 21.5 | 5.3 |
| 22.7 | 9.3 |
| 23.1 | 1.6 |
| 24.2 | 8.9 |
| 24.7 | 24.5 |
| 25.0 | 10.0 |
| 26.0 | 1.9 |
| 26.9 | 23.7 |
| 28.0 | 1.2 |
| 28.7 | 3.4 |

Example 1b. Preparation of the Compound 1 Crystalline Free Base (Method 2)

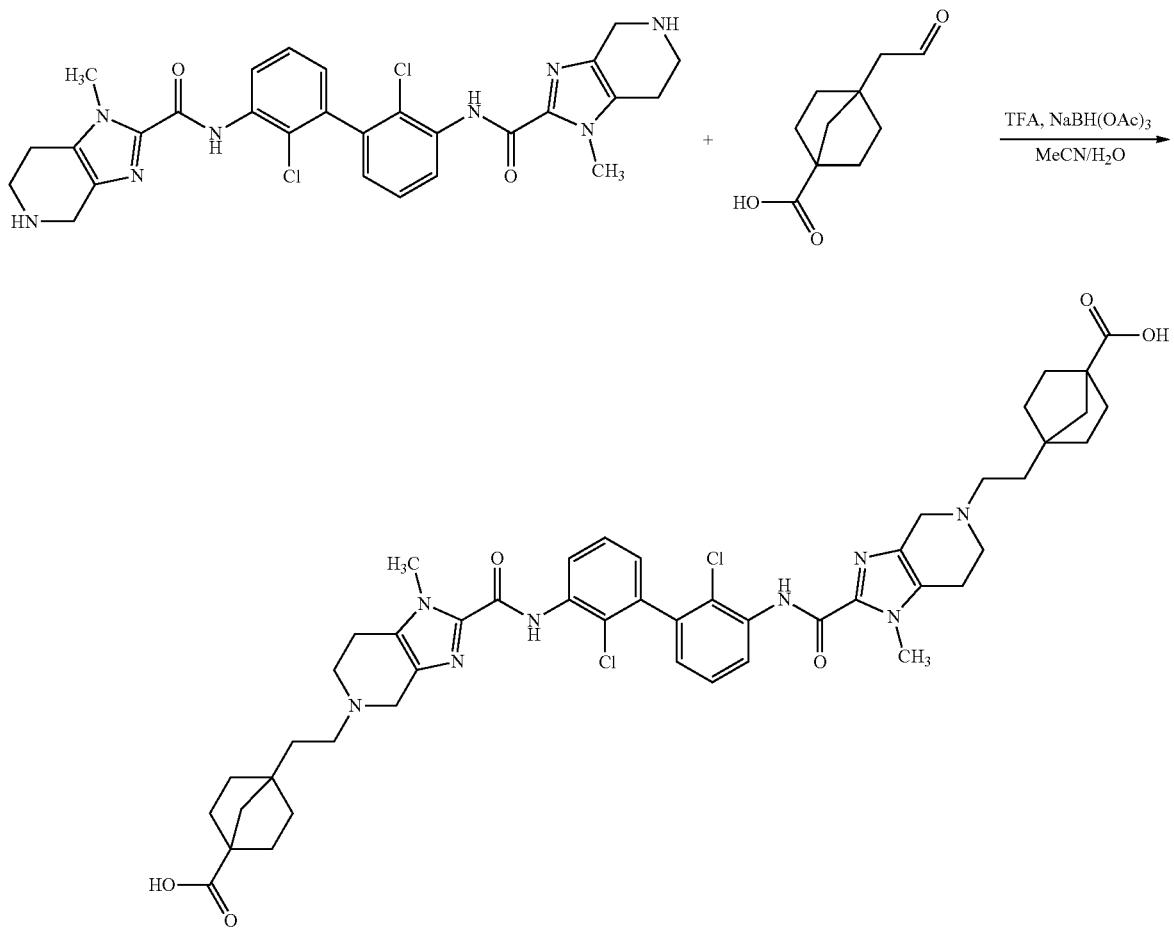 [SMILES: Cn1c(C(=O)Nc2cccc(-c3cccc(NC(=O)c4nc5c(n4C)CCNC5)c3Cl)c2Cl)nc2c1CCNC2 ; O=CCC12CCC(C(=O)O)(CC1)C2 ; Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCC13CCC(C(=O)O)(CC1)C3)C2]

Trifluoroacetic acid (TFA) (10.21 ml, 133 mmol) was added to a suspension of N,N'-(2,2'-dichloro-[1,1'-biphenyl]-3,3'-diyl)bis(1-methyl-4,5,6,7-tetrahydro-1H-imidazo[4,5-c]pyridine-2-carboxamide) (Example 1a, Step 4, 20.0 g, 33.1 mmol) and 4-(2-oxoethyl)bicyclo[2.2.1]heptane-1-carboxylic acid (Example A1, Step 3, 18.30 g, 99 mmol) in acetonitrile (268 ml) and water (53.6 ml) (16 V total). The solid dissolved in 10 min. Then sodium triacetoxyborohydride (21.07 g, 99 mmol) was added in two portions in 1 min. The reaction was stirred at room temp for 1 h. HPLC area percentage (220 nM, pH 2): 99.05%. The mixture was diluted with 240 mL CH₃CN (12 V), and quenched with sodium carbonate (12.99 g, 123 mmol) in 240 mL water (12 V) (after quenching pH was around 6). The solid was filtered and dried to give the desired product. HPLC area percentage (220 nM, pH 2): 99.01%. This solid contained TFA, determined by $^{19}$F NMR. The solid was reslurried with 0.20 equiv sodium carbonate (0.702 g, 6.63 mmol) in H₂O (240 mL)/ CH₃CN (240 mL) overnight, and then filtered. The solid was dried in vacuum oven to give the desired product, 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic Acid) (29.3 g), as white to off-white solids. HPLC area percentage (220 nM, pH 2): 99.12%; LCMS calculated for C₄₈H₅₇Cl₂N₈O₆ (M+H)⁺: m/z=911.4; found 911.3; ¹H NMR (400 MHz, DMSO-d₆) δ 11.94 (s, 2H), 9.90 (s, 2H), 8.38 (dd, 2H), 7.49 (t, 2H), 7.15 (dd, 2H), 3.91 (s, 6H), 3.42 (s, 4H), 2.76 (t, 4H), 2.67 (t, 4H), 2.57-2.53 (m, 4H), 1.92-1.82 (m, 4H), 1.73 (t, 4H), 1.57-1.47 (m, 8H), 1.44 (s, 4H), 1.42-1.34 (m, 4H) ppm.

Example 1c. Preparation of the Compound 1 Crystalline Free Base (Method 3)

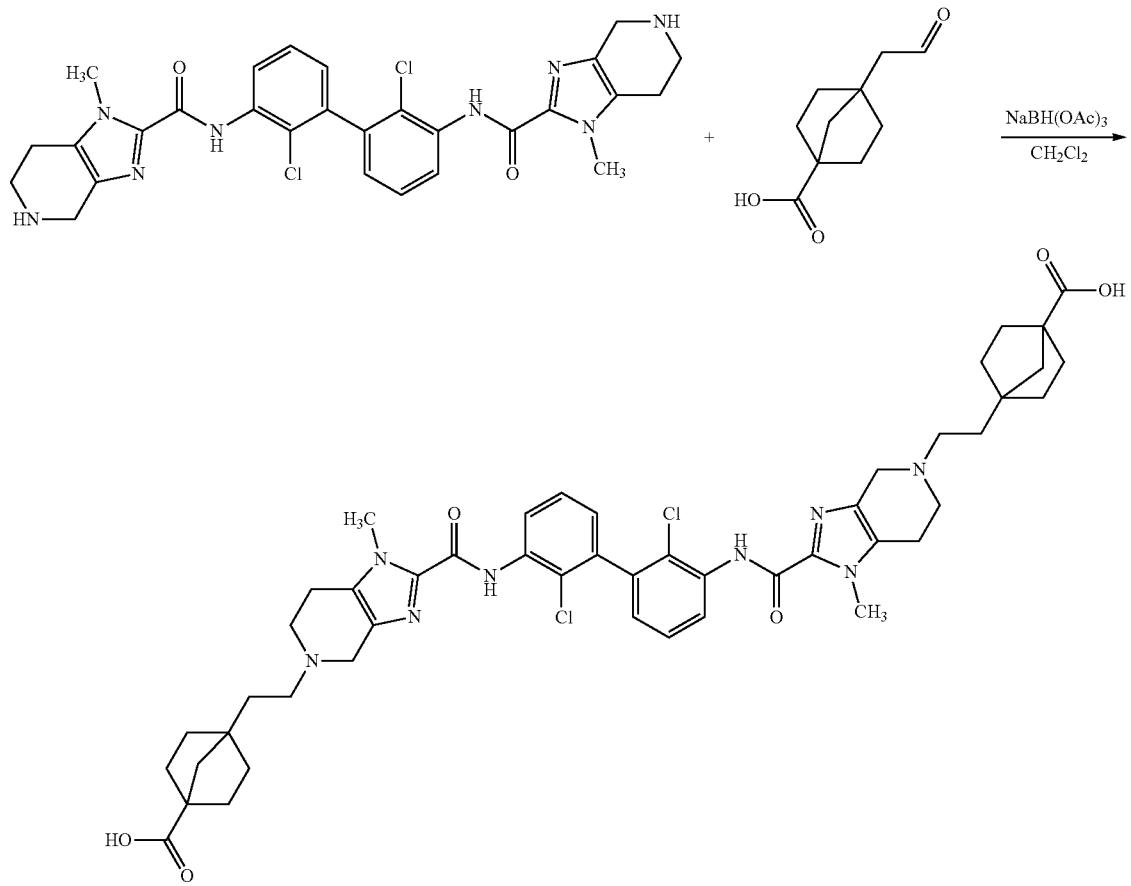

In a 2 L round bottle flask, N,N'-(2,2'-dichloro-[1,1'-biphenyl]-3,3'-diyl)bis(1-methyl-4,5,6,7-tetrahydro-1H-imidazo[4,5-c]pyridine-2-carboxamide) (Example 1a, Step 4, 20 g, 32.4 mmol) and 4-(2-oxoethyl)bicyclo[2.2.1]heptane-1-carboxylic acid (Example A1, Step 3, 17.91 g, 97 mmol) were slurried in anhydrous DCM (400 ml) and anhydrous isopropanol (100 mL) for 1.5 h, at which time all solids were dissolved. Sodium triacetoxyborohydride (22.0 g, 104 mmol) was added portionwise (a temperature increase to 30-35° C. was observed). The reaction mixture was stirred at room temperature for 2.5 h, until HPLC showed starting material was consumed. The reaction was quenched with sodium bicarbonate (10.22 g, 122 mmol) in water (250 mL). Thick solids formed. Acetonitrile (250 ml) was added to aid stirring and provide a better solid for filtration. The mixture was slurried for 30 min, filtered, and washed with a 1:1 acetone/water mixture followed by acetone. The solid was dried under a nitrogen sweep to provide the desired product, 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic Acid) (30.3 g, 100% yield, containing solvents; HPLC area percentage (220 nM, pH 2): 98.7%), as a white solid, and was used without further purification.

Example 1d. Preparation of the Compound 1 Crystalline Free Base (Method 4)
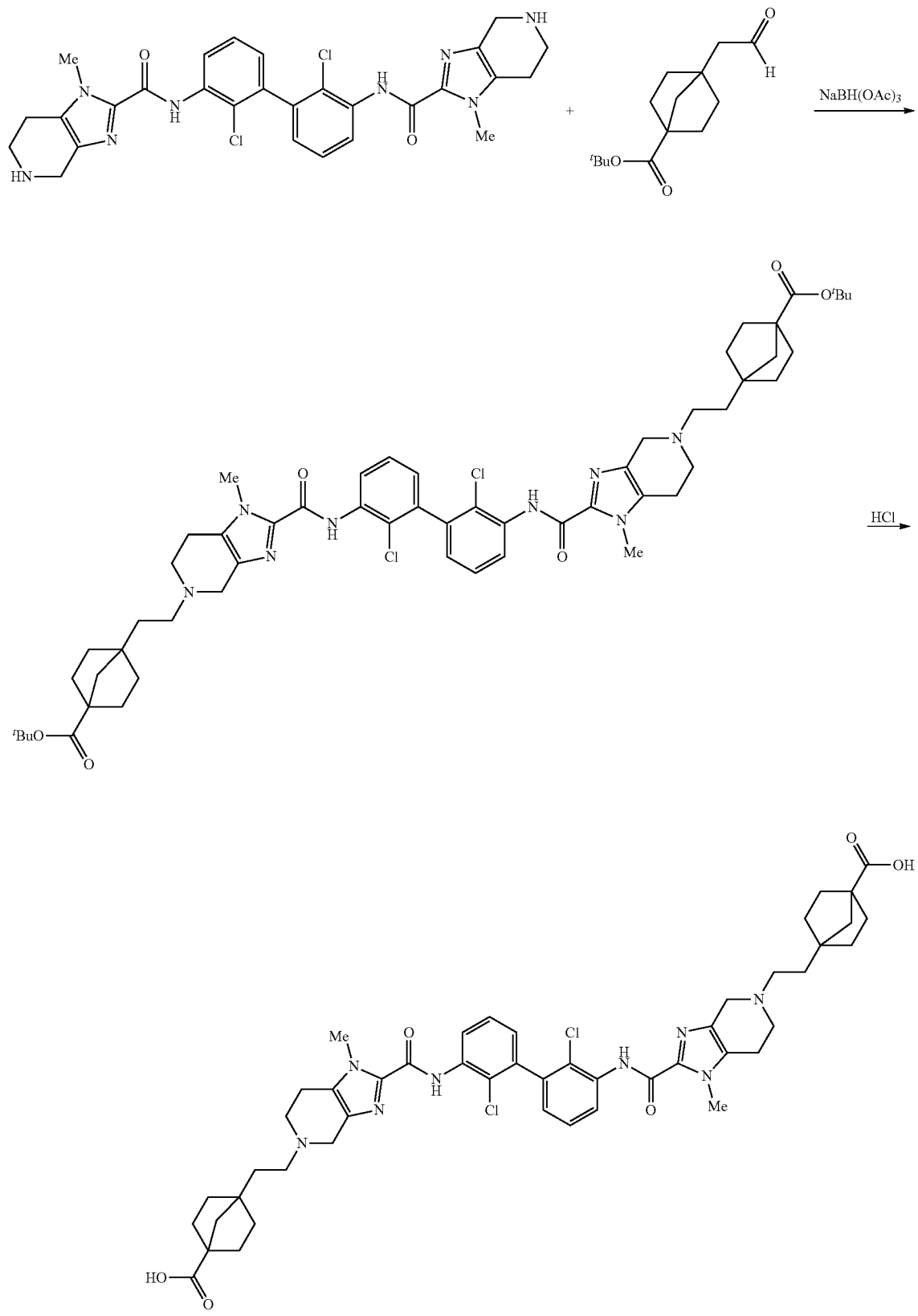

Step 1; di-tert-Butyl 4,4'-(((((2,2'-dichloro-[1,1'-biphenyl]-3,3-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylate)

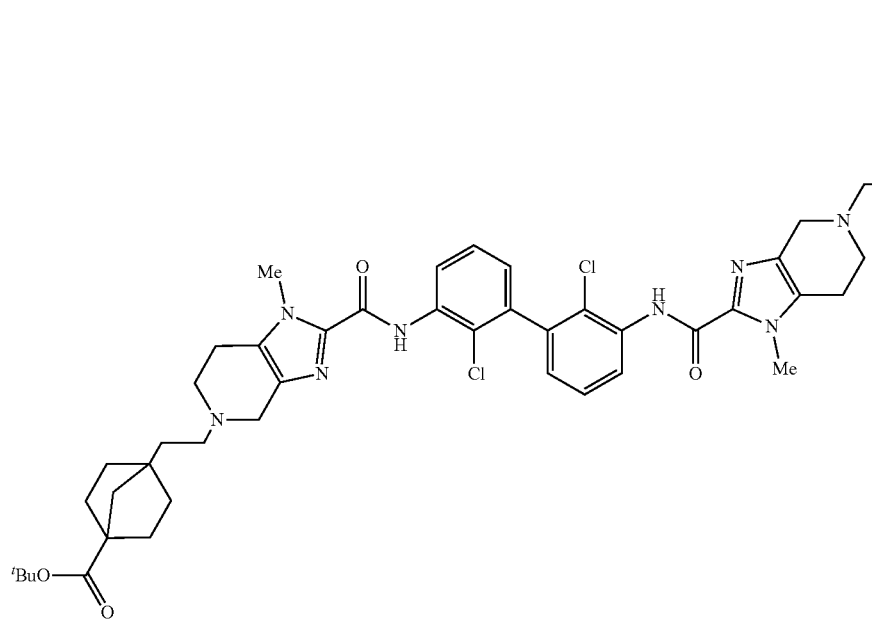

A mixture of N,N'-(2,2'-dichloro-[1,1'-biphenyl]-3,3'-diyl)bis(1-methyl-4,5,6,7-tetrahydro-1H-imidazo[4,5-c]pyridine-2-carboxamide) (Example 1a, Step 4, 20.0 g, 34.5 mmol) and tert-butyl 4-(2-oxoethyl)bicyclo[2.2.1]heptane-1-carboxylate (18.10 g, 76 mmol) in DCM (160 ml) was stirred at room temperature for 10 min. Then sodium triacetoxyborohydride (16.09 g, 76 mmol) was added. The reaction was stirred at room temperature for 4 h. The mixture was diluted with DCM (160 mL), quenched with sodium carbonate (5.12 g, 48.3 mmol) in water (160 mL), and extracted with DCM (100 mL) three times. The combined organic phase was dried, filtered and concentrated. The residue was stirred in MTBE (353 mL) overnight. The solid was filtered and dried to give the desired product, di-tert-butyl 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylate) (32.8 g, 93% yield; HPLC area percentage (220 nM, pH 2): 98.47%), as a white solids, which was used in the subsequent reaction without further purification. MS calculated for $C_{56}H_{72}Cl_2N_8O_6$ $M^+$: m/z=1022.5; found $[(M+2H)/2]^+$: m/z=512.5.

Step 2; 4,4'-(((((2,2-'Dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid)

Hydrochloric acid (HCl) (12 M in water, 39.3 ml, 472 mmol) was added to the solution of di-tert-butyl 4,4'-(((((2,2'-dichloro-[1,1'-biphenyl]-3,3'-diyl)bis(azanediyl))bis(carbonyl))bis(1-methyl-1,4,6,7-tetrahydro-5n-imidazo[4,5-c]pyridine-2,5-diyl))bis(ethane-2,1-diyl))bis(bicyclo[2.2.1]heptane-1-carboxylate) (32.2 g, 31.4 mmol) in acetonitrile (210 ml). The mixture was stirred at 50° C. for 2 h and then cooled to ambient temperature. Then sodium carbonate (19.99 g, 189 mmol) in $H_2O$ (258 mL) was added to quench the acid to pH 6, followed by the addition of $CH_3CN$ (258 mL). The slurry was stirred at room temperature for 3 h and then filtered. The solid was further dried under vacuum to afford the desired product, 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) (28.08 g, 98% yield, containing solvents; HPLC area percentage (220 nM, pH 2): 98.49%), as a white solid, and was used without further purification. LCMS calculated for $C_{48}H_{57}Cl_2N_8O_6$ $(M+H)^+$: m/z=911.4; found 911.3; $^1H$ NMR (400 MHz, DMSO-$d_6$) δ 11.94 (s, 2H), 9.90 (s, 2H), 8.38 (dd, 2H), 7.49 (t, 2H), 7.15 (dd, 2H), 3.91 (s, 6H), 3.42 (s, 4H), 2.76 (t, 4H), 2.67 (t, 4H), 2.57-2.53 (m, 4H), 1.92-1.82 (m, 4H), 1.73 (t, 4H), 1.57-1.47 (m, 8H), 1.44 (s, 4H), 1.42-1.34 (m, 4H) ppm.

Example 2. Preparation of the Compound 1 Di-Sodium Salt

Compound 1 (129.3 mg) was added into 1.5 mL of a 2:1 acetone/water mixture at ambient temperature in a 4 mL clear glass vial with stirring. Then 312 μL of 1N NaOH (2.2 eq) was added into the suspension and stirred at ambient temperature for 1 h. The solid was collected by filtration, washed with acetone, and air dried overnight. The salt ratio between Compound 1 and sodium was determined to be 1.7 by ion chromatography.

The crystallinity of the di-sodium salt was confirmed by XRPD (FIG. 4, Table 2) and further supported by DSC (FIG. 5), indicating the salt having a first endothermic peak with an onset temperature at 47.6° C. and a maximum at 108.3° C., and a second endothermic peak with an onset temperature at 258.4° C. and a maximum at 280.7° C. TGA of the di-sodium salt is provided in FIG. 6, and exhibited approximately 11.5% of weight loss below 100° C.

TABLE 2

XRPD Peak Data for the Compound 1 Di-Sodium Salt

| 2-Theta (°) | Relative Intensity (%) |
|---|---|
| 5.3 | 31.8 |
| 5.8 | 6.8 |
| 7.1 | 100 |
| 9.1 | 4.8 |
| 10.6 | 10.8 |
| 11.7 | 3.8 |
| 11.8 | 6.0 |
| 12.1 | 18.7 |
| 12.6 | 18.1 |
| 13.0 | 15.6 |
| 13.9 | 38.7 |
| 14.3 | 31.6 |
| 15.0 | 17.3 |
| 16.1 | 88.2 |
| 16.6 | 31.3 |
| 17.4 | 63.5 |
| 19.2 | 36.1 |
| 19.6 | 27.2 |
| 21.9 | 10.9 |
| 22.5 | 25.4 |
| 22.7 | 28.6 |
| 24.7 | 5.2 |
| 25.6 | 16.7 |
| 25.7 | 16.4 |
| 27.7 | 8.9 |
| 29.8 | 4.3 |

Example 3. Preparation of the Compound 1 Di-Hydrochloric Acid Salt Form I

Compound 1 (29.6 g, 32.5 mmol) was suspended in acetone (120 mL) and 2.0 N HCl (36 mL, 72.0 mmol). The mixture was heated to 55° C. for 15 min to form a clear solution. After a clear solution was obtained, the reaction mixture was stirred for 30 min and cooled to rt slowly. The solution was polish filtered. Acetone (360 mL) was added portionwise (16 V total). After addition, a cloudy solution formed that was stirred at rt for 4 h. The mixture was filtered to isolate the Compound 1 di-hydrochloric acid salt.

The crude Compound 1 di-hydrochloric acid salt was then transferred to a 1 L flask. Acetone (450 mL, 16 V) and water (30 mL, 1 V) were added and the mixture was heated to 55-60° C. The mixture was stirred at this temperature for 5 h, then slowly cooled to rt and filtered to isolated Compound 1 di-hydrochloric acid salt. The solid was dried in a vacuum oven with nitrogen sweep at 50° C. overnight to provide Compound 1 di-hydrochloric acid salt Form I (28 g, 87% yield, HPLC area percentage (220 nM, pH 2): 99.1%.).

The crystallinity of the di-hydrochloric acid salt Form I was confirmed by XRPD (FIG. 7, Table 3) and further supported by DSC (FIG. 8), indicating the salt having a first endothermic peak with an onset temperature at 31.1° C. and a maximum at 91.4° C., and a second endothermic peak with an onset temperature at 231.0° C. and a maximum at 236.4° C. TGA of the di-hydrochloric acid salt Form I is provided in FIG. 9, and exhibited approximately 8.2% of weight loss below 125° C. and approximately 2.9% of weight loss between 125° C. and 250° C. The di-hydrochloric acid salt Form I was further characterized by $^1$H NMR (FIG. 10). The purity of the di-hydrochloric acid salt Form I was determined by HPLC as 100.0%. The salt ratio between free base and hydrochloric acid was determined to be 2.0 by ion chromatography. LCMS calculated for $C_{48}H_{57}Cl_2N_8O_6$ (M+H)$^+$: m/z=911.4; found 911.3; $^1$H NMR (400 MHz, DMSO-d$_6$): 12.08 (s, 2H), 11.37 (s, 2H), 9.95 (s, 2H), 8.29 (dd, 2H), 7.51 (t, 2H), 7.19 (d, 2H), 4.42 (d, 2H), 4.20 (m, 2H), 3.95 (s, 6H), 3.80 (m, 2H), 3.40 (m, 4H), 3.25 (m, 4H), 3.05 (m, 4H), 2.06 (m, 4H), 1.89 (m, 4H), 1.54 (m, 8H), 1.46 (m, 4H), 1.38 (m, 4H) ppm.

TABLE 3

XRPD Peak Data for the Compound 1 Di-Hydrochloric Acid Salt Form I

| 2-Theta (°) | Relative Intensity (%) |
|---|---|
| 5.7 | 24.7 |
| 7.6 | 5.6 |
| 8.5 | 10.4 |
| 9.0 | 7.2 |
| 9.6 | 100 |
| 9.9 | 19.7 |
| 10.7 | 2.9 |
| 11.8 | 16.5 |
| 12.3 | 12.4 |
| 13.1 | 10.8 |
| 13.4 | 16.5 |
| 13.8 | 14.6 |
| 14.2 | 15.0 |
| 14.5 | 12.9 |
| 14.9 | 4.9 |
| 15.4 | 27.5 |
| 15.8 | 11.6 |
| 16.8 | 68.5 |
| 17.1 | 43.8 |
| 17.3 | 64.2 |
| 17.6 | 59.4 |
| 18.2 | 20.5 |
| 19.2 | 4.7 |
| 20.3 | 19.3 |
| 20.5 | 17.7 |
| 21.4 | 10.8 |
| 22.7 | 17.8 |
| 23.4 | 9.4 |
| 24.0 | 9.9 |
| 24.5 | 14.2 |
| 25.3 | 19.6 |
| 26.4 | 12.2 |
| 27.1 | 20.0 |
| 27.5 | 18.1 |
| 29.1 | 15.4 |

Example 4. Preparation of the Compound 1 Di-Hydrochloric Acid Salt Form II 90 mg of amorphous Compound 1 Di-Hydrochloric Acid Salt was dissolved into 2.6 mL of 10:3 acetonitrile/water mixture at ambient temperature in a 4 mL clear glass vial with stirring. The solution was evaporated without cap at 70° C. to about 0.3 mL. Then 3 mL of acetonitrile was added and heated at 70° C. with closed cap to solid out. The resulted suspension was stirred at ambient temperature for 1 h. The solid was collected by filtration and dried at 50° C. under vacuum overnight.

The crystallinity of the di-hydrochloric acid salt Form II was confirmed by XRPD (FIG. 11, Table 4) and further supported by DSC (FIG. 12), indicating the salt having a first endothermic peak with an onset temperature at 22.2° C. and a maximum at 89.7° C., and a second endothermic peak with an onset temperature at 251.7° C. and a maximum at 258.3° C. TGA of the di-hydrochloric acid salt Form II is provided in FIG. 13, and exhibited approximately 5.4% of weight loss up below 150° C. and approximately 4.1% of weight loss between 150° C. and 250° C.

TABLE 4

XRPD Peak Data for the Compound 1 Di-Hydrochloric Acid Salt Form II

| 2-Theta (°) | Relative Intensity (%) |
|---|---|
| 4.6 | 19.4 |
| 6.9 | 17.4 |
| 8.6 | 5.7 |
| 8.9 | 88.5 |
| 9.2 | 8.1 |
| 9.5 | 14.6 |
| 9.7 | 7.2 |
| 11.2 | 48.0 |
| 11.7 | 33.0 |
| 13.2 | 19.1 |
| 13.9 | 100 |
| 14.3 | 39.5 |
| 14.8 | 54.4 |
| 16.0 | 17.1 |
| 16.7 | 33.0 |
| 17.2 | 49.8 |
| 17.4 | 17.8 |
| 17.7 | 26.0 |
| 17.9 | 50.4 |
| 18.4 | 11.7 |
| 18.9 | 21.9 |
| 19.6 | 29.8 |
| 20.1 | 20.3 |
| 20.7 | 17.9 |
| 21.3 | 19.8 |
| 21.7 | 7.2 |
| 22.0 | 6.8 |
| 22.2 | 11.2 |
| 22.7 | 17.3 |
| 23.5 | 11.6 |
| 23.9 | 13.1 |
| 24.4 | 8.7 |
| 24.8 | 4.4 |
| 25.3 | 84.0 |
| 25.6 | 80.4 |
| 25.8 | 33.8 |
| 26.2 | 15.6 |
| 26.7 | 21.5 |
| 27.2 | 11.1 |
| 27.9 | 6.2 |
| 28.4 | 26.4 |
| 28.8 | 11.3 |

Example 5. Solubility Measurement of Compound 1 Di-Hydrochloric Acid Salt Form I The solubility of Compound 1 Di-Hydrochloric Acid Salt Form I was measured according to Procedure 1 for solubility in 25° C. (Table 5) and Procedure 2 for 50° C. (Table 6) and the results are summarized in Table 7.

TABLE 5

Procedure 1 for solubility measurement of Compound 1 Di-Hydrochloric Acid Salt Form I in various solvents at 25° C.

| Op# | Operation |
|---|---|
| 1 | Added 2 mL solvents listed in the Table 7 to the individual vials |
| 2 | Added Compound 1 Di-Hydrochloric Acid Salt Form I to cloudy solution at 24-25° C. |
| 3 | Added another about 20 mg Compound 1 Di-Hydrochloric Acid Salt Form I |
| 4 | Agitated the mixture at 25 ± 1° C. for 48 h, which is controlled by IKA ® ETS-D5 temperature controller and IKA ® RCT basic safety control |
| 5 | Filtered the supernatant using syringe filter (PTFE, 0.22 μL, 13 mm, Agela Technologies Inc.) |
| 6 | Pipetted the saturated solution into HPLC vials. |
| 7 | Diluted the saturated solution in HPLC vials with MeOH. |
| 8 | HPLC analysis |
| 9 | Calculated solubility as indicated in Table 7 |

TABLE 6

Procedure 2 for solubility measurement of Compound 1 Di-Hydrochloric Acid Salt Form I in various solvents at 50° C.

| Op# | Operation |
|---|---|
| 1 | Added 2 mL solvents listed in the Table 7 to the individual vials |
| 2 | Added Compound 1 Di-Hydrochloric Acid Salt Form I to cloudy solution at 50 ± 1° C. |
| 3 | Added another about 20-30 mg Compound 1 Di-Hydrochloric Acid Salt Form I |
| 4 | Agitated the mixture at 50 ± 1° C. for 24 h, which is controlled by IKA ® ETS-D5 temperature controller and IKA ® RCT basic safety control |
| 5 | Filtered quickly the supernatant using warmed syringe filter at 50 ± 1° C. (PTFE, 0.22 μL, 13 mm, Agela Technologies Inc.) |
| 6 | Pipetted the saturated solution into HPLC vials |
| 7 | Diluted the saturated solution in HPLC vials with MeOH. |
| 8 | HPLC analysis and calculated solubility as indicated in Table 7 |

TABLE 7

Solubility of Compound 1 Di-Hydrochloric Acid Salt Form I in various solvents

| Solvent | Solubility at 25° C. (mg/mL) | Solubility at 50° C. (mg/mL) |
|---|---|---|
| MeCN | 0.02 | 0.01 |
| Chloroform | >50 | >50 |
| Dichloromethane | 0.00 | N/A |
| DMF | 2.98 | 5.48 |
| 1,4-Dioxane | 0.00 | 0.01 |
| Methanol | 18.81 (Form III) * | 22.07 |
| 2-Methoxyethanol | 16.93 | 28.31 |
| MIBK | N/A | 0.01 |
| Toluene | 0.00 | 0.00 |
| Hexane | 0.00 | 0.00 |
| THF | 0.05 | 0.04 |
| Acetone | 0.01 | 0.01 |
| n-BuOH | 0.46 (Form IV) * | 0.42 (Form IV) * |
| MTBE | 0.00 | 0.00 |
| DMSO | >50 | >50 |
| EtOH | 0.39 | 1.10 |
| EtOAc | 0.00 | 0.00 |
| Ethyl formate | 0.00 | 0.00 |
| Heptane | 0.00 | 0.00 |
| Isobutyl acetate | 0.00 | 0.00 |
| IPAc | 0.01 | 0.00 |
| 1-Propanol | 0.71 (Form V) * | 1.12 |
| IPA | 0.65 | 0.98 |
| Water | 12.89 (Form VI) * | 14.78 (Form VI) * |
| MEK | 0.00 | 0.15 |
| 2% Water in Acetone | 0.05 | 0.11 |
| 5% Water in Acetone | 0.32 | 0.56 |
| 10% Water in Acetone | 2.30 | 5.71 |
| 2% Water in Acetonitrile | 0.01 | 0.01 |

TABLE 7-continued

Solubility of Compound 1
Di-Hydrochloric Acid Salt Form I in various solvents

| Solvent | Solubility at 25° C. (mg/mL) | Solubility at 50° C. (mg/mL) |
|---|---|---|
| 5% Water in Acetonitrile | 1.04 | 1.21 |
| 10% Water in Acetonitrile | 3.64 | 6.61 |

N/A: not available, was not studied due to either the low boiling point of the solvent or the HPLC peak overlay with solvent.
* based on the results in Table 8 and Table 9.

Example 6. Phase Equilibration at 25° C. and 50° C.

Phase equilibration studies were designed to provide information on a predominant crystal form for phase identification. Based on its solubility in various solvent systems (Table 7), Compound 1 Di-Hydrochloric Acid Salt Form I was equilibrated in a representative group of solvents at 25±1° C. (Table 8). To the solvents listed in Table 8 and Table 9, was added Compound 1 Di-Hydrochloric Acid Salt Form I until a cloudy solution was obtained, then, about 30 mg of Compound 1 Di-Hydrochloric Acid Salt Form I was added to the cloudy solution. The mixture was stirred at 25±1° C. and 50±1° C. for 2 days respectively. The solid was filtered and analyzed by XRPD to give the results in Table 8 and Table 9.

Equilibration at 25±1° C. (Table 8) resulted in new polymorphic Form III (MeOH), Form IV (n-BuOH), Form V (1-propanol) and Form VI (water). Equilibration at 50±1° C. (Table 9) resulted in new polymorphic Form IV (n-BuOH), and Form VI (water).

TABLE 8

Crystal form for phase equilibration at 25 ± 1° C.

| Solvent | Solid State Form |
|---|---|
| N/A (Compound 1 Di-Hydrochloric Acid Salt Form I) | I |
| N/A (Compound 1 Di-Hydrochloric Acid Salt Form II) | II |
| MeCN | I |
| Chloroform | N/A |
| Dichloromethane | Amorphous + Form I |
| DMF | N/A |
| 1,4-Dioxane | I |
| Methanol | III |
| 2-Methoxyethanol | I |
| MIBK | I |
| Toluene | I |
| Hexane | I |
| THF | I |
| Acetone | Amorphous + Form I |
| n-BuOH | IV |
| MTBE | I |
| DMSO | N/A |
| EtOH | Amorphous + Form I |
| EtOAc | I |
| Ethyl formate | I |
| Heptane | I |
| Isobutyl acetate | I |
| IPAc | I |
| 1-Propanol | V |
| IPA | Amorphous + Form I |
| Water | VI |
| MEK | I |
| 2% water in Acetone | I |
| 5% water in Acetone | I |
| 10% water in Acetone | I |
| 2% water in Acetonitrile | I |
| 5% water in Acetonitrile | I |
| 10% water in Acetonitrile | Amorphous + I |

TABLE 9

Crystal form for phase equilibration at 50° C.

| Solvent | Solid State Form |
|---|---|
| N/A (Compound 1 Di-Hydrochloric Acid Salt Form I) | I |
| MeCN | I |
| Chloroform | N/A |
| DMF | I |
| 1,4-Dioxane | Form IV + amorphous |
| Methanol | I |
| 2-Methoxyethanol | I |
| MIBK | I |
| Toluene | I |
| Hexane | I |
| THF | I |
| Acetone | I |
| n-BuOH | IV |
| MTBE | I |
| DMSO | N/A |
| EtOH | Amorphous + Form I |
| EtOAc | I |
| Ethyl formate | I |
| Heptane | I |
| Isobutyl acetate | I |
| IPAc | I |
| 1-Propanol | I |
| IPA | I |
| Water | VI |
| MEK | I |
| 2% water in Acetone | I |
| 5% water in Acetone | I |
| 10% water in Acetone | I |
| 2% water in Acetonitrile | I |
| 5% water in Acetonitrile | I |
| 10% water in Acetonitrile | Amorphous + Form I |

Example 7. Evaporation at 25±1° C. and 50±1° C.

Evaporation studies were carried out to identify the predominant crystal form during uncontrolled precipitation. Experiments that did not result in any particulate solids (i.e. clear thin films and oils) were not studied further. XRPD was used to study the solid-state morphology of the crystalline forms of the evaporation samples at 25±1° C. and 50±1° C. The results are presented in Table 10 (25±1° C.) and Table 11 (50±1° C.).

TABLE 10

Crystal form identification from evaporation at 25 ± 1° C.

| Solvent | Solid State Form |
|---|---|
| N/A (Compound 1 Di-Hydrochloric Acid Salt Form I) | I |
| Chloroform | Amorphous |
| Dichloromethane | Amorphous + Form I |
| DMF | N/A |

TABLE 10-continued

Crystal form identification from evaporation at 25 ± 1° C.

| Solvent | Solid State Form |
|---|---|
| Methanol | Amorphous |
| 2-Methoxyethanol | Form I + Amorphous |
| EtOH | I |
| 1-Propanol | N/A |
| Water | N/A |
| 5% Water in Acetone | Amorphous + Form I |
| 10% Water in Acetone | Amorphous |
| 5% Water in Acetonitrile | Amorphous |
| 10% Water in Acetonitrile | Amorphous + Form I |

N/A: Not available. Either clear solution or the amount of the precipitate was too small to be analyzed by XRPD.

TABLE 11

Crystal form identification from evaporation at 50 ± 1° C.

| Solvent | Solid State Form |
|---|---|
| N/A (Compound 1 Di-Hydrochloric Acid Salt Form I) | I |
| Dichloromethane | Amorphous |
| DMF | Amorphous + Form I |
| 1,4-Dioxane | N/A |
| Methanol | Amorphous |
| 2-Methoxyethanol | Amorphous + Form I |
| DMSO | Amorphous |
| EtOH | N/A |
| 1-Propanol | Amorphous + Form I |
| IPA | N/A |
| Water | Amorphous |
| 5% Water in Acetone | N/A |
| 10% Water in Acetone | Amorphous |
| 5% Water in Acetonitrile | Amorphous |
| 10% Water in Acetonitrile | Amorphous |

N/A: Not available. Either clear solution or the amount of the precipitate was too small to be analyzed by XRPD.

Example 8. Anti-Solvent Addition

Saturated solution or nearly saturated solution of Compound 1 Di-Hydrochloric Acid Salt was prepared by adding Compound 1 Di-Hydrochloric Acid Salt Form I to the solvents in Table 12 respectively. An anti-solvent was added to induce precipitation. MTBE, toluene, ethyl acetate, IPAc, acetonitrile and 1,4-dioxane were selected as the anti-solvents. Experiments that did not produce any particulate solids on anti-solvent addition were not studied further, and all solids were filtered and analyzed by XRPD. The results are presented in Table 12. Anti-solvent addition of methanol/toluene resulted in new polymorphic Form VII.

TABLE 12

Antisolvent addition of Compound 1 Di-Hydrochloric Acid Salt Form I in various solvents

| Anti-Solvent (mL) | Solvent (mL) | Solid State Form |
|---|---|---|
| N/A (Compound 1 Di-Hydrochloric Acid Salt Form I) | N/A (Compound 1 Di-Hydrochloric Acid Salt Form I) | I |
| MTBE (7.0) | DMF (1.3) | Amorphous + Form I |
| Toluene (7.0) | DMF (1.3) | Amorphous + Form I |
| 1,4-Dioxane (7.0) | DMF (1.3) | Amorphous + Form I |
| Ethyl acetate (7.0) | DMF (1.2) | Amorphous + Form I |
| IPAc (7.0) | DMF (1.3) | Amorphous + Form I |
| MTBE (5.0) | Methanol (1.0) | Amorphous + Form I |
| IPAc (5.0) | Methanol (1.0) | Amorphous + Form I |
| Ethyl acetate (6.0) | Methanol (1.0) Methanol (1.0) | I |
| Toluene (6.0) | After stirring for 40 min to give slurry | VII |
| MTBE (6.5) | 2-Methoxyethanol (1.3) | Amorphous + Form I |
| Toluene (7.0) | 2-Methoxyethanol (1.0) | Amorphous + Form I |
| IPAc (5.0) | 2-Methoxyethanol (0.6) | Amorphous |
| 1,4-Dioxane (7.0) | 2-Methoxyethanol (1.6) | Amorphous + Form I |
| THF (7.0) | Water (1.5) | N/A |
| Acetone (7.0) | Water (1.5) | N/A |
| ACN (7.0) | Water (1.5) | N/A |
| MTBE (10.0) | 10% water/acetone (2.0) | N/A |
| IPAc (7.0) | 10% water/acetone (1.8) | Amorphous |
| Ethyl acetate (8.0) | 10% water/acetone (2.0) | N/A |
| Toluene (7.0 mL) | 10% water/acetone (2.0) | N/A |
| 1,4-Dioxane (7.5 mL) | 10% water/acetone (2.0) | N/A |
| MTBE (7.0) | 10% water/acetonitrile (2.0) | N/A |
| IPAc (7.0) | 10% water/acetonitrile (2.0) | Amorphous |
| Ethyl acetate (7.0) | 10% water/acetonitrile (2.0) | Amorphous |
| 1,4-Dioxane (7.0 mL) | 10% water/acetonitrile (2.0) | N/A |
| Toluene (7.0 mL) | 10% water/acetonitrile (2.0) | N/A |

N/A: Not available. Ether clear solution or the amount of the precipitate was too small to be analyzed by XRPD.

Example 9. Reverse Addition

Saturated solutions and nearly saturated solutions of Compound 1 Di-Hydrochloric Acid Salt Form I were prepared in the solvents listed in Table 13 and added to a larger volume of a miscible anti-solvent. MTBE, 1,4 dioxane, ethyl acetate, toluene and IPAc were selected as the anti-solvents. Experiments that did not produce any particulate solids upon addition to the anti-solvent were not studied further, and all solids were filtered and analyzed by XRPD.

Reverse addition of methanol/IPAc, methanol/ethyl acetate, and methanol/toluene resulted in Compound 1 Di-Hydrochloric Acid Salt Form VIII.

TABLE 13

Reverse addition of Compound 1 Di-Hydrochloric Acid Salt Form I in various solvents

| Solvent (mL) | Anti-Solvent (mL) | Solid State Form |
|---|---|---|
| N/A (Compound 1 Di-Hydrochloric Acid Salt Form I) | N/A (Compound 1 Di-Hydrochloric Acid Salt Form I) | I |
| DMF (1.4) | MTBE (7.5) | Amorphous + Form I |
| DMF (1.3) | Toluene (7.0) | Amorphous + Form I |
| DMF (1.2) | Ethyl acetate (7.0) | Amorphous + Form I |
| DMF (1.3) | 1,4-Dioxane (7.0) | Amorphous + Form I |
| DMF (1.2) | IPAc (7.0) | Amorphous + Form I |
| Methanol (1.0) | MTBE (5.0) | Amorphous |
| Methanol (1.0) | IPAc (5.0) | VIII |
| Methanol (1.0) | Ethyl acetate (6.0) | VIII |
| Methanol (1.0) | Toluene (6.0) | VIII |
| 2-Methoxyethanol (1.3) | MTBE (7.0) | Amorphous |
| 2-Methoxyethanol (1.3) | Toluene (7.0) | Amorphous + Form I |
| 2-Methoxyethanol (1.3) | IPAc (6.5) | Amorphous |
| 2-Methoxyethanol (1.5) | 1,4-Dioxane (7.0) | Amorphous + Form I |
| Water (1.5) | THF (7.0) | N/A |
| Water (1.5) | Acetone (7.0) | N/A |
| Water (1.5) | ACN (7.0) | N/A |
| Water (1.5) | ACN (7.0) | N/A |
| 10% Water/Acetone (2.0) | MTBE (7.0) | N/A |
| 10% Water/Acetone (2.0) | IPAc (7.0) | Amorphous |
| 10% Water/Acetone (2.0) | Ethyl acetate (7.0) | Amorphous |
| 10% Water/acetone (2.0) | 1,4-Dioxane (7.0) | N/A |
| 10% Water/acetone (2.0) | Toluene (7.0) | N/A |

TABLE 13-continued

Reverse addition of Compound 1 Di-Hydrochloric Acid Salt Form I in various solvents

| Solvent (mL) | Anti-Solvent (mL) | Solid State Form |
|---|---|---|
| 10% Water/acetonitrile (2.0) | Toluene (7.0) | N/A |
| 10% Water/acetonitrile (2.0) | MTBE (7.0) | N/A |
| 10% Water/acetonitrile (2.0) | IPAc (7.0) | Amorphous |
| 10% Water/acetonitrile (2.0) | Ethyl acetate (7.0) | Amorphous |
| 10% Water/acetonitrile (2.0) | 1,4-Dioxane (7.0) | Amorphous |

N/A: Not available. Either clear solution or the amount of the precipitate was too small to be analyzed by XRPD.

Example 10. Quenching of Saturated Solution

Saturated and nearly saturated solutions of Compound 1 Di-Hydrochloric Acid Salt Form I prepared at about 25° C. were quenched to about −20° C. to induce precipitation of higher energy forms. Representative solvents in Table 14 were chosen based on solubility data measured at 25° C. The quenching of the saturated methanol solution resulted in Form III.

TABLE 8

Results for Compound 1 Di-Hydrochloric Acid Salt Form I from quenching

| Solvent | Form |
|---|---|
| N/A (Compound 1 Di-Hydrochloric Acid Salt Form I) | I |
| DMF | N/A |
| Methanol | III |
| 2-Methoxyethanol | N/A |
| Water | N/A |
| 10% water/acetone | N/A |
| 10% water/acetonitrile | N/A |

Example 11. Crystallization of Saturated Solution with Heating and Cooling Cycles This experiment was designed to search further for a more stable form than Form I. Saturated and nearly saturated solutions of Compound 1 Di-Hydrochloric Acid Salt Form I were prepared at 50° C. and cooled in a bath slowly by using a programmed circulating bath. To the clear solution (8-10 mL) was added about 20-30 mg Compound 1 Di-Hydrochloric Acid Salt Form I to give a slurry. The formed slurry was then heated to 50° C. over 2 hours and then cooled down to 5° C. over 2 hours. This process was repeated for 3 days and the solid was filtered for further analysis. The results are presented in Table 15. Heating and cooling of the salt in methanol resulted in the new Form IX. PGP-72 TI

TABLE 15

Crystallization of saturated solution of Compound 1 Di-Hydrochloric Acid Salt Form I with heating and cooling recycles

| Solvent | Form |
|---|---|
| N/A (Compound 1 Di-Hydrochloric Acid Salt Form I) | I |
| DMF | Gluey solid |
| Methanol | IX |
| 2-Methoxyethanol | I |
| n-Butanol | IV |
| EtOH | Amorphous + Form I |
| 1-Propanol | V |
| IPA | Amorphous + Form I |
| Water | VI |
| 10% water/acetone | I |
| 5% water/acetonitrile | VII |
| 10% water/acetonitrile | VII |

Example 12. Preparation of the Compound 1 Di-Hydrochloric Acid Salt Form III

To about 2.5 mL of saturated or cloudy solutions of Compound 1 Di-Hydrochloric Acid Salt Form I prepared in methanol was added about 20 mg of Compound 1 Di-Hydrochloric Acid Salt Form I followed by stirring at 25±1° C. for 3 days, which was filtered and analyzed by XRPD as Compound 1 Di-Hydrochloric Acid Salt Form III.

The crystallinity of the di-hydrochloric acid salt Form III was confirmed by XRPD (FIG. 14, Table 16) and further supported by DSC (FIG. 15), indicating the salt having an endothermic peak with an onset temperature at 246.7° C. and a maximum at 258.3° C. TGA of the di-hydrochloric acid salt Form III is provided in FIG. 16, and exhibited approximately 1.3% of weight loss up to about 100° C.

TABLE 16

XRPD Peak Data for the Compound 1 Di-Hydrochloric Acid Salt Form III

| 2-Theta | Relative Intensity % |
|---|---|
| 9.2 | 23.4 |
| 11.2 | 28.9 |
| 14.9 | 100 |
| 17.0 | 92.5 |
| 17.9 | 68.7 |
| 19.7 | 61.2 |
| 22.6 | 23.4 |
| 24.4 | 47.8 |
| 25.9 | 37.3 |
| 26.8 | 25.4 |
| 29.8 | 30.8 |
| 36.4 | 18.9 |

Example 13. Preparation of the Compound 1 Di-Hydrochloric Acid Salt Form IV

To about 3 mL of saturated or cloudy solutions of Compound 1 Di-Hydrochloric Acid Salt Form I prepared in n-butanol was added about 25 mg of Compound 1 Di-Hydrochloric Acid Salt Form I followed by stirring at 25±1° C. for 3 days, which was filtered and analyzed by XRPD as Compound 1 Di-Hydrochloric Acid Salt Form IV.

The crystallinity of the di-hydrochloric acid salt Form IV was confirmed by XRPD (FIG. 17, Table 17) and further supported by DSC (FIG. 18), indicating the salt having an endothermic peak with an onset temperature at 268.1° C. and a maximum at 273.0° C. TGA of the di-hydrochloric acid salt Form IV is provided in FIG. 19, and exhibited approximately 1.2% of weight loss up to about 100° C. The di-hydrochloric acid salt Form IV was further characterized by NMR as an n-butanol channel solvate (FIG. 20).

TABLE 17

XRPD Peak Data for the Compound 1
Di-Hydrochloric Acid Salt Form IV

| 2-Theta | Relative intensity % |
|---|---|
| 5.4 | 100.0 |
| 8.8 | 34.9 |
| 10.9 | 2.7 |
| 13.0 | 3.4 |
| 15.1 | 17.9 |
| 16.2 | 26.4 |
| 17.5 | 59.8 |
| 21.9 | 32.1 |
| 26.3 | 66.0 |

Example 14. Preparation of the Compound 1 Di-Hydrochloric Acid Salt Form V

To about 3 mL of saturated or cloudy solutions of Compound 1 Di-Hydrochloric Acid Salt Form I prepared in n-propanol was added about 30 mg of Compound 1 Di-Hydrochloric Acid Salt Form I followed by stirring at 25±1° C. for 3 days, which was filtered and analyzed by XRPD as Form V.

The crystallinity of the di-hydrochloric acid salt Form V was confirmed by XRPD (FIG. 21, Table 18) and further supported by DSC (FIG. 22), indicating the salt having an endothermic peak with an onset temperature at 240.6° C. and a maximum at 249.1° C. TGA of the di-hydrochloric acid salt Form V is provided in FIG. 23, and exhibited approximately 0.9% of weight loss up to about 100° C. The di-hydrochloric acid salt Form V was further characterized by $^1$H NMR as an n-propanol channel solvate (FIG. 24).

TABLE 18

XRPD Peak Data for the Compound 1
Di-Hydrochloric Acid Salt Form V

| 2-Theta | Relative intensity % |
|---|---|
| 5.8 | 54.4 |
| 9.1 | 100.0 |
| 11.0 | 8.7 |
| 11.6 | 8.4 |
| 13.4 | 69.7 |
| 14.8 | 96.1 |
| 16.6 | 41.8 |
| 17.1 | 44.8 |
| 18.1 | 52.3 |
| 19.3 | 25.4 |
| 21.4 | 28.9 |
| 21.8 | 22.7 |
| 23.1 | 71.8 |
| 24.0 | 27.9 |
| 25.3 | 52.6 |
| 26.2 | 34.6 |
| 27.2 | 80.5 |
| 29.5 | 6.4 |

Example 15. Preparation of the Compound 1 Mono-Hydrochloric Acid Salt Form VI To about 3 mL of saturated at 50° C. of Compound 1 Di-Hydrochloric Acid Salt Form I prepared in water was added about 30 mg of Compound 1 Di-Hydrochloric Acid Salt Form I followed by stirring at 50±1° C. for 2 days, which was filtered and analyzed by XRPD as mono-hydrochloric acid salt Form VI.

The crystallinity of the mono-hydrochloric acid salt Form VI was confirmed by XRPD (FIG. 25, Table 19) and further supported by DSC (FIG. 26), indicating the salt having a first endothermic peak with an onset temperature at 43.7° C. and a maximum at 76.8° C., and a second endothermic peak with an onset temperature at 244.2° C. and a maximum at 250.7° C. TGA of the mono-hydrochloric acid salt Form VI is provided in FIG. 27, and exhibited approximately 1.2% of weight loss up to about 130° C. The mono-hydrochloric acid salt Form VI was further characterized by $^1$H NMR (FIG. 28). Elemental analysis indicated that Form VI may be a mono-chloride hydrate: Calculated for $C_{48}H_{57}Cl_3N_8O_6 \cdot 3H_2O$: C, 57.51; H, 6.33; N, 11.18; Cl, 10.61. Found: C, 55.41; H, 6.18; N, 10.62; Cl, 9.53. Karl-Fisher titration indicated that Form VI contains about 9.43% water.

TABLE 19

XRPD Peak Data for the Compound 1
Mono-Hydrochloric Acid Salt Form VI

| 2-Theta | Relative intensity % |
|---|---|
| 6.4 | 100 |
| 11.1 | 53.9 |
| 12.6 | 21.6 |
| 13.8 | 98 |
| 14.6 | 39.6 |
| 15.7 | 64.5 |
| 16.9 | 24.3 |
| 17.6 | 46.1 |
| 19.0 | 50.2 |
| 19.5 | 24.1 |
| 21.1 | 14.9 |
| 22.8 | 27.1 |
| 24.3 | 24.1 |
| 24.8 | 64.5 |
| 27.0 | 68.8 |
| 28.9 | 9.4 |
| 30.4 | 25.3 |
| 33.6 | 18.6 |
| 40.6 | 7.6 |

Example 16. Preparation of the Compound 1 Di-Hydrochloric Acid Salt Form VII Approximately 5 mL of saturated solutions of Compound 1 Di-Hydrochloric Acid Salt Form I in 10% water/acetonitrile was prepared at 50° C. and cooled to 25° C. in a bath slowly by using a programmed circulating bath. The formed solution was heated to 50° C. over 2 hours and then cooled to 5° C. over 2 hours. This process was repeated for 72 hrs and the solid was isolated by centrifugation and analyzed by XRPD as Form VII.

The crystallinity of the di-hydrochloric acid salt Form VII was confirmed by XRPD (FIG. 29, Table 20) and further supported by DSC (FIG. 30), indicating the salt having a first endothermic peak with an onset temperature at 43.5° C. and a maximum at 84.6° C., and a second endothermic peak with an onset temperature at 260.0° C. and a maximum at 274.2° C. TGA of the di-hydrochloric acid salt Form VII is provided in FIG. 31, and exhibited approximately 2.8% of weight loss up to about 130° C. The di-hydrochloric acid salt Form VII was further characterized by $^1$H NMR as an acetonitrile channel solvate (FIG. 32).

TABLE 20

XRPD Peak Data for the Compound 1
Di-Hydrochloric Acid Salt Form VII

| 2-Theta | Relative intensity % |
|---|---|
| 5.6 | 28.1 |
| 9.9 | 46.4 |
| 11.5 | 30.0 |
| 14.1 | 44.8 |
| 14.9 | 40.5 |
| 17.0 | 100.0 |
| 18.4 | 8.3 |
| 19.3 | 17.3 |
| 24.4 | 93.2 |
| 26.1 | 20.5 |
| 29.6 | 8.0 |

Example 17. Preparation of the Compound 1 Di-Hydrochloric Acid Salt Form VIII To 6 mL of toluene was added 1 mL of saturated solution of Compound 1 Di-Hydrochloric Acid Salt Form I prepared in methanol followed by stirring to give solid, which was filtered and analyzed by XRPD as Form VIII.

The crystallinity of the di-hydrochloric acid salt Form VIII was confirmed by XRPD (FIG. 33, Table 21) and further supported by DSC (FIG. 34), indicating the salt having a first endothermic peak with an onset temperature at 43.8° C. and a maximum at 77.8° C., and a second endothermic peak with an onset temperature at 246.1° C. and a maximum at 252.9° C. TGA of the di-hydrochloric acid salt Form VIII is provided in FIG. 35, and exhibited approximately 2.0% of weight loss up to about 100° C. The di-hydrochloric acid salt Form VIII was further characterized by $^1$H NMR (FIG. 36). PGP-78 TI

TABLE 21

XRPD Peak Data for the Compound 1
Di-Hydrochloric Acid Salt Form VIII

| 2-Theta | Relative intensity % |
|---|---|
| 6.6 | 47.6 |
| 8.5 | 1.4 |
| 11.2 | 27.6 |
| 13.1 | 16.7 |
| 14.7 | 16.8 |
| 16.7 | 100.0 |
| 18.4 | 6.5 |
| 19.0 | 15.6 |
| 24.1 | 71.0 |
| 26.0 | 14.2 |
| 29.2 | 5.8 |

Example 18. Preparation of the Compound 1 Di-Hydrochloric Acid Salt Form IX

Approximately 5 mL of saturated solutions of Compound 1 Di-Hydrochloric Acid Salt Form I in methanol was prepared at 50° C. and cooled to 25° C. in a bath slowly by using a programmed circulating bath. The formed solution was heated to 50° C. over 2 hours and then cooled to 5° C. over 2 hours. This process was repeated for 72 hours and the solid was isolated by centrifugation and analyzed by XRPD as Form IX.

The crystallinity of the di-hydrochloric acid salt Form IX was confirmed by XRPD (FIG. 37, Table 22) and further supported by DSC (FIG. 38), indicating the salt having a first endothermic peak with an onset temperature at 43.4° C. and a maximum at 63.9° C., and a second endothermic peak with an onset temperature at 115.7° C. and a maximum at 131.7° C., and a third endothermic peak with an onset temperature at 266.0° C. and a maximum at 276.1° C. TGA of the di-hydrochloric acid salt Form IX is provided in FIG. 39, and exhibited approximately 2.5% of weight loss up to about 130° C.

TABLE 22

XRPD Peak Data for the Compound 1
Di-Hydrochloric Acid Salt Form IX

| 2-Theta | I % |
|---|---|
| 3.8 | 100 |
| 4.9 | 50.4 |
| 6.6 | 66.7 |
| 10.7 | 71.3 |
| 13.1 | 71.3 |
| 15.3 | 47.3 |
| 16.3 | 62.8 |
| 17.5 | 54.3 |
| 19.1 | 65.9 |
| 24.4 | 40.3 |
| 25.0 | 48.8 |
| 26.6 | 36.4 |
| 27.3 | 62 |

Example 19. Stability Relationship of Compound 1 Di-Hydrochloric Acid Salt Polymorphs To evaluate the transformation of Compound 1 Di-Hydrochloric Acid Salt solid forms, competitive slurry experiments at 25±1° C. and 60±1° C. in the solvent of 10% water/acetone were performed with a mixture of eight polymorphs (Form I, and Form III through Form IX) as described in Table 23 and Table 24.

TABLE 23

Procedure for competitive experiment in 10% water/acetone at 25 ± 1° C.

Figure 40:
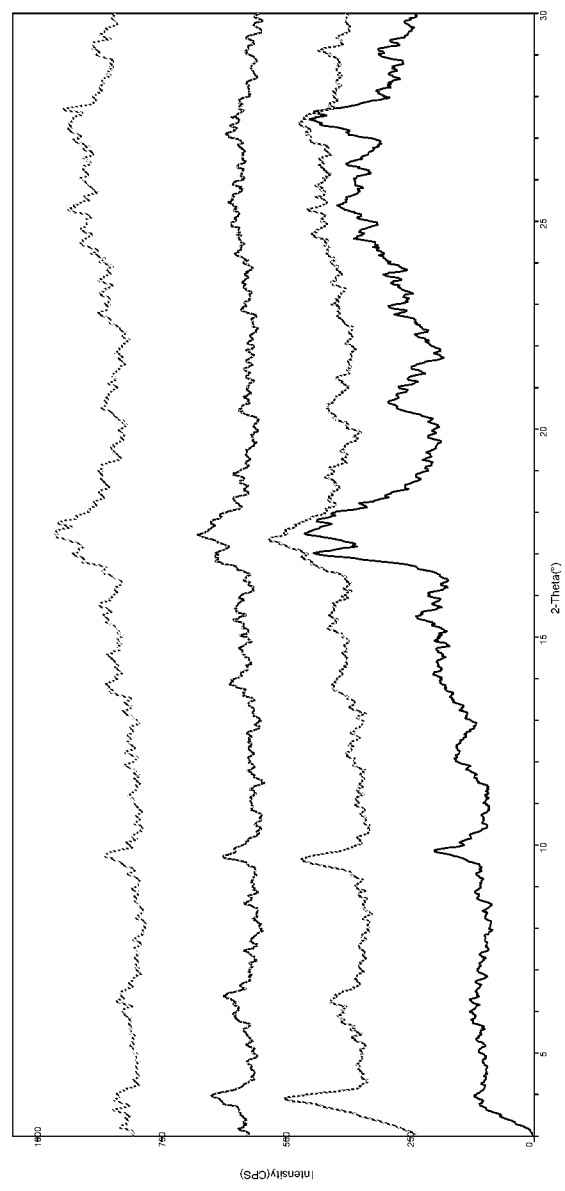
FIG. 40 shows an X-ray Powder Diffraction overlay of Compound 1 di-hydrochloric acid salt mixtures in 10% water/acetone:
1) Mixture of Forms I, III-IX (top spectrum, purple, Stirred for 20 h at 25±1° C.);
2) Mixture of Forms I, III-IX (second spectrum, red, Stirred for 2 h at 25±1° C.);
3) Mixture of Forms I, III-IX (third spectrum, blue, Stirred for 6 h at 25±1° C.); and
4) Form I (bottom spectrum, black).

| OP# | Operation |
|---|---|
| 1 | Added saturated solution of Compound 1 Di-Hydrochloric Acid Salt Form I (2.5 mL) in 10% water/Acetone |
| 2 | Added 5.4 mg of Compound 1 Di-Hydrochloric Acid Salt Form I, and stirred to give a cloudy solution, |
| 3 | Added the mixture of about 5 mg each of Compound 1 Di-Hydrochloric Acid Salt polymorphs (Form III through Form IX) <br> Form III: (5.2 mg) <br> Form IV: (5.4 mg) <br> Form V: (5.1 mg) <br> Form VI: (5.7 mg) (mono) <br> Form VII: (5.3 mg) <br> Form VIII: (5.5 mg) <br> Form IX: (5.1 mg) |
| 4 | Stirred mixture for 2 h at 25 ± 1° C.: XRPD (FIG. 40, second) |
| 5 | Stirred mixture for 6 h at 25 ± 1° C.: XRPD (FIG. 40, third) |
| 6 | Stirred mixture for 20 h at 25 ± 1° C.: XRPD (FIG. 40, top) |

TABLE 24

Procedure for competitive experiment in 10% water/acetone at 60 ± 1° C.

Figure 41:
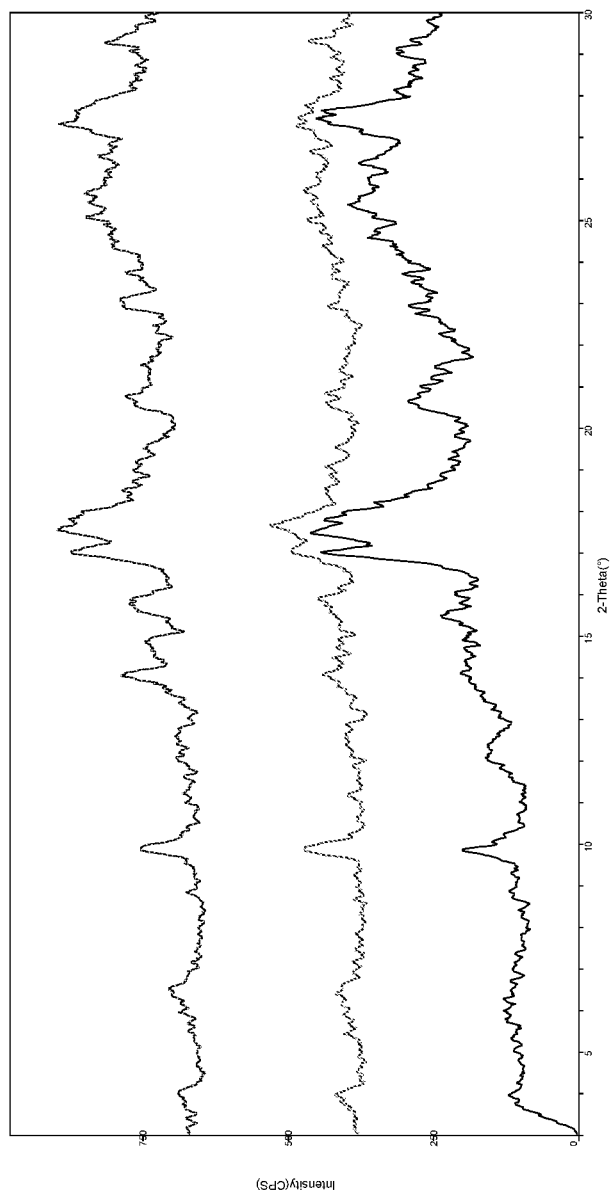
FIG. 41 shows an X-ray Powder Diffraction overlay of Compound 1 di-hydrochloric acid salt mixtures in 10% water/acetone prepared at 60° C.:
1) Mixture of Forms I, III-IX (top spectrum, blue, Stirred for 2 h at 60±1° C.);
2) Mixture of Forms I, III-IX (middle spectrum, red, Stirred for 20 h at 60±1° C.); and
3) Form I (bottom, black).

| OP# | Operation |
|---|---|
| 1 | Added saturated solution of Compound 1 Di-Hydrochloric Acid Salt Form I (2.5 mL) in 10% water/Acetone, prepared at 60° C. |
| 2 | Added 5 mg of Compound 1 Di-Hydrochloric Acid Salt Form I, and stirred to give a cloudy solution, |
| 3 | Added the mixture of about 5 mg each of Compound 1 Di-Hydrochloric Acid Salt polymorphs (Form III through Form IX) |
|  | Form III: (5.0 mg) |
|  | Form IV: (5.1 mg) |
|  | Form V: (5.3 mg) |
|  | Form VI: (5.2 mg) (mono) |
|  | Form VII: (5.4 mg) |
|  | Form VIII: (5.5 mg) |
|  | Form IX: (5.3 mg) |
| 4 | Stirred for 2 h: XRPD (FIG. 41 middle) |
| 5 | Stirred for 20 h at 60° C.: XRPD (FIG. 41 top) |

A mixture of seven polymorphs (Form I, III, IV, V, VII, VIII and Form IX) was converted to Form I after stirring at 25±° C. in 10% water/acetone for 20 hours and at 60±° C. for 2 h. These results indicate that the Form I is the most stable polymorphic form of seven polymorphs in 10% water/acetone at these temperatures.

Example 20. Preparation of the Compound 1 TFA Salt

Step 1: tert-butyl 1-methyl-1,4,6,7-tetrahydro-5H-imidazo[4,5-c]pyridine-5-carboxylate

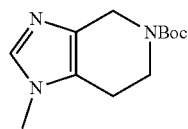 [SMILES: Cn1cnc2c1CCN(C(=O)OC(C)(C)C)C2]

A solution of 1-methyl-4,5,6,7-tetrahydro-1H-imidazo[4,5-c]pyridine (Accela, cat #SY032476: 2.0 g, 14.58 mmol) and (Boc)$_2$O (3.38 mL, 14.58 mmol) in dichloromethane (60 mL) was stirred at room temperature for 1 h. The reaction was quenched with saturated aqueous NaHCO$_3$ solution, and extracted with ethyl acetate. The combined organic layers were washed with brine, dried over Na$_2$SO$_4$, filtered, and concentrated under reduced pressure. The crude product was used directly in the next step without further purification. LC-MS calculated for C$_{12}$H$_{20}$N$_3$O$_2$ (M+H)$^+$: m/z=238.2; found 238.2.

Step 2; 5-tert-butyl 2-methyl 1-methyl-6,7-dihydro-1H-imidazo[4,5-c]pyridine-2,5(4H)-dicarboxylate

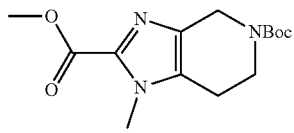 [SMILES: COC(=O)c1nc2c(n1C)CCN(C(=O)OC(C)(C)C)C2]

n-Butyllithium in hexanes (2.5 M, 7.00 mL, 17.49 mmol) was added to a cold (−78° C.) solution of tert-butyl 1-methyl-1,4,6,7-tetrahydro-5H-imidazo[4,5-c]pyridine-5-carboxylate (Step 1: 3.46 g, 14.58 mmol) in tetrahydrofuran (60.0 mL). The reaction mixture was stirred at −78° C. for 10 min prior to the addition of methyl chloroformate (1.69 mL, 21.87 mmol). After being stirred at −78° C. for 30 min, the reaction was then quenched with saturated aqueous NaHCO$_3$ solution, and extracted with ethyl acetate. The combined organic layers were washed with brine, dried over Na$_2$SO$_4$, filtered, and concentrated under reduced pressure. The residue was purified by flash chromatography on a silica gel column eluting with 0-80% ethyl acetate in hexanes to afford the desired product. LC-MS calculated for C$_{14}$H$_{22}$N$_3$O$_4$ (M+H)$^+$: m/z=296.2; found 296.3.

Step 3; tert-butyl 2-((3-bromo-2-chlorophenyl)carbamoyl)-1-methyl-1,4,6,7-tetrahydro-5H-imidazo[4,5-c]pyridine-5-carboxylate

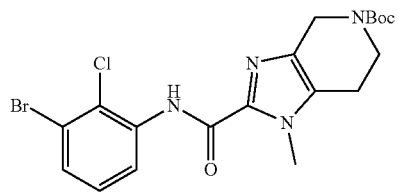 [SMILES: Cn1c(C(=O)Nc2cccc(Br)c2Cl)nc2c1CCN(C(=O)OC(C)(C)C)C2]

Potassium tert-butoxide in THF (1.0 M, 3.39 mL, 3.39 mmol) was added to a solution of 5-tert-butyl 2-methyl 1-methyl-6,7-dihydro-1H-imidazo[4,5-c]pyridine-2,5(4H)-dicarboxylate (Step 2: 500 mg, 1.69 mmol) and 3-bromo-2-chloroaniline (350 mg, 1.69 mmol) in tetrahydrofuran (12.0 mL). After being stirred at room temperature for 30 min, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 0-50% ethyl acetate in hexanes to afford the desired product. LC-MS calculated for C$_{19}$H$_{23}$BrClN$_4$O$_3$ (M+H)$^+$: m/z=469.1/471.1; found 469.1/471.1.

Step 4; tert-butyl 2-((7-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate

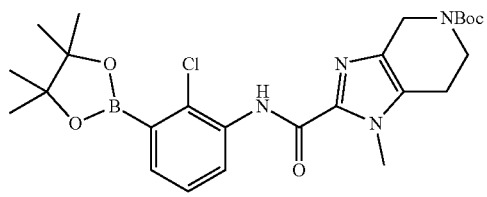 [SMILES: Cn1c(C(=O)Nc2cccc(B3OC(C)(C)C(C)(C)O3)c2Cl)nc2c1CCN(C(=O)OC(C)(C)C)C2]

A mixture of tert-butyl 2-((3-bromo-2-chlorophenyl)carbamoyl)-1-methyl-1,4,6,7-tetrahydro-5H-imidazo[4,5-c]pyridine-5-carboxylate (Step 3: 1.0 g, 2.129 mmol), 4,4,5,5,4',4',5',5'-octamethyl-[2,2']bi[[1,3,2]dioxaborolanyl] (0.649 g, 2.55 mmol), [1,1'-bis(diphenylphosphino)ferrocene]dichloropalladium(II) complexed with dichloromethane (1:1) (0.174 g, 0.213 mmol) and potassium acetate (0.522 g, 5.32 mmol) in 1,4-dioxane (24.0 mL) was purged with nitrogen and then stirred at 110° C. for 3 h. The reaction mixture was cooled to room temperature, diluted with dichloromethane, and then filtered through Celite. The filtrate was concentrated under reduced pressure, and the residue was purified by flash chromatography on a silica gel column eluting with 0-30% ethyl acetate in hexanes to afford the desired product. LC-MS calculated for $C_{25}H_{35}BClN_4O_5$ (M+H)$^+$: m/z=517.2; found 517.2.

Step 5; tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

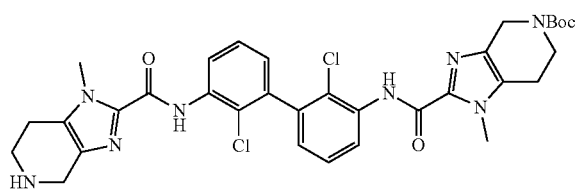 [SMILES: Cn1c(C(=O)Nc2cccc(-c3cccc(NC(=O)c4nc5c(n4C)CCN(C(=O)OC(C)(C)C)C5)c3Cl)c2Cl)nc2c1CCNC2]

A mixture of tert-butyl 2-((3-bromo-2-chlorophenyl)carbamoyl)-1-methyl-1,4,6,7-tetrahydro-5H-imidazo[4,5-c]pyridine-5-carboxylate (Step 3: 900 mg, 1.92 mmol) in trifluoroacetic acid (4.0 mL) and dichloromethane (8.0 mL) was stirred at room temperature for 1 h. The reaction mixture was concentrated under reduced pressure. A mixture of the above residue, tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Step 4: 1188 mg, 2.30 mmol), sodium carbonate (1015 mg, 9.58 mmol) and [1,1-bis(di-cyclohexylphosphino)ferrocene]dichloropalladium(II) (145 mg, 0.19 mmol) in 1,4-dioxane (12.0 mL) and water (6.0 mL) was purged with nitrogen and then stirred at 110° C. for 2 h. After being cooled to room temperature, the reaction mixture was diluted with water and extracted with dichloromethane. The combined organic layers were dried over $Na_2SO_4$, filtered, and concentrated under reduced pressure. The residue was purified by flash chromatography on a silica gel column eluting with 0-10% methanol in dichloromethane to afford the desired product. LC-MS calculated for $C_{33}H_{37}Cl_2N_8O_4$ (M+H)$^+$: m/z=679.2; found 679.2.

Step 6; methyl 4-formylbicyclo[2.2.1]heptane-1-carboxylate

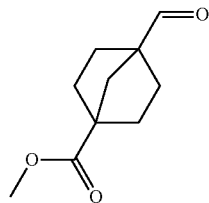

A mixture of methyl 4-(hydroxymethyl)bicyclo[2.2.1]heptane-1-carboxylate (PharmaBlock, cat #PBZ3820: 400 mg, 2.17 mmol) and Dess-Martin periodinane (1381 mg, 3.26 mmol) in dichloromethane (12.0 mL) was stirred at room temperature for 2 h. The reaction mixture was quenched with 20% aqueous $Na_2S_2O_3$ solution and saturated aqueous $NaHCO_3$ solution, and extracted with ethyl acetate. The combined organic layers were washed with brine, dried over $Na_2SO_4$, filtered, and concentrated under reduced pressure. The crude product was used directly in the next step without further purification.

Step 7; methyl 4-(2-oxoethyl)bicyclo[2.2.1]heptane-1-carboxylate

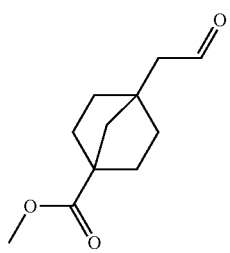

Potassium tert-butoxide in THF (1.0 M, 4.39 mL, 4.39 mmol) was added to a suspension of chloro(methoxymethyl)triphenylphosphorane (1505 mg, 4.39 mmol) in tetrahydrofuran (12.0 mL). The reaction mixture was stirred at room temperature for 1 h prior to the addition of methyl 4-formylbicyclo[2.2.1]heptane-1-carboxylate (Step 6: 400 mg, 2.195 mmol). After being stirred at room temperature for 5 h, the reaction mixture was quenched with water, and extracted with ethyl acetate. The combined organic layers were washed with brine, dried over $Na_2SO_4$, filtered, and concentrated under reduced pressure. The residue was dissolved in tetrahydrofuran (12.0 mL), and then treated with HCl in water (4.0 M, 11 mL, 43.9 mmol) at room temperature for 1 h. The reaction mixture was diluted with water and extracted with ethyl acetate. The combined organic layers were washed with brine, dried over $Na_2SO_4$, filtered, and concentrated under reduced pressure. The crude product was used directly in the next step without further purification.

Step 8; methyl 4-(2-(2-((2,2'*dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate

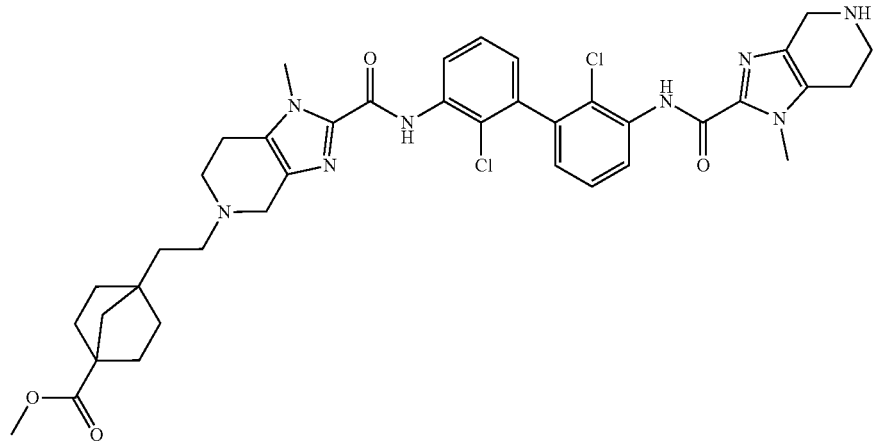 [SMILES: COC(=O)C12CCC(CCN3CCc4c(nc(C(=O)Nc5cccc(-c6cccc(NC(=O)c7nc8c(n7C)CCNC8)c6Cl)c5Cl)n4C)C3)(CC1)C2]

Methyl 4-(2-oxoethyl)bicyclo[2.2.1]heptane-1-carboxylate (Step 7: 43.3 mg, 0.221 mmol) was added to a mixture of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 5: 100 mg, 0.147 mmol) and sodium triacetoxyborohydride (94 mg, 0.441 mmol) in dichloromethane (1.5 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was treated with dichloromethane (1.0 mL) and trifluoroacetic acid (0.5 mL) at room temperature for 1 h. The reaction mixture was concentrated under reduced pressure. The residue was treated with saturated aqueous NaHCO$_3$ solution, and extracted with dichloromethane. The combined organic layers were dried over Na$_2$SO$_4$, filtered, and concentrated under reduced pressure. The residue was purified by flash chromatography on a silica gel column eluting with 0-10% methanol in dichloromethane to afford the desired product. LC-MS calculated for C$_{39}$H$_{45}$Cl$_2$N$_8$O$_4$ (M+H)$^+$: m/z=759.3; found 759.3.

Step 9; 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) (Compound 1 Isolated as TFA Salt)

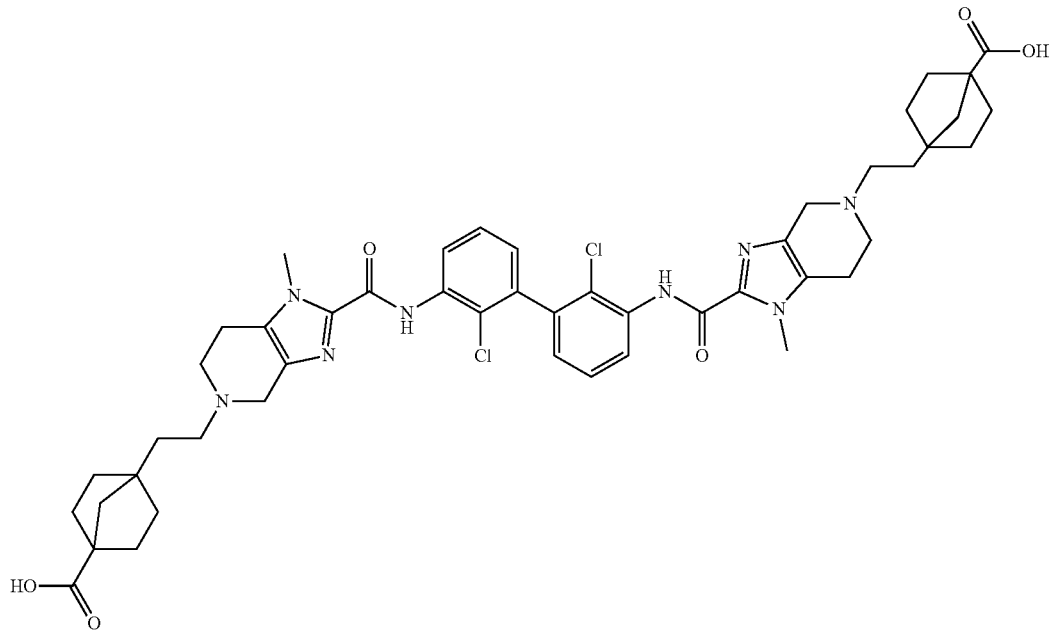 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCC13CCC(C(=O)O)(CC1)C3)C2]

Methyl 4-(2-oxoethyl)bicyclo[2.2.1]heptane-1-carboxylate (Step 7: 5.2 mg, 0.026 mmol) was added to a mixture of methyl 4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (Step 8: 10 mg, 0.013 mmol), and sodium triacetoxyborohydride (8.37 mg, 0.039 mmol) in dichloromethane (0.20 mL). After being stirred at room temperature for 2 h, the reaction mixture was quenched with saturated aqueous NaHCO$_3$ solution, and extracted with dichloromethane. The combined organic layers were washed with brine, dried over Na$_2$SO$_4$, filtered and concentrated under reduced pressure. The residue was dissolved in THF/MeOH/water (0.1 mL/0.1 mL/0.05 mL), and treated with lithium hydroxide, monohydrate (5.5 mg, 0.132 mmol). After being stirred at 30° C. for 3 h, the reaction mixture was diluted with methanol, and purified by prep-HPLC (pH=2, acetonitrile/water+TFA) to give the desired product as the TFA salt. LC-MS calculated for C$_{48}$H$_{57}$Cl$_2$N$_8$O$_6$ (M+H)$^+$: m/z=911.4; found 911.4. $^1$H NMR (600 MHz, DMSO-d$_6$) δ 12.08 (s, 2H), 9.93 (s, 2H), 8.29 (d, J=8.1 Hz, 2H), 7.51 (t, J=7.9 Hz, 2H), 7.18 (d, J=7.7 Hz, 2H), 4.56-4.44 (m, 2H), 4.30-4.18 (m, 2H), 3.95 (s, 6H), 3.87-3.78 (m, 2H), 3.52-3.20 (m, 6H), 3.14-2.94 (m, 4H), 2.04-1.82 (m, 8H), 1.58-1.48 (m, 8H), 1.46 (s, 4H), 1.42-1.32 (m, 4H).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A salt, which is 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt.

2. The salt of claim 1, wherein the salt is Form I of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt.

3. The salt of claim 2, characterized by having an X-ray powder diffraction pattern as substantially as shown in FIG. 7.

4. The salt of claim 2, characterized by having a DSC thermogram substantially as depicted in FIG. 8.

5. The salt of claim 2, characterized by having a thermogravimetric analysis (TGA) thermogram substantially as depicted in FIG. 9.

6. The salt of claim 2, characterized by having at least four X-ray powder diffraction (XRPD) peaks, in terms of 2-theta (±0.2 degrees), selected from 5.7, 8.5, 9.6, 9.9, 11.8, 12.3, 13.1, 13.4, 13.8, 14.2, 14.5, 15.4, 15.8, 16.8, 17.3 and 17.6 degrees.

7. The salt of claim 2, characterized by having characteristic X-ray powder diffraction (XRPD) peaks, in terms of 2-theta (±0.2 degrees), at 5.7, 8.5, 9.6, 9.9, 11.8, 12.3, 13.1, 13.4, 13.8, 14.2, 14.5, 15.4, 15.8, 16.8, 17.3 and 17.6 degrees.

8. The salt of claim 2, wherein the differential scanning calorimetry (DSC) thermogram is characterized by having a first endothermic peak with an onset temperature at 31.1° C.±3° C. and a maximum at 91.4° C.±3° C., and a second endothermic peak with an onset temperature at 231.0° C.±3° C. and a maximum at 236.4° C.±3° C.

9. The salt of claim 1, wherein the salt is Form II of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt.

10. The salt of claim 9, characterized by having at least four X-ray powder diffraction (XRPD) peaks, in terms of 2-theta (±0.2 degrees), selected from 4.6, 6.9, 8.9, 11.2, 11.7, 13.2, 13.9, 14.3, 14.8, 16.0, 16.7, 17.2, 17.9, 25.3 and 25.6 degrees.

11. The salt of claim 9, wherein the differential scanning calorimetry (DSC) thermogram is characterized by having a first endothermic peak with an onset temperature at 22.2° C.±3° C. and a maximum at 89.7° C.±3° C., and a second endothermic peak with an onset temperature at 251.7° C.±3° C. and a maximum at 258.3° C.±3° C.

12. The salt of claim 1, wherein the salt is Form III of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt.

13. The salt of claim 12, characterized by having at least four X-ray powder diffraction (XRPD) peaks, in terms of 2-theta (±0.2 degrees), selected from 9.2, 11.2, 14.9, 17.0, 17.8, 19.7, 24.4 and 25.9 degrees.

14. The salt of claim 12, wherein the differential scanning calorimetry (DSC) thermogram is characterized by having an endothermic peak with an onset temperature of 247±3° C. and a maximum at 258±3° C. in a differential scanning calorimetry (DSC) thermogram.

15. The salt of claim 1, wherein the salt is Form IV of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt.

16. The salt of claim 15, characterized by having at least four X-ray powder diffraction (XRPD) peaks, in terms of 2-theta (±0.2 degrees), selected from 5.4, 8.8, 10.9, 13.0, 15.1, 16.2, 17.5, 21.9 and 26.3 degrees.

17. The salt of claim 15, wherein the differential scanning calorimetry (DSC) thermogram is characterized by having an endothermic peak with an onset temperature of 268±3° C. and a maximum at 273±3° C.

18. The salt of claim 1, wherein the salt is Form V of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt.

19. The salt of claim 18, characterized by having at least four X-ray powder diffraction (XRPD) peaks, in terms of 2-theta (±0.2 degrees), selected from 5.8, 9.1, 13.4, 14.8, 16.6, 17.1, 18.1 and 19.3 degrees.

20. The salt of claim 18, wherein the differential scanning calorimetry (DSC) thermogram is characterized by having an endothermic peak with an onset temperature of 241±3° C. and a maximum at 249±3° C.

21. The salt of claim 1, wherein the salt is Form VII of 4,4'-(((((2,2'-dichloro-[1,1'-biphenyl]-3,3'-diyl)bis(azanediyl))bis(carbonyl))bis(1-methyl-1,4,6,7-tetrahydro- 5H-imidazo[4,5-c]pyridine-2,5-diyl))bis(ethane-2,1-diyl))bis(bicyclo[2.2.1]heptane-1-carboxylic acid) di-hydrochloric acid salt.

22. The salt of claim 21, characterized by having at least four X-ray powder diffraction (XRPD) peaks, in terms of 2-theta (±0.2 degrees), selected from 5.7, 9.9, 11.5, 14.1, 14.9, 17.0 and 24.4 degrees.

23. The salt of claim 21, wherein the differential scanning calorimetry (DSC) thermogram characterized by having a first endothermic peak with an onset temperature at 44±3° C. and a maximum at 85±3° C., and a second endothermic peak with an onset temperature at 260±3° C. and a maximum at 274±3° C. in a differential scanning calorimetry (DSC) thermogram.

24. The salt of claim 1, wherein the salt is Form VIII of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt.

25. The salt of claim 24, characterized by having at least four X-ray powder diffraction (XRPD) peaks, in terms of 2-theta (±0.2 degrees), selected from 6.6, 11.2, 13.1, 14.7, 16.7, 19.0 and 24.1 degrees.

26. The salt of claim 24, wherein the differential scanning calorimetry (DSC) thermogram is characterized by having a first endothermic peak with an onset temperature at 44±3° C. and a maximum at 78±3° C., and a second endothermic peak with an onset temperature at 246±3° C. and a maximum at 253±3° C.

27. The salt of claim 1, wherein the salt is Form IX of 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) di-hydrochloric acid salt.

28. The salt of claim 27, characterized by having at least four X-ray powder diffraction (XRPD) peaks, in terms of 2-theta (±0.2 degrees), selected from 3.8, 6.6, 10.7, 13.1, 15.3, 16.3, 17.5 and 19.1 degrees.

29. The salt of claim 27, wherein the differential scanning calorimetry (DSC) thermogram is characterized by having a first endothermic peak with an onset temperature at 43±3° C. and a maximum at 64±3° C., and a second endothermic peak at 116±3° C. and a maximum at 132±3° C., and a third endothermic peak at 266±3° C. and a maximum at 276±3° C.

30. A pharmaceutical composition comprising a salt of claim 1, and a pharmaceutically acceptable carrier or excipient.

31. A solid oral dosage form comprising the pharmaceutical composition of claim 30.

32. A process of preparing the salt of claim 1, comprising reacting said Compound 1 with at least two equivalents of hydrochloric acid.

33. A process of preparing the salt of claim 2, comprising:
a) preparing a suspension of Compound 1 and at least 2 equivalents of hydrochloric acid in a solvent comprising acetone;
b) heating the suspension of a) to above room temperature to form a clear solution;
c) cooling the clear solution of b) to about room temperature;
d) adding a solvent comprising acetone to the mixture of c) to form a cloudy solution; and
e) filtering the cloudy solution of d) to provide said Form I as a solid.

* * * * *

UNITED STATES PATENT AND TRADEMARK OFFICE
CERTIFICATE OF CORRECTION

PATENT NO. : 11,866,451 B2
APPLICATION NO. : 17/094396
DATED : January 9, 2024
INVENTOR(S) : Zhongjiang Jia et al.

Page 1 of 1

It is certified that error appears in the above-identified patent and that said Letters Patent is hereby corrected as shown below:

In the Claims

Column 92, Lines 34-35, Claim 14, after "C." delete "in a differential scanning calorimetry (DSC) thermogram.";

Column 93, Lines 13-14, Claim 23, after "C." delete "in a differential scanning calorimetry (DSC) thermogram.".

Signed and Sealed this
Fifth Day of March, 2024

Katherine Kelly Vidal
*Director of the United States Patent and Trademark Office*